(12) United States Patent
Heath

(10) Patent No.: US 11,189,368 B2
(45) Date of Patent: Nov. 30, 2021

(54) SYSTEMS, COMPUTER MEDIA, AND METHODS FOR USING ELECTROMAGNETIC FREQUENCY (EMF) IDENTIFICATION (ID) DEVICES FOR MONITORING, COLLECTION, ANALYSIS, USE AND TRACKING OF PERSONAL DATA, BIOMETRIC DATA, MEDICAL DATA, TRANSACTION DATA, ELECTRONIC PAYMENT DATA, AND LOCATION DATA FOR ONE OR MORE END USER, PET, LIVESTOCK, DAIRY COWS, CATTLE OR OTHER ANIMALS, INCLUDING USE OF UNMANNED SURVEILLANCE VEHICLES, SATELLITES OR HAND-HELD DEVICES

(71) Applicant: Stephan Heath, Highlands Ranch, CO (US)

(72) Inventor: Stephan Heath, Highlands Ranch, CO (US)

( * ) Notice: Subject to any disclaimer, the term of this patent is extended or adjusted under 35 U.S.C. 154(b) by 862 days.

(21) Appl. No.: 15/863,669

(22) Filed: Jan. 5, 2018

(65) Prior Publication Data
US 2018/0211718 A1  Jul. 26, 2018

Related U.S. Application Data

(63) Continuation-in-part of application No. 14/998,746, filed on Dec. 23, 2015, now abandoned.

(51) Int. Cl.
*G06Q 30/02* (2012.01)
*G16H 10/65* (2018.01)
*G16H 10/40* (2018.01)
*G16H 20/10* (2018.01)
*A01K 29/00* (2006.01)
(Continued)

(52) U.S. Cl.
CPC ........... *G16H 10/65* (2018.01); *A01K 11/006* (2013.01); *A01K 29/005* (2013.01); *G06K 7/10376* (2013.01); *G06K 19/07762* (2013.01); *G06Q 30/0201* (2013.01); *G16H 10/40* (2018.01); *G16H 20/10* (2018.01); *G16H 80/00* (2018.01)

(58) Field of Classification Search
None
See application file for complete search history.

(56) References Cited

U.S. PATENT DOCUMENTS

2005/0234742 A1* 10/2005 Hodgdon ............... G06Q 10/10
705/2
2011/0015504 A1*  1/2011 Yoo ....................... A61B 5/6897
600/301

(Continued)

*Primary Examiner* — Alan Torrico-Lopez
(74) *Attorney, Agent, or Firm* — Peter B. Scull; EIP US LLP

(57) ABSTRACT

Methods, apparatuses, non-transitory computer readable storage media, computer systems, networks, and/or systems for monitoring, collection, analysis, use and tracking of personal data, biometric data, medical data, transaction data, electronic payment data, location data and other data to develop a profile for one or more end user, pet, livestock, dairy cows, cattle or other animal using radio and other frequency tags and relaying data from EMFID tag interactions to a database that can be accessed by members of a network, and further including the use of unmanned surveillance vehicles, satellites or hand-held devices for monitoring, collection, and/or analysis of EMFID data.

6 Claims, 22 Drawing Sheets

(51) Int. Cl.
*A01K 11/00* (2006.01)
*G06K 7/10* (2006.01)
*G06K 19/077* (2006.01)
*G16H 80/00* (2018.01)

(56) References Cited

U.S. PATENT DOCUMENTS

| | | | | |
|---|---|---|---|---|
| 2013/0073336 | A1* | 3/2013 | Heath | G06Q 30/02 |
| | | | | 705/7.29 |
| 2013/0222141 | A1* | 8/2013 | Rhee | G16H 50/80 |
| | | | | 340/573.3 |
| 2013/0268357 | A1* | 10/2013 | Heath | G06Q 30/02 |
| | | | | 705/14.53 |
| 2014/0121558 | A1* | 5/2014 | Alonsoperez Lanza | ...... |
| | | | | A61B 5/0008 |
| | | | | 600/549 |
| 2014/0340217 | A1* | 11/2014 | Moenning | A61B 5/14542 |
| | | | | 340/539.11 |
| 2014/0358523 | A1* | 12/2014 | Sheth | G06F 40/30 |
| | | | | 704/9 |
| 2014/0372133 | A1* | 12/2014 | Austrum | G16H 50/30 |
| | | | | 705/2 |
| 2015/0286710 | A1* | 10/2015 | Chang | G06F 16/36 |
| | | | | 706/12 |

* cited by examiner

*Process 400B*

SYSTEMS, COMPUTER MEDIA, AND METHODS FOR USING ELECTROMAGNETIC FREQUENCY (EMF) IDENTIFICATION (ID) DEVICES FOR MONITORING, COLLECTION, ANALYSIS, USE AND TRACKING OF PERSONAL DATA, BIOMETRIC DATA, MEDICAL DATA, TRANSACTION DATA, ELECTRONIC PAYMENT DATA, AND LOCATION DATA FOR ONE OR MORE END USER, PET, LIVESTOCK, DAIRY COWS, CATTLE OR OTHER ANIMALS, INCLUDING USE OF UNMANNED SURVEILLANCE VEHICLES, SATELLITES OR HAND-HELD DEVICES

FIELD

The subject matter here relates to systems, computer media, and methods for monitoring, collection, analysis, use and tracking of personal data, biometric data, medical data, transaction data, electronic payment data, location data and other data to develop a profile for one or more end user, pet, livestock, dairy cows, cattle or other animal using radio and other frequency tags and relaying data from EMFID tag interactions to a database that can be accessed by members of a network, and further including the use of unmanned surveillance vehicles, satellites or hand-held devices for monitoring, collection, and/or analysis of EMFID data.

BACKGROUND

Food-animal production has intensified over the past 50 years. The number of livestock and poultry farms in the United States has decreased, but the density of animals on those farms has increased substantially. Production also has become more efficient; a greater quantity of commodities is produced by fewer animals. The increase in efficiency results from several factors, including preventive medicine, disease prevention, genetic selection, and improved nutrition and management.

Dairy cattle (also called dairy cows) are cattle cows bred for the ability to produce large quantities of milk, from which dairy products are made. Dairy cows generally are of the species *Bos taurus*. Historically, there was little distinction between dairy cattle and beef cattle, with the same stock often being used for both meat and milk production. Today, the bovine industry is more specialized and most dairy cattle have been bred to produce large volumes of milk. The United States dairy herd produced 83.9 billion kg (185 billion lbs.) of milk in 2007, up from 52.6 billion kg (116 billion lbs.) in 1950, yet there were only about 9 million cows on U.S. dairy farms—about 13 million fewer than there were in 1950. The top breed of dairy cow within Canada's national herd category is Holstein, taking up 93% of the dairy cow population, have an annual production rate of 10 257 kg of milk per cow that contains 3.9% butter fat and 3.2% protein.

To meet projected demand for animal and dairy products, the industry must streamline production and advance capacity to prevent, detect, diagnose, and treat diseases in livestock, dairy cows, cattle or other animals. The quality of animal products is affected by production methods and marketing practices. Scientists study the conditions in which animals are raised as well as how animal products are manufactured and marketed in order to produce a good quality of life for animals, healthy livestock that reach full production potential, and a nutritious and safe food supply.

Infectious diseases of livestock, dairy cows, cattle or other animals are a major threat to global animal health and the safety of our food supply. RFID microchips can be implanted into in people, pets, livestock, dairy cows, cattle or other animals, or swallowed and lodged in the rumen part of the stomach. Most commonly, it's in a disc slightly thicker than a quarter that can be attached to the animal's ear. Besides assisting with disease traceability, RFID tags allow ranchers and farmers to instantly pull up information on an animal's lineage, weight, health records, diseases and production history.

Thus there is a need to provide new data ID tags that provide monitoring, collection, analysis, use and/or tracking of personal data, biometric data, medical data, transaction data, electronic payment data, location data, track movement data, logistics data, transportation data, and other data to develop a profile for one or more end user, pet, livestock, dairy cows, cattle or other animal using radio and other frequency tags and relaying data from EMFID tag interactions to a database that can be accessed by members of a network, and further including the use of unmanned surveillance vehicles, satellites or hand-held devices for monitoring, collection, and/or analysis of EMFID data.

SUMMARY

Alternative embodiments of the invention optionally relate to one or more of methods, apparatuses, non-transitory computer readable storage media, computer systems, networks, and/or systems using a wireless device for detection and tracking of user's data that uses electromagnetic frequency (EMF) identification (EMFID) technologies to provide data transfer and communications for EMFID sensors for automatic identification data collection of personal data for one or more individuals or end user, multiple EMFID tag interactions, remotely storing, monitoring and retrieving data and transaction data, electronic payment data, location data, track movement data, logistics data, transportation data, physical, emotional and mental state data, integration of biometric data, healthcare, physical health conditions, medical conditions, track movement, logistics, transportation, track diseases for pets, livestock, dairy cows, cattle or other animals, diseases and conditions for disease control and prevention, monitoring antibiotics, pharmaceutical data and other data to develop a profile for one or more end user, pet, livestock, dairy cows, cattle or other animals, including tracking movement, logistics data, and/or location data using radio and other frequency tags and relaying data from EMFID tag interactions to a database that can be accessed by members of a network, wherein predictive analytics are used for one or more individuals analysis, marketing, monitoring, behavior, location, track movement, diagnosis and promotions, of interest, of medical care, drugs, products, illegal activity, or other services, of interest, of past, present or future customers, users, targets and/or target markets, and further including the use of unmanned surveillance vehicles, satellites or hand-held devices for monitoring, collection, and/or analysis of EMFID data.

One or more embodiments can optionally include the use of one or more data collection, storage, communication, and/or analysis, or protection therefrom, using an EMFID, such as an EMFID, transmitter, receivers or transceivers, that can be provided in any form and can include one or more of EMF frequencies, wavelengths, types, fields, packets, photons, patterns, standing or dynamic, bidirectional or multidirectional, scalar elements, and/or ranges or combinations thereof, to provide data transfer to one or more EMFID tag data recording, storage, communication, analysis, transfer, or other uses, such as, but not limited to components, compounds, compositions, EMF emissions, or data relating to one or more of product labeling (e.g., pharmaceutical products), encoded or deliverable compounds compositions or EMF emissions, e.g., but not limited to one or more of vaccinations, edible or administrable drugs, compounds or compositions, product labels, ID, content, dosing, recipient, physician, hospital, insurance, pharma/healthcare or other service provider, lot, dates, financial or sales information, manufacturing, farming, animal farming, industrial livestock production, tracking, GPS, RTLS, travel, currency, monitoring, or other ID information of products or services and/or microchip and/or nanobots implantable in or administered to animals and/or individuals.

The apparatuses or methods optionally further include the use of unmanned surveillance vehicles, satellites or handheld devices for monitoring, collection, and/or analysis of EMFID data. The present developments optionally provide wherein an EMFID comprising device is used with or includes an unmanned aerial vehicle (e.g., an air, land, or sea drone, robot, or other vehicles optionally include audio, visual, or other input that is configured to monitor, collect, and/or analyze biometric data, transaction data, electronic payment data, location data, track movement data, logistics data, transportation data, and other data from: one or more of people, pets, livestock, dairy cows, cattle or other animals (e.g., one or more of farm animals, cattle, sheep, pigs, goats, horses, donkeys, mules, other animals, such as buffalo, oxen or camels, etc.); livestock diet and/or age; diseases; food borne illnesses, pathogen levels, and/or prevalence in farm manures or from livestock waste; optionally including as related to, or including, animal production (e.g., one or more of beef, dairy, poultry, swine, seafood), seed production, sugarcane production, tobacco production, fertilizer production, potato production, avocado production, vegetable production, grains production, corn production, wheat production, fruit & tree nuts production, rice production, soybean, olive, canola, grapeseed, sesame, and similar product, flour, and/or oil or crop production, cotton production, hay production, aquatic livestock or fish, and the like.

The apparatuses or methods optionally further include the use of unmanned surveillance vehicles, satellites or handheld devices for monitoring, collection, and/or analysis of EMFID data. The present developments optionally provide wherein an EMFID comprising device is used with or includes an unmanned aerial vehicle (e.g., an air, land, or sea drone, robot, or other vehicles optionally include audio, visual, or other input that is configured to monitor, collect, and/or analyze biometric data, transaction data, electronic payment data, location data, track movement data, logistics data, transportation data, and other data from: one or more of people, pets, livestock, dairy cows, cattle or other animals, (e.g., one or more of farm animals, cattle, sheep, pigs, goats, horses, donkeys, mules, other animals, such as buffalo, oxen or camels, etc.); for diagnosis of disease and treatment disease prevention, monitoring antibiotics, human health effects from drug use in food animals, producing greater quantity of commodities by fewer animals, monitor weight gain, monitor metabolism, pharmacological strategies to prevent or treat livestock, dairy cows, cattle or other animal diseases, monitor effects of vaccines and prophylactic medication to prevent or minimize infections, monitor antibiotics and parasiticides to treat active infection or prevent disease onset, monitor antibiotics and drugs uses with food-animal production, monitor antibiotics-resistant bacteria, monitor types of drugs used with food-animal production, eliminating subclinical populations of pathogenic microorganisms, monitoring drugs and hormones used for production enhancement, growth promotion and improved feed efficiency or monitoring growth-enhancing effect of antibiotics and the like.

Data to be monitored, collected, and/or analyzed can be transmitted, read, collected, sent, received, or stored using any suitable known device or method, e.g., but not limited to, radio, wifi, cellular (2G, 3G, 4G, 5G, or the like), scanners, barcode scanners, Bluetooth, ethernet, USB, magnetic, optical, or solid state storage or hard drives; holographic or optical storage devices, cables, infrared, and the like.

At least certain embodiments optionally relate to methods, apparatuses, non-transitory computer readable media, computer systems, networks, or systems using a wireless or EMF based device for detection or tracking of a user's data to provide data, non-limiting examples, including without limitation, (e.g., wearable banking wristbands, kitchen appliances, garments, fashion apparel, household items, internet things, remote controls, TVs, cabinets, walls, flooring, automobiles, radio clocks, electronics, wallets, digital wallets, transmitters, airport scanners, readers, printers, tags, smart labels, UHF passive RFID transceiver chips, inlays & labels, fixed & mobile readers, smartphones, mobile devices, blue tooth devices or other wireless devices, keys, currency, passport cards, enhanced drivers' license (EDL), barcodes, drugs, labels of products, chip vaccinations, clothing, merchandise, pharma/healthcare, products or other services or experiences, mobile coupons, electronic skin tattoos, electronic hologram EMFID tags, payment cards, student ID cards, corporate identification cards or integration of biometric EMFID cards, wireless biosensors, laptops, computers, PCs, and other devices, and the like) for one or more individuals for real-time tracking of EMFID communications, security, routing, analysis, storage, access, analysis, and/or retrieval. Non limiting uses can include one or more of vaccinations and/or embedded in any physical objects, including without limitation, drugs, labels of products, packaging, passports, credit cards, debit cards, payment systems, travel cards, edible tags, navigation systems, vehicle tags, clothes, merchandise, smart dust, mobile devices or other wireless devices, international mobile equipment identity (IMEI), other wireless or handheld devices, computers, PCs, currency, identification cards, products, services or experiences, microchips, nanobots, implants, and subdermal or other implants in animals and/or individuals.

The uses can include EMF or other tags that can be encrypted as electromagnetic frequency (EMF) identification (EMFID) technologies to provide data transfer and communications for EMFID sensors for automatic identification data collection of personal data for one or more individuals or end user, multiple EMFID tag communications, remotely storing, monitoring and retrieving data, location data and other data to develop a profile for one or more end user, pet, livestock, dairy cows, cattle or other animals, including tracking movement, logistics data, and/or location data using radio and other frequency tags and relaying data from EMFID tag interactions to a database that can be accessed by members of a network, physical, emotional and mental state data, integration of biometric data, healthcare, physical health conditions, medical conditions, track movement, logistics, transportation, track diseases for pets, livestock, dairy cows, cattle or other animals, diseases and conditions for disease control and prevention, monitoring antibiotics, pharmaceutical data and other data to develop a profile for one or more end user, pet, livestock, dairy cows, cattle or other animals, including tracking movement, logistics data, and/or location data using radio and other frequency tags and relaying data from EMFID tag interactions to a database that can be accessed by members of a network, and readers, GPS, RTLS location tracking and mapping location data and information to identify an item being tracked and to store data on a database, EMFID communications between customers and companies, patients, retailers, global brands, dairy farmers, milk production and dairy products or milk products, animal farming companies, cattle farmers, industrial livestock production companies, pharmaceutical companies, mapping location data and information, social media communications and human behavior and other information data for analytic measurements data mining, linking information on EMFID tags and databases that store privacy information and identification and personal data, EMFID communications between customers and companies, patients, retailers, global brands, dairy farmers, milk production and dairy products or milk products, animal farming companies, cattle farmers, industrial livestock production companies, pharmaceutical companies & products or other services or experiences or promotions, of medical care, drugs, products, illegal activity, or other services or past, present or future users, targets and/or target markets for companies, organizations, government agencies, financial institutions, global brands, dairy farmers, milk production and dairy products or milk products, animal farming companies, cattle farmers, industrial livestock production companies, pharmaceutical companies, merchants, retailers and the like, for products or other services or experiences or promotions, of interest of past, present or future customers, users, targets, and/or target markets, for companies, organizations, government agencies, financial institutions, global brands, dairy farmers, milk production and dairy products or milk products, animal farming companies, cattle farmers, industrial livestock production companies, pharmaceutical companies, merchants, retailers, and the like, by electronically collecting and analyzing, on a computer system, network or system using a wireless device for detection of EMFID tracking of personal data for one or more individuals or end user that uses processors, quantitative analytic measurements data mining of personal data for one or more individuals or end user, multiple EMFID tag communications, remotely storing, monitoring and retrieving data and transaction data, electronic payment data, location data, track movement data, logistics data, transportation data, physical, emotional and mental state data, integration of biometric data, healthcare, physical health conditions, medical conditions, track movement, logistics, transportation, track diseases for pets, livestock, dairy cows, cattle or other animals, diseases and conditions for disease control and prevention, monitoring antibiotics, pharmaceutical data, and other data to develop a profile for one or more end user, pet, livestock, dairy cows, cattle or other animals, including tracking movement, logistics data, and/or location data using radio and other frequency tags and relaying data from EMFID tag interactions on different codes and readers to a database that can be accessed by members of a network for real-time tracking of EMFID communications, security, routing, analysis, storage, access and retrieval using a wireless device for detection of EMFID tracking of personal data for one or more individuals or end user that uses a higher spectrum of light, sound and electromagnetic frequency (EMF) identification (EMFID) technologies for multiple EMFID tag communications and EMFID sensors for automatic identification data collection of personal data for one or more individuals or end user, multiple EMFID tag communications, remotely storing, monitoring and retrieving data and transaction data, electronic payment data, location data, track movement data, logistics data, transportation data, physical, emotional and mental state data, integration of biometric data, healthcare, physical health conditions, medical conditions, track movement, logistics, transportation, track diseases for pets, livestock, dairy cows, cattle or other animals, diseases and conditions for disease control and prevention, monitoring antibiotics, pharmaceutical data and other data to develop a profile for one or more end user, pet, livestock, dairy cows, cattle or other animals, including tracking movement, logistics data, and/or location data using radio and other frequency tags and relaying data from EMFID tag interactions to a database that can be accessed by members of a network, and readers, wherein predictive analytics are used for one or more individuals analysis, marketing, monitoring, behavior, location, track movement, diagnosis and promotions, of interest, of medical care, drugs, products, illegal activity, or other services, of interest, of past, present or future customers, users, targets and/or target markets.

At least certain embodiments optionally provide electromagnetic frequency (EMF) identification (EMFID) technologies to provide data transfer and communications for EMFID sensors for automatic identification data collection of user's data, multiple EMFID tag communications, remotely storing, monitoring and retrieving data and transaction data, electronic payment data, location data, track movement data, logistics data, transportation data, physical, emotional and mental state data, integration of biometric data, healthcare, physical health conditions, medical conditions, track movement, logistics, transportation, track diseases for pets, livestock, dairy cows, cattle or other animals, diseases and conditions for disease control and prevention, monitoring antibiotics, pharmaceutical data and other data to develop a profile for one or more end user, pet, livestock, dairy cows, cattle or other animals, including tracking movement, logistics data, and/or location data using radio and other frequency tags and relaying data from EMFID tag interactions on different codes and readers to a database that can be accessed by members of a network, and readers, scalar electromagnetic fields, radio frequency (RF) or Wi-Fi frequency ranges not current used, EMFID applicable hardware or software EMFID to provide data transfer and communications of data to develop a profile for one or more individuals for real-time tracking of EMFID communications, security, routing, analysis, storage, access, and retrieval.

At least certain embodiments optionally provide electromagnetic frequency (EMF) identification (EMFID) technologies to provide data transfer and communications for automatic identification data collection of user's data using nanotechnology and nanobiotechnology for the manipulation of matter on an atomic, molecular and supramolecular scale technologies and nanoparticles to perform functions such as targeted delivery, imaging or providing diagnostics and feedback/use/need for medicine for the detection, prevention and treatment of medical conditions, diseases and conditions for disease control and prevention that include communicable and infectious track movement, logistics, transportation, track diseases for pets, livestock, dairy cows, cattle or other animals, diseases and conditions for disease control and prevention, monitoring antibiotics, common medical illnesses and injuries, mental disorders, genetic disorders, skin track movement, logistics, transportation, track diseases for pets, livestock, dairy cows, cattle or other animals, diseases and conditions for disease control and prevention, monitoring antibiotics, blood disorders, lung track movement, logistics, transportation, track diseases for pets, livestock, dairy cows, cattle or other animals, diseases and conditions for disease control and prevention, monitoring antibiotics, metabolic diseases and conditions for disease control and prevention and other physical health conditions, including asthma, cancer, arthritis, diabetes, epilepsy, eating disorders, substance abuse, sexuality transmitted track movement, logistics, transportation, track diseases for pets, livestock, dairy cows, cattle or other animals, diseases and conditions for disease control and prevention, monitoring antibiotics, ailments associated with pregnancy and childhood using biosensors that remotely store, monitor and retrieve molecular data, physical, emotional and mental state data, emotions data, healthcare and pharmaceutical data and real-time tracking of nanobot interactions, location data and record movement of people, pets, livestock and objects and other data, wherein predictive analytics are used for one or more individuals analysis, marketing, monitoring, behavior, location, track movement, diagnosis and promotions, of interest, of medical care, drugs, products, illegal activity, or other services, of interest, of past, present or future customers, users, targets and/or target markets.

At least certain embodiments optionally provide electromagnetic frequency (EMF) identification (EMFID) technologies to provide data transfer and communications using EMFID sensors for automatic identification data collection of user's personal integration of biometric data, transaction data, electronic payment data, location data, track movement data, logistics data, transportation data, and biosensors that remotely store, monitor and retrieve molecular data, physical, emotional and mental state data, emotions data, healthcare and pharmaceutical data and real-time tracking of nanobot interactions, location data and record movements of people, pets, livestock and objects and other data, wherein predictive analytics are used for one or more individuals analysis, marketing, monitoring, behavior, location, track movement, diagnosis and promotions, of interest, of medical care, drugs, products, illegal activity, or other services, of interest, of past, present or future customers, users, targets and/or target markets.

For example, optionally, if a global brand or pharmaceutical chain has 26,000 locations worldwide wherein they are collecting, managing and providing real-time or near real-time relevant information processing on a computer system processor of the EMFID communications and personal data, EMFID communications between customers and companies, patients and pharmaceutical companies for products or other services or experiences or promotions, of interest via the Internet, communications, and social media content to electronically determine on a computer system or processor of data wherein predictive analytics are used for one or more individuals analysis, marketing, monitoring, behavior, location, diagnosis and promotions, of interest of medical care, drugs, cigarettes, EMFID labels of pharmaceutical products, electronic product code (EPC), EMFID inventory tracking, EMFID logistic applications, animal identification, Garment EMFID Inventory Management System (GIMS), EMFID chip vaccinations, packaging, products, illegal activity, or other services of past, present or future users, targets and/or target markets of occurrence of one or more topics in conjunction with consumer packaged goods, payment systems, EMFID NFC transactions, EPC tag communications, contactless RFID communications for products or other services or experiences, EMFID communications between customers and companies, patients and pharmaceutical companies & products or other services or experiences or promotions, of interest and relatedness of the one or more topics to consumer packaged goods, payment systems, EMFID NFC transactions, EPC tag communications, contactless RFID communications for products or other services or experiences, EMFID communications between customers and companies, patients and pharmaceutical companies & products or other services or experiences or promotions, of interest, in order to provide targeted, location-based promotions, of interest or offers, EMFID mapped, or EMFID tag communications to provide data transfer and communications for real-time tracking of EMFID communications, security, routing, analysis, storage, access and retrieval using a wireless device.

The EMFID can optionally be provided in a category from one or more online user online activity and/or social media sources, e.g., by electronically quantifying, on a computer system, network or system using a wireless device for detection of EMFID tracking of user's data that uses processors, the analyzed radio frequency location and identification data transfer to a database that can be accessed by members of a network for products or other services or experiences or promotions, of interest via the Internet, communications, and social media content, and electronically providing actionable wireless use of EMFID hardware or software, electromagnetic fields to provide data transfer for real-time tracking of EMFID communications, security, routing, analysis, storage, access and retrieval.

The actionable data and/or information can optionally include consumer sentiment expressed data of online internet activity and social media participants concerning consumer packaged goods, payment systems, EMFID NFC transactions, EPC tag communications, contactless RFID communications for products or other services or experiences, EMFID communications between customers and companies, patients, retailers, global brands, dairy farmers, milk production and dairy products or milk products, animal farming companies, cattle farmers, industrial livestock production companies, pharmaceutical companies & products or other services or experiences or promotions, of interest in, optionally in a category of interest, in order to identify objects, animals and/or human beings interact with a location using computer chip or EMFID microchip and/or nanobots, EMFID chips or subdermal implant that contains a unique ID number that can be linked to information and data contained in an external database, such as personal identification, medical history, electromagnetic field in conjunction with smartphones, mobile devices, blue tooth devices or other wireless devices, EMFID tags or multiple EMFID devices to provide targeted, location-based promotions, of interest or offers, EMFID mapped, or EMFID tag communications to provide data transfer and communications for tracking of EMFID communications, security, routing, analysis, storage, access and retrieval using a wireless device for detection of EMFID tracking of personal data for one or more individuals or end user.

The subject matter hereof can optionally provide in certain non-limiting aspects, electromagnetic frequency (EMF) identification (EMFID) technologies method, system or apparatus or non-transitory computer readable storage medium, comprising:

an electromagnetic frequency (EMF) identification (EMFID) method or device configured to provide, or providing data transfer, storage, analysis, and communications for EMFID sensors that provide automatic identification data collection and transfer, the method comprising:

(a) electronically assigning to an end user, on an electronic network computing system via a processor, a unique identifier for an EMFID tag device of the end user of a mobile or stationary computing device that transmits said data via said EMFID tag device or via said computing device; the data comprising:
  (i) personal data of at least one end user comprising data including personal identification data and four or more of:
    (A) product or service information accessed by or assigned to the end user;
    (B) end user: biometric, healthcare, health or medical condition, pharmaceutical prescription or use, or electronic medical record (EMF), other data;
    (C) end user: personal or profile information,
    (D) content, dosing, recipient, physician, hospital, insurance, pharma/healthcare or other service provider information, product manufacturing or logistics data, financial or sales information, manufacturing, farming, animal farming, industrial livestock production, location, web browsing, or tracking information, GPS, RTLS, travel, currency, monitoring, or personal identification, information of the user, products or services;
    (E) biometric data, transaction data, electronic payment data, location data, track movement data, logistics data, transportation data, and
  (ii) EMFID tag communications data comprising:
    (A) at least a portion of said personal data;
    (B) communications data between two or more parties or end user, pet, livestock, dairy cows, cattle or other animal including the use of said EMFID tag device, user data, and communications data selected from three or more of communications data of customers, companies, patients, retailers, global brands, dairy farmers, milk production and dairy products or milk products, animal farming companies, cattle farmers, industrial livestock production companies, pharmaceutical companies; the communications data further comprising at least two or more of information about promotions, of interest for products or services via the Internet, communications, and social media content; the assigning including the identifier assigned to the user or the client mobile device or computer;
(b) electronically receiving a request from said user for said data, through a client application operating on the client mobile device or computer, using non-transitory computer readable media and the EMFID tag device having data collection sensors, the data provided in a combination of two or more EMF frequencies, wavelengths, types, fields, packets, photons, patterns, standing or dynamic, bidirectional or multidirectional, scalar elements, and ranges or combinations thereof;
(c) electronically providing to said user, a customized EMFID tracking tag device analytics platform for providing three or more of analytics measurements, data mining, linking information on one or more of the EMFID tag devices and databases that store said data for one or more of customers, users, targets, and/or target markets, for one or more of companies, organizations, government agencies, financial institutions, global brands, dairy farmers, milk production and dairy products or milk products, animal farming companies, cattle farmers, industrial livestock production companies, pharmaceutical companies, merchants, retailers, and law enforcement; by electronically collecting and analyzing, on a computer system, network or system using a wireless device for detection of EMFID tracking of one of more of the EMFID tag device user's data as said data that can be accessed by members of a network of EMFID tag device transmitters, airport scanners, for social media communications, and online communications and activity are selected based on the data.

The method device optionally further comprises, or is configured to, provide wherein:
(a) said one or more of said unmanned surveillance vehicles, satellites or hand-held devices is selected from an air, land, or sea drone, a robot, or other mobile surveillance device;
(b) said one or more of said unmanned surveillance vehicles, satellites or hand-held devices comprises audio, visual, or EMF input device that is configured to monitor, collect, and/or analyze biometric data, transaction data, electronic payment data, location data, track movement data, logistics data, transportation data, and other data from said user as part of said EMFID tag communications data;
(c) said EMFID tag communications data further comprises one or more of monitored, collected, and/or analyzed biometric data, transaction data, electronic payment data, location data, track movement data, logistics data, transportation data, of people, pets, livestock, dairy cows, cattle or other animals, livestock diet and/or age; diseases; food borne illnesses, pathogen levels and/or prevalences in farm manures or from livestock waste;
(d) said EMFID tag communications data further comprises one or more of monitored, collected, and/or analyzed biometric data, transaction data, electronic payment data, location data, track movement data, logistics data, transportation data, further including data related to, or including, animal production, seed production, agricultural plant production, edible oil production, animal feed production, or aquatic livestock or fish production; and
(e) said EMFID tag communications data that is monitored, collected, and/or analyzed is transmitted, read, collected, sent, received, or stored using one or more selected from one or more selected from radio, wifi, cellular, scanners, barcode scanners, Bluetooth, ethernet, USB, magnetic, optical, or solid state storage or hard drives; holographic or optical storage devices, cables, infrared, and data transferred using one or more EMF frequencies.
(f) said EMFID tag communication data for diagnosis of disease and treatment disease prevention, monitoring antibiotics, human health effects from drug use in food animals, producing greater quantity of commodities by fewer animals, monitor weight gain, monitor metabolism, pharmacological strategies to prevent or treat livestock, dairy cows, cattle or other animal diseases, monitor effects of vaccines and prophylactic medication to prevent or minimize infections, monitor antibiotics and parasiticides to treat active infection or prevent disease onset, monitor antibiotics and drugs uses with food-animal production, monitor antibiotics-resistant bacteria, monitor types of drugs used with food-animal production, eliminating subclinical populations of pathogenic microorganisms, monitoring drugs and hormones used for production enhancement, growth promotion and improved feed efficiency or monitoring growth-enhancing effect of antibiotics and the like.

The method device optionally further comprises, or is configured to, provide:

(d) electronically providing, on a computer system, network or system, tracking of user's data to provide data transfer for real-time tracking of EMFID communications, security, routing, analysis, storage, access and retrieval, wherein analysis data is generated or retrieved based on real-time measurements, track movement, logistics data, and/or transaction data, electronic payment data, location data, track movement data, logistics data, transportation data, or data collection and management of one or more of:

(i) the consumer or brand sentiment expressed data by the online internet activity and social media participants concerning consumer packaged goods, payment systems, EMFID NFC transactions, EPC tag communications, contactless RFID communications for products or other services or experiences, EMFID communications between customers and companies, patients, retailers, global brands, dairy farmers, milk production and dairy products or milk products, animal farming companies, cattle farmers, industrial livestock production companies, pharmaceutical companies & products or other services or experiences or promotions, of interest; electronically compared and analyzed on a computer system optionally with one or more of:

(ii) historical data representing quantitative measurements of the consumer or brand sentiment data concerning consumer packaged goods, payment systems, EMFID NFC transactions, EPC tag communications, contactless RFID communications for products or other services or experiences, EMFID communications between customers and companies, patients, retailers, global brands, dairy farmers, milk production and dairy products or milk products, animal farming companies, cattle farmers, industrial livestock production companies, pharmaceutical companies & products or other services or experiences or promotions, of interest in the past or concurrently with similar or competing products and services, of interest, of past, present or future customers, users, targets and/or target markets; and, optionally, (e) electronically providing, on a computer system, network or system, tracking of user's data to provide data transfer for real-time tracking of EMFID communications, security, routing, analysis, storage, access and retrieval, wherein analysis data is generated or retrieved based on real-time measurements, track movement, logistics data, and/or transaction data, electronic payment data, location data, track movement data, logistics data, transportation data, or data collection and/or optionally management of one or more of:

(i) the consumer or brand sentiment expressed data by the online internet activity and social media participants concerning consumer packaged goods, payment systems, EMFID NFC transactions, EPC tag communications, contactless RFID communications for products or other services or experiences, EMFID communications between customers and companies, patients, retailers, global brands, dairy farmers, milk production and dairy products or milk products, animal farming companies, cattle farmers, industrial livestock production companies, pharmaceutical companies & products or other services or experiences or promotions, of interest; electronically compared and analyzed on a computer system optionally with one or more of:

(ii) historical data representing quantitative measurements of the consumer or brand sentiment data concerning consumer packaged goods, payment systems, EMFID NFC transactions, EPC tag communications, contactless RFID communications for products or other services or experiences, EMFID communications between customers and companies, patients, retailers, global brands, dairy farmers, milk production and dairy products or milk products, animal farming companies, cattle farmers, industrial livestock production companies, pharmaceutical companies & products or other services or experiences or promotions, of interest in the past or concurrently with similar or competing products and services, of interest, of past, present or future customers, users, targets and/or target markets.

The developments hereof can optionally further provide wherein the qualitative or quantitative user's data, and/or EMFID communications between customers and companies, patients and pharmaceutical companies for products or other services or experiences or promotions, of interest via the Internet, communications, and social media content, includes one or more selected from the group consisting of messages posted to online social media websites, Internet messages; social media postings; online dialog; blogging; EMFID communications between customers and companies, patients, retailers, global brands, dairy farmers, milk production and dairy products or milk products, animal farming companies, cattle farmers, industrial livestock production companies, pharmaceutical companies; call center logs; emails; online mail and fax communications; call center records; online purchasing information; online warranty claims; and other online traffic.

The developments hereof can optionally further provide wherein the one or more online user online activity and social media sources include one or more selected from the group consisting of blogs and sub-blogs; online discussion forums; social networks; wiki sites; online reviews on e-commerce sites; video websites; micro-blogging services; call centers; websites including websites of companies; and other sources of online activity, communications, and social media content.

The developments hereof can optionally further provide wherein said electronically determining the consumer or brand sentiment rating data sets includes one or more of:

(i) electronically identifying, using a computer system processor, data sets comprising terms or phrases of interest associated with consumer packaged goods, payment systems, EMFID NFC transactions, EPC tag communications, contactless RFID communications for products or other services or experiences, EMFID communications between customers and companies, patients, retailers, global brands, dairy farmers, milk production and dairy products or milk products, animal farming companies, cattle farmers, industrial livestock production companies, pharmaceutical companies & products or other services or experiences or promotions, of interest in one or more of the online activity, communications, and social media content data sets;

(ii) electronically searching on a computer system processor in a set of closest N words from the terms or phrases of interest for keywords expressing consumer or brand sentiment about the terms or phrases of interest;

(iii) electronically assigning using a computer system processor, a probability value data set for one or more of the keywords, the probability value indicating the probability that the keyword suggests something positive or negative about the terms or phrases of interest;

(iv) electronically assigning using a computer system processor one or more occurrences of the terms or phrases of interest with a consumer or brand sentiment score data value based on the keywords in the set of closest N words from the terms or phrases of interest; and/or (v) electronically summing using a computer system processor one or more consumer or brand sentiment score assigned to each of the terms or phrases of interest in each social media conversation to electronically obtain using computer system processor consumer or brand sentiment rating data sets concerning consumer packaged goods, payment systems, EMFID NFC transactions, EPC tag communications, contactless RFID communications for products or other services or experiences, EMFID communications between customers and companies, patients, retailers, global brands, dairy farmers, milk production and dairy products or milk products, animal farming companies, cattle farmers, industrial livestock production companies, pharmaceutical companies & products or other services or experiences or promotions, of interest.

The developments hereof can optionally further provide wherein the consumer or brand sentiment score is based on one or more of: how many times each occurrence of the terms or phrases of interest appears in the social media conversation; number of keywords expressing consumer or brand sentiment about the terms or phrases of interest in the set of closest words; whether each keyword reflects a positive, negative or neutral consumer or brand sentiment about consumer packaged goods, payment systems, EMFID NFC transactions, EPC tag communications, contactless RFID communications for products or other services or experiences, EMFID communications between customers and companies, patients, retailers, global brands, dairy farmers, milk production and dairy products or milk products, animal farming companies, cattle farmers, industrial livestock production companies, pharmaceutical companies & products or other services or experiences or promotions, of interest; and relevance of the keywords expressing consumer or brand sentiment about the terms or phrases of interest, in order to provide targeted, location-based promotions, of interest or offers. The developments can optionally further provide wherein the relevance of the keywords is electronically determined by using a computer system one or more of: linguistic modifiers of the keywords expressing consumer or brand sentiment about the terms or phrases of interest including one or more of negations, comparatives, and enumerations; and proximity of the keywords to the terms or phrases of interest in the online social media conversation.

The developments hereof can optionally further provide further comprising electronically analyzing and using online social media author and website influence parameter data on a computer system in classifying the consumer or brand sentiment of consumer online activity, behavior, location, diagnosis or social media conversations or content data.

The developments hereof can optionally further provide further comprising one or more of: calculating how the consumer or brand sentiment concerning consumer packaged goods, payment systems, EMFID NFC transactions, EPC tag communications, contactless RFID communications for products or other services or experiences, EMFID communications between customers and companies, or experiences or promotions, of interest trends over time; calculating how the consumer or brand sentiment concerning consumer packaged goods, payment systems, EMFID NFC transactions, EPC tag communications, contactless RFID communications for products or other services or experiences, EMFID communications between customers and companies, patients, retailers, global brands, dairy farmers, milk production and dairy products or milk products, animal farming companies, cattle farmers, industrial livestock production companies, pharmaceutical companies & products or other services or experiences or promotions, of interest varies by online source or group of sources; and calculating how the consumer or brand sentiment concerning consumer packaged goods, payment systems, EMFID NFC transactions, EPC tag communications, contactless RFID communications for products or other services or experiences, EMFID communications between customers and companies, patients, retailers, global brands, dairy farmers, milk production and dairy products or milk products, animal farming companies, cattle farmers, industrial livestock production companies, pharmaceutical companies & products or other services or experiences or promotions, of interest concurrently trends over time and varies by online source or group of sources.

The developments hereof can optionally further provide determining electromagnetic frequency (EMF) identification, as the broadest term, which includes Radio waves; Infrared; Ultraviolet; and Soft X-rays (Freq./Wavelength), that can be used for communication as: Radio waves: ELF to EHF: Extremely Low Frequency (ELF: 3 Hz/100 Mm); SuperLF: (30 Hz/10 Mm); UltaLF (voice) (300 Hz/1 Mm); (very low frequency (VLF) as (3 kHz/100 km), LF (30 kHz/10 km); Medium Freq (300 kHz/1 km); HighF (3 MHz/100 m); VeryHF (30 MHz/10 m); UltraHF (300 MHz/1 m); Microwaves are SHF and EHF of radio waves (SuperHF (3 GHz/1 dm); ExtremelyHF (30 GHz/1 cm); Terahertz radiation is between Microwaves and Far IR: (100-10,000 GHz/3 cm-1 mm); then: Infrared (IR): Far IR (300 GHz/1 mm); Mid IR (3 THz/100 microM); Near IR: (30 Hz/10 microM); (Note Visible Light is 400-700 nm wavelength) between IF and UV; Ultraviolet (UV): NearUV (300 THz/1 microM); ExtremeUV (3 PHz/100 nm); Soft X-rays (30 PHz/10 nm) to (3 EHz/100 pm); Low Frequency (LF); High Frequency (HF); and Ultra High Frequency (UHF).

The developments hereof can optionally further provide determining an overall volume of the radio frequency location and identification data transfer to a database that can be accessed by members of a network for products or other services or experiences or promotions, of interest via the Internet, communications, and social media content and data transfer to a database that can be accessed by members of a network for products or other services or experiences or promotions via the Internet, communications, and social media content per unit of time.

The developments hereof can optionally further provide determining how the overall volume of online social conversations referring to consumer packaged goods, payment systems, EMFID NFC transactions, EPC tag communications, contactless RFID communications for products or other services or experiences, EMFID communications between customers and companies, patients, retailers, global brands, dairy farmers, milk production and dairy products or milk products, animal farming companies, cattle farmers, industrial livestock production companies, pharmaceutical companies & products or other services or experiences or promotions, of interest trends over time.

The developments hereof can optionally further provide determining a share of online voice acquired by consumer packaged goods, payment systems, EMFID NFC transactions, EPC tag communications, contactless RFID communications for products or other services or experiences, EMFID communications between customers and companies, patients, retailers, global brands, dairy farmers, milk production and dairy products or milk products, animal farming companies, cattle farmers, industrial livestock production companies, pharmaceutical companies & products or other services or experiences or promotions, of interest with respect to other (EMFID) system using a wireless device for detection of EMFID tracking of personal data for one or more individuals or end user that uses subject matter.

The developments hereof can optionally further provide wherein the other online social media subject matter includes subject matter associated with competitors in the category, in order to provide targeted, location-based promotions, of interest or offers.

The developments hereof can optionally further provide electronically calculating on a computer system processor one or more of: how the share of online voice acquired by consumer packaged goods, payment systems, EMFID NFC transactions, EPC tag communications, contactless RFID communications for products or other services or experiences, EMFID communications between customers and companies, patients, retailers, global brands, dairy farmers, milk production and dairy products or milk products, animal farming companies, cattle farmers, industrial livestock production companies, pharmaceutical companies & products or other services or experiences or promotions, of interest trends over time; and how the share of online voice acquired by consumer packaged goods, payment systems, EMFID NFC transactions, EPC tag communications, contactless RFID communications for products or other services or experiences, EMFID communications between customers and companies, patients, retailers, global brands, dairy farmers, milk production and dairy products or milk products, animal farming companies, cattle farmers, industrial livestock production companies, pharmaceutical companies & products or other services or experiences or promotions, of interest trends over time with respect to the subject matter of the competitors in the category, in order to provide targeted, location-based promotions, of interest or offers.

The developments hereof can optionally further include wherein said selection comprises electronically collecting and analyzing behavior information of said user, said behavior information comprising one or more selected from: (a) said EMFID tag communications tracking and analysis; (b) said location information; (c) said mapping location data and information; (d) said user internet activity; and (e) said social networking communications.

The developments hereof can optionally further include wherein said location-based promotions, of interest or offers, customized information, social media content, promotions or offers are selected from the group consisting of a coupon, an advertisement, a location-based promotion, a location-based offer, a location-based discount, a daily deal ad, location-based advertising, a location-based ad, a location-based deal or offer, a mobile ads, a mobile ad network, mobile advertising, mobile location-based advertising, a customer loyalty card, a discounts, a promotion, an offer, a location-based promotion, an online or mobile coupon or promotion, mobile location-based advertising, a promotions or offers associated with a location or a map in a social network or website online or mobile device, a location-based mobile coupon, a mobile grocery coupon, a mobile ad products, a targeted mobile ad, a mobile advertising network, and a mobile coupon.

The developments hereof can optionally further include wherein said mobile device or wireless device is selected from the group consisting of a smart phone, a tablet device, a cell phone, a mobile internet device, a netbook, a notebook, a personal digital assistant, an internet phone, a holographic device, a holographic phone, a cable internet device, a satellite internet device, an internet television, a DSL internet device, and a portable internet access device or computer.

The developments hereof can optionally further include wherein said information, social media content, promotions or offers comprise or are displayed as one selected from EMFID tag interactions for one or more individuals for marketing and mapping relationships between members of a social network or website, social networking websites, or third party websites or applications.

The developments hereof can optionally further include wherein said third party is selected from a government agency, a credit reporting agency, a social network, a website, a service provider, an auction site, a company, an educational or financial institution, bank, a lender or mortgage company, an auto company, or a regulatory agency according to applicable laws and regulations.

The developments hereof can optionally further include wherein said company is selected from the group consisting of a financial services company, a product company, a services company, a social network, a website, a service provider, an auction site, a company, a brand merchant or retailer, a real estate company or related services, an educational or financial institution or bank, an entertainment company, an online penny or online auction, or other type of service company.

The developments hereof can optionally further include wherein said method further comprises providing said first promotional data sets to one selected from the group consisting of said end users, said members, other end users or members, advertisers, third parties; and wherein said EMFID tag communications include social EMFID tag communications.

The developments hereof can optionally further include selecting a third company/brand/social/global EMFID tag interactions category for a second position of the company/brand/social/global EMFID tag interactions promotional data set, where the third company/brand/social/global EMFID tag interactions category is varying from the one or more identified second company/brand/social/global EMFID tag interactions categories.

The developments hereof can optionally further include wherein: the company/brand/social/global EMFID tag interactions promotional data set is associated with a web page; and the company/brand/social/global EMFID tag interactions categories are ordered by capturing, processing, analyzing and filtering relevance, social content marketing, social contextual ads and connections among said users, members, or their friends, family, acquaintances, classmates, or business associates; user-contributed information, mood recording EMFID tag communications & updating, friend communications and blog EMFID tag communications and focused marketing and those communications are used to select targeted location-based promotions, location-based offers, location-based coupons, information, social media content, promotions or offers in connection with an online EMFID tag or mobile EMFID tag for the user or member of a social network or website, and connecting them with the brand or advertiser to the web page.

The developments hereof can optionally further include wherein identifying one or more second company/brand/social/global EMFID tag interactions categories using one or more correlation criteria further comprises: identifying one or more company/brand/social/global EMFID tag interactions categories having a correlation measure that is less than a correlation threshold.

The developments hereof can optionally further include wherein at least one second company/brand/social/global EMFID tag interactions category has a separate correlation measure for at least one pair-wise combination of a category identifier associated with the at least one second company/brand/social/global EMFID tag interactions category and a category identifier associated with the first company/brand/social/global EMFID tag interactions category.

The developments hereof can optionally further include wherein said access is subject to identity verification.

The developments hereof can optionally further include wherein social networking is provided as one selected from social shopping, social networking communications, access to social networking websites or third party websites or applications, social plugins, social or business applications, SSLs, cookie and mobile cookie, browser cookie, advertising cookie, cookie-based targeting, flash cookie, location-based cookie and other third party cookie, and embedded in any physical objects, including without limitation, EMFID edible drugs, Medical EMFID card with prescription, EMFID labels of pharmaceutical products, electronic product code (EPC), EMFID inventory tracking, EMFID logistic applications, animal identification, Garment EMFID Inventory Management System (GIMS), EMFID chip vaccinations, EMFID packaging, EMFID passports, EMFID credit cards, EMFID debit cards, other forms of EMFID payment systems, EMFID travel cards, edible EMFID tags, EMFID navigation systems, EMFID vehicle tags, EMFID retail, EMFID clothing, EMFID pharma/healthcare, EMFID merchandise, EMFID smart dust, EMFID mobile devices, EMFID wireless devices, EMFID international mobile equipment identity (IMEI), other EMFID wireless or EMFID handheld devices, computers, PCs, currency, identification cards, products or other services or experiences and/or implanted subdermal advertisements.

DETAILED DESCRIPTION

Figure 1:
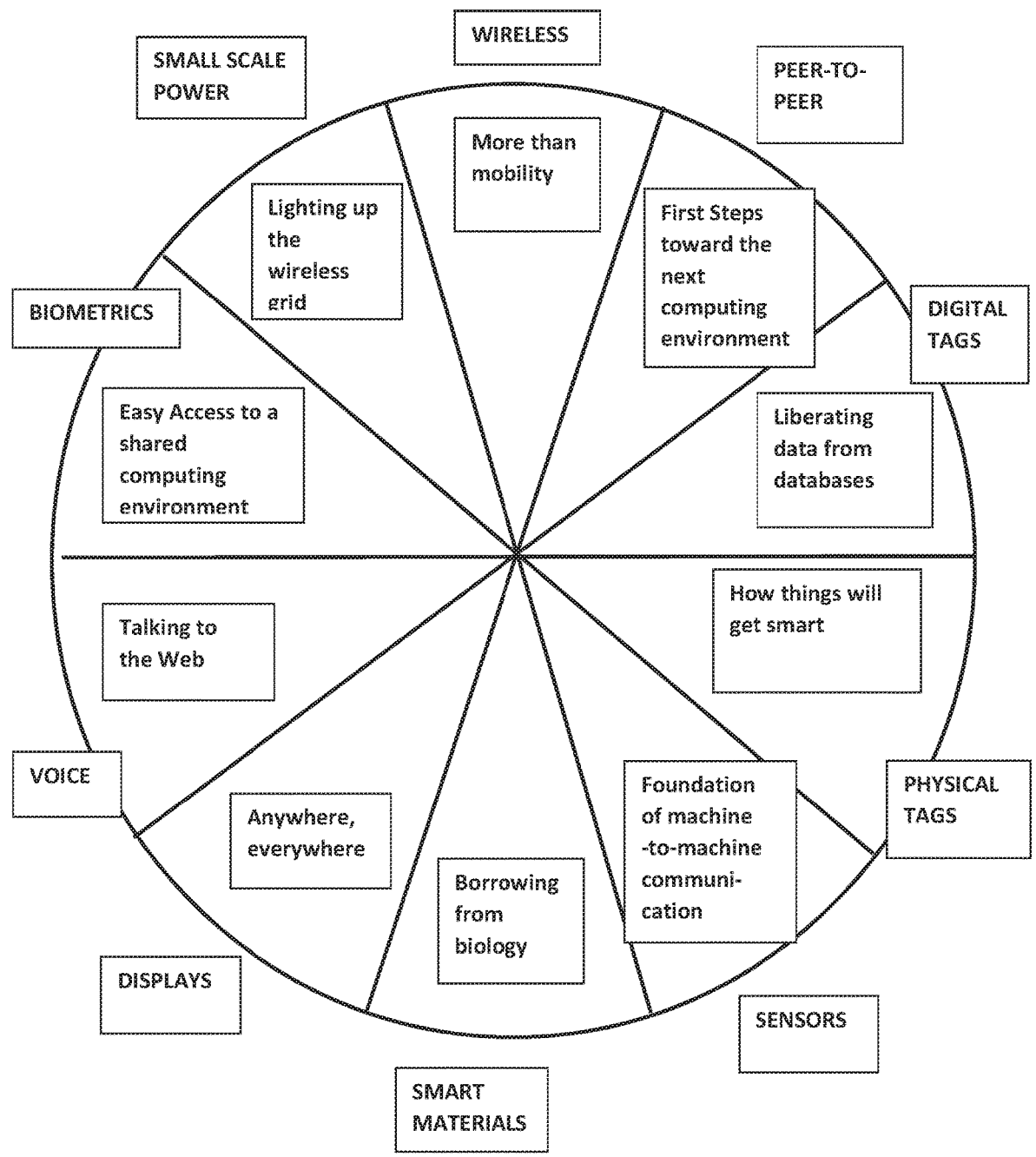
FIG. 1 is pie chart showing non-limiting examples of types and uses for EMFID tags and devices.
Figure 2:
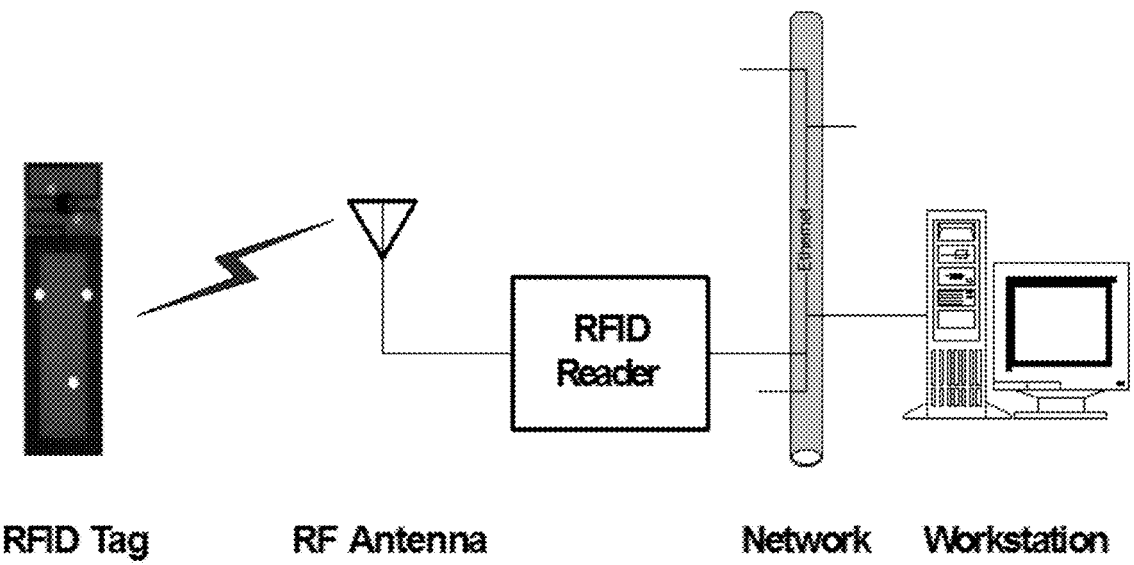
FIG. 2 is a schematic diagram of an RFID system and components including the RFID tag, RF antenna, RFID reader device; network, and computer workstation.

The present developments relate to methods, apparatus, non-transitory computer readable storage media, computer systems, networks, and/or systems using a wireless device for detection and tracking of user's data that uses electromagnetic frequency (EMF) identification (EMFID) technologies to provide data transfer and communications for EMFID sensors for automatic identification data collection of personal data for one or more individuals or end user, multiple EMFID tag interactions, remotely storing, monitoring and retrieving data and transaction data, electronic payment data, location data, track movement data, logistics data, transportation data, physical, emotional and mental state data, integration of biometric data, healthcare, physical health conditions, medical conditions, track movement, logistics, transportation, track diseases for pets, livestock, dairy cows, cattle or other animals, diseases and conditions for disease control and prevention, monitoring antibiotics, pharmaceutical data and other data to develop a profile for one or more end user, pet, livestock, dairy cows, cattle or other animals, including tracking movement, logistics data, and/or location data using radio and other frequency tags and relaying data from EMFID tag interactions to a database that can be accessed by members of a network, wherein predictive analytics are used for one or more individuals analysis, marketing, monitoring, behavior, location, track movement, diagnosis and promotions, of medical care, drugs, products, illegal activity, or other services, of interest, of past, present or future customers, users, targets and/or target markets.

The apparatuses or methods optionally further include the use of unmanned surveillance vehicles, satellites or handheld devices for monitoring, collection, and/or analysis of EMFID data. The present developments optionally provide wherein an EMFID comprising device is used with or includes an unmanned aerial vehicle (e.g., an air, land, or sea drone, robot, or other vehicles optionally include audio, visual, or other input that is configured to monitor, collect, and/or analyze biometric data, transaction data, electronic payment data, location data, track movement data, logistics data, transportation data, and other data from: one or more of people, pets, livestock, dairy cows, cattle or other animals, (e.g., one or more of farm animals, cattle, sheep, pigs, goats, horses, donkeys, mules, other animals, such as buffalo, oxen or camels, etc.); livestock diet and/or age; diseases; food borne illnesses, pathogen levels, and/or prevalence in farm manures or from livestock waste; optionally including as related to, or including, animal production (e.g., one or more of beef, dairy, poultry, swine, seafood), seed production, sugarcane production, tobacco production, fertilizer production, potato production, avocado production, vegetable production, grains production, corn production, wheat production, fruit & tree nuts production, rice production, soybean, olive, canola, grapeseed, sesame, and similar product, flour, and/or oil or crop production, cotton production, hay production, aquatic livestock or fish, and the like.

The apparatuses or methods optionally further includes the use of unmanned surveillance vehicles, satellites or hand-held devices for monitoring, collection, and/or analysis of EMFID data. The present developments optionally provide wherein an EMFID comprising device is used with or includes an unmanned aerial vehicle (e.g., an air, land, or sea drone, robot, or other vehicles optionally include audio, visual, or other input that is configured to monitor, collect, and/or analyze biometric data, transaction data, electronic payment data, location data, track movement data, logistics data, transportation data, and other data from: one or more of people, pets, livestock, dairy cows, cattle or other animals, (e.g., one or more of farm animals, cattle, sheep, pigs, goats, horses, donkeys, mules, other animals, such as buffalo, oxen or camels, etc.); for diagnosis of disease and treatment disease prevention, monitoring antibiotics, human health effects from drug use in food animals, producing greater quantity of commodities by fewer animals, monitor weight gain, monitor metabolism, pharmacological strategies to prevent or treat livestock, dairy cows, cattle or other animal diseases, monitor effects of vaccines and prophylactic medication to prevent or minimize infections, monitor antibiotics and parasiticides to treat active infection or prevent disease onset, monitor antibiotics and drugs uses with food-animal production, monitor antibiotics-resistant bacteria, monitor types of drugs used with food-animal production, eliminating subclinical populations of pathogenic microorganisms, monitoring drugs and hormones used for production enhancement, growth promotion and improved feed efficiency or monitoring growth-enhancing effect of antibiotics and the like.

Data to be monitored, collected, and/or analyzed can be transmitted, read, collected, sent, received, or stored using any suitable known device or method, e.g., but not limited to, radio, wifi, cellular (2G, 3G, 4G, 5G, or the like), scanners, barcode scanners, Bluetooth, ethernet, USB, magnetic, optical, or solid state storage or hard drives; holographic or optical storage devices, cables, infrared, and the like One or more embodiments can include the use of one or more data collection, storage, communication, and/or analysis, or protection therefrom, using an EMFID, such as an EMFID, transmitter, receivers or transceivers, that can be provided in any form and can include one or more of EMF frequencies, wavelengths, types, fields, packets, photons, patterns, standing or dynamic, bidirectional or multidirectional, scalar elements, and/or ranges or combinations thereof, to provide data transfer to one or more EMFID tag data recording, storage, communication, analysis, transfer, or other uses, such as, but not limited to components, compounds, compositions, EMF emissions, or data relating to one or more of product labeling (e.g., pharmaceutical products), encoded or deliverable compounds compositions or EMF emissions, e.g., but not limited to one or more of vaccinations, edible or administrable drugs, compounds or compositions, product labels, ID, content, dosing, recipient, physician, hospital, insurance, pharma/healthcare or other service provider, lot, dates, financial or sales information, manufacturing, farming, animal farming, industrial livestock production, tracking, GPS, RTLS, travel, currency, monitoring, or other ID information of products or services and/or microchip and/or nanobots implantable in or administered to animals and/or individuals. The actionable wireless use of electromagnetic fields, radio frequency (RF) or Wi-Fi frequency ranges EMFID, EMFID hardware or software EMFID, electromagnetic fields EMFID to provide data transfer for real-time tracking of EMFID communications, security, routing, analysis, storage, access and retrieval using a wireless device for detection of EMFID tracking of personal data for one or more individuals or end user that uses a higher spectrum of light, sound and electromagnetic frequency (EMF) identification (EMFID) technologies for multiple EMFID tag communications enabled objects, EMFID labels of pharmaceutical products, electronic product code (EPC), EMFID inventory tracking, EMFID logistic applications, animal identification, Garment EMFID Inventory Management System (GIMS), EMFID chip vaccinations and/or embedded in any physical objects, including without limitation, EMFID edible drugs, Medical EMFID card with prescription, EMFID labels of pharmaceutical products, electronic product code (EPC), EMFID inventory tracking, EMFID logistic applications, animal identification, Garment EMFID Inventory Management System (GIMS), EMFID chip vaccinations, EMFID packaging, EMFID passports, EMFID credit cards, EMFID debit cards, other forms of EMFID payment systems, EMFID travel cards, edible EMFID tags, EMFID navigation systems, EMFID vehicle tags, EMFID retail, EMFID clothing, EMFID pharma/healthcare, EMFID merchandise, EMFID smart dust, EMFID mobile devices, EMFID wireless devices, EMFID international mobile equipment identity (IMEI), other EMFID wireless or EMFID handheld devices, computers, PCs, currency, identification cards, products or other services or experiences and/or EMFID microchip and/or nanobots implant subdermal in animals and/or individuals using EMFID tags electromagnetic frequency (EMF) identification (EMFID) technologies to provide data transfer and communications for EMFID sensors for automatic identification data collection of personal data for one or more individuals or end user, multiple EMFID tag communications, remotely storing, monitoring and retrieving data, location data and other data to develop a profile for one or more end user, pet, livestock, dairy cows, cattle or other animals, including tracking movement, logistics data, and/or location data using radio and other frequency tags and relaying data from EMFID tag interactions on different codes and readers to a database that can be accessed by members of a network, physical, emotional and mental state data, integration of biometric data, healthcare, physical health conditions, medical conditions, track movement, logistics, transportation, track diseases for pets, livestock, dairy cows, cattle or other animals, diseases and conditions for disease control and prevention, monitoring antibiotics, pharmaceutical data and other data to develop a profile for one or more end user, pet, livestock, dairy cows, cattle or other animals, including tracking movement, logistics data, and/or location data using radio and other frequency tags and relaying data from EMFID tag interactions to a database that can be accessed by members of a network, and readers, GPS, RTLS location tracking and mapping location data and information to identify an item being tracked and to store data on a database, EMFID communications between customers and companies, patients, retailers, global brands, dairy farmers, milk production and dairy products or milk products, animal farming companies, cattle farmers, industrial livestock production companies, pharmaceutical companies, mapping location data and information, social media communications and human behavior and other products or other services or experiences and other data, tracking may also be retrieved based on historical data representing quantitative measurements of the consumer or brand sentiment expressed data among online internet activity and social media participants in the past.

Embodiments also optionally assign a consumer or brand sentiment rating to each of the radio frequency location and identification data transfer to a database that can be accessed by members of a network for products or other services or experiences or promotions via the Internet, communications, and social media content referring to consumer packaged goods, payment systems, EMFID NFC transactions, EPC tag communications, contactless RFID communications for products or other services or experiences, EMFID communications between customers and companies, patients, retailers, global brands, dairy farmers, milk production and dairy products or milk products, animal farming companies, cattle farmers, industrial livestock production companies, pharmaceutical companies & products or other services or experiences or promotions, of interest, in order to provide targeted, location-based promotions or offers, EMFID mapped, or EMFID tag communications to provide data transfer and communications for tracking of EMFID communications, security, routing, analysis, storage, access and retrieval using a wireless device for detection of EMFID tracking of personal data for one or more individuals or end user.

Embodiments optionally can present one or more aspects of analytics measurements data mining, linking information on EMFID tags and databases that store privacy information and identification for products or other services or experiences or promotions, or experiences or promotions, optionally provided via the Internet, communications, and social media content, optionally displayed or communicated electronically and/or in a graphical user interface (GUI), optionally in an intuitive and/or user-friendly manner at varying levels of detail, levels, layers, and/or granularity that optionally provides, enables, displays or communicates one or more aspects of the quantified radio frequency location and identification data transfer to a database that can be accessed by members of a network for products or other services or experiences or promotions, optionally grouped, organized, and/or filtered in a one or more of default and/or customizable presentations or displays.

In one embodiment, the user interface or GUI is a mobile, web-based or cloud-based service or product. In alternative embodiments, the user interface or GUI can optionally be provided as a mobile or cloud based browser-based interface hosted by a behind-the-firewall hardware or software.

Definitions:

Agriculture is the cultivation and breeding of animals, plants and fungi for food, fiber, biofuel, medicinal plants and other products used to sustain and enhance human life.

Automatic Identification Technology (AIT) is powerful technologies and devices that capture, aggregate, and transfer data to automated information systems (AIS). AIT reduces administrative and logistics costs in a wide variety of applications by increasing data accuracy (eliminating errors), speeding the collection and transmission of data, and making the entire data entry/collection process more efficient.

Automatic Identification Data Capture (AIDC) refers to the methods of automatically identifying objects, collecting data about them, and entering that data directly into computer systems (i.e. without human involvement). Technologies typically considered as part of AIDC include barcodes, Radio Frequency Identification (RFID), biometrics, magnetic stripes, Optical Character Recognition (OCR), smart cards, and voice recognition. AIDC is also commonly referred to as "Automatic Identification," "Auto-ID," and "Automatic Data Capture." AIDC is the process or means of obtaining external data, particularly through analysis of images, sounds or videos. To capture data, a transducer is employed which converts the actual image or a sound into a digital file. The file is then stored and at a later time it can be analyzed by a computer, or compared with other files in a database to verify identity or to provide authorization to enter a secured system. Capturing of data can be done in various ways; the best method depends on application. AIDC also refers to the methods of recognizing objects, getting information about them and entering that data or feeding it directly into computer systems without any human involvement. Automatic identification data capture technologies include barcodes, RFID, bokodes, OCR, magnetic stripes, smart cards and biometrics (like iris and facial recognition system). In biometric security systems, capture is the acquisition of or the process of acquiring and identifying characteristics such as finger image, palm image, facial image, iris print or voice print which involves audio data and the rest all involves video data. Radio frequency identification (RFID) is relatively a new AIDC technology, which was first developed in 1980's. The technology acts as a base in automatic identification data collection, identification and analysis systems worldwide. RFID has found its importance in a wide range of markets including livestock identification and Automated Vehicle Identification (AVI) systems because of its capability to track moving objects. These automated wireless AIDC systems are effective in manufacturing environments where barcode labels cannot survive.

Active EMFID Tag is equipped with a battery that can be used as a partial or complete source of power for the tag's circuitry and antenna. Some active tags contain replaceable batteries for years of use; others are sealed units.

Ad EMFID Tag Communications can include a measurement of responses from an ad delivery system to an ad request from the user's browser. EMFID Impression Share includes the percentage of searches on all keyword EMFID tag communications, revenue or revenue sharing EMFID tag communications in the keyword group that the advertiser was found on the first page of sponsored listings.

Ad EMFID Tag Communications include the count of ads, which are served to a user. Ads can be requested by the user's browser, (referred to as pulled ads) or they can be pushed, such as e-mail ads. Ad EMFID tag communications are a measurement of responses from an ad delivery system to an ad request from the user's browser, which is filtered for robotic activity and is recorded at a point at late as possible in the process of delivery.

Animal identification using a means of marking is a process done to identify and track specific animals. It is done for a variety of reasons including verification of ownership, biosecurity control, and tracking for research or agricultural purposes.

Anti-Collision refers to varying ways to keep radio waves from one device from interfering with radio waves from another device. EMFID readers may make use of anti-collision algorithms to enable a single reader to read more than one tag in the readers field.

Amplitude Modulation, a means of communication between an EMFID tag and a reader; the data is contained in changes in the amplitude of the carrier wave sent out by the reader.

Animal Biometrics is an emerging field that develops quantified approaches for representing and detecting the phenotypic appearance of species, individuals, behaviors, and morphological traits. It operates at the intersection between pattern recognition, ecology, and information sciences, producing computerized systems for phenotypic measurement and interpretation.

Animal Identification using a means of marking is a process done to identify and track specific animals. It is done for a variety of reasons including verification of ownership, biosecurity control, and tracking for research or agricultural purposes.

Backscatter, EMFID tags can use of a method of communication called backscatter. Tags using backscatter technology reflect the reader's signal right back, modulating the signal to transmit data.

Biometrics is the technical term for body measurements and calculations. It refers to metrics related to human characteristics. Biometrics authentication (or realistic authentication) is used in computer science as a form of identification and access control. It is also used to identify individuals in groups that are under surveillance. Biometric identifiers are then distinctive, measurable characteristics used to label and describe individuals. Biometric identifiers are often categorized as physiological versus behavioral characteristics. Physiological characteristics are related to the shape of the body. Examples include, but are not limited to fingerprint, palm veins, face recognition, facial expression recognition, DNA, palm print, hand geometry, iris recognition, retina and odor/scent. Behavioral characteristics are related to the pattern of behavior of a person, including but not limited to typing rhythm, gait, and voice. Some researchers have coined the term behaviometrics to describe the latter class of biometrics. More traditional means of access control include token-based identification systems, such as a driver's license or passport, and knowledge-based identification systems, such as a password or personal identification number. Since biometric identifiers are unique to individuals, they are more reliable in verifying identity than token and knowledge-based methods; however, the collection of biometric identifiers raises privacy concerns about the ultimate use of this information.

Bidirectional EMFID tags that are bidirectional are able to operate (that is, be read or be written to) from the front or from the back.

Biometric Identification refers to metrics related to human characteristics and traits. Biometrics authentication (or realistic authentication) is used in computer science as a form of identification and access control. It is also used to identify individuals in groups that are under surveillance. Biometric identifiers are the distinctive, measurable characteristics used to label and describe individuals. Biometric identifiers are often categorized as physiological versus behavioral characteristics.

Blockchain Technology, originally block chain, is a continuously growing list of records, called blocks, which are linked and secured using cryptography. Each block typically contains a hash pointer as a link to a previous block, a timestamp and transaction data. By design, blockchains are inherently resistant to modification of the data. The *Harvard Business Review* describes it as "an open, distributed ledger that can record transactions between two parties efficiently and in a verifiable and permanent way." For use as a distributed ledger, a blockchain is typically managed by a peer-to-peer network collectively adhering to a protocol for validating new blocks. Once recorded, the data in any given block cannot be altered retroactively without the alteration of all subsequent blocks, which requires collusion of the network majority. Blockchains are secure by design and are an example of a distributed computing system with high Byzantine fault tolerance. Decentralized consensus has therefore been achieved with a blockchain. This makes blockchains potentially suitable for the recording of events, medical records, and other records management activities, such as identity management, transaction processing, documenting provenance, food traceability or voting. The first blockchain was conceptualized in 2008 by an anonymous person or group known as Satoshi Nakamoto and implemented in 2009 as a core component of bitcoin where it serves as the public ledger for all transactions. The invention of the blockchain for bitcoin made it the first digital currency to solve the double spending problem without the need of a trusted authority or central server. The bitcoin design has been the inspiration for other applications. blockchain is a digitized, decentralized, public ledger of all cryptocurrency transactions. Constantly growing as 'completed' blocks (the most recent transactions) are recorded and added to it in chronological order, it allows market participants to keep track of digital currency transactions without central record-keeping. Each node (a computer connected to the network) gets a copy of the blockchain, which is downloaded automatically. Originally developed as the accounting method for the virtual currency Bitcoin, blockchains—which use what's known as distributed ledger technology (DLT)—are appearing in a variety of commercial applications today. Currently, the technology is primarily used to verify transactions, within digital currencies though it is possible to digitize, code and insert practically any document into the blockchain. Doing so creates an indelible record that cannot be changed; furthermore, the record's authenticity can be verified by the entire community using the blockchain instead of a single centralized authority.

Cryptocurrency (or crypto currency) is a digital asset designed to work as a medium of exchange that uses cryptography to secure its transactions, to control the creation of additional units, and to verify the transfer of assets. Cryptocurrencies are classified as a subset of digital currencies and are also classified as a subset of alternative currencies and virtual currencies. Bitcoin, created in 2009, was the first decentralized cryptocurrency. Since then, numerous cryptocurrencies have been created. These are frequently called altcoins, as a blend of bitcoin alternative. Bitcoin and its derivatives use decentralized control as opposed to centralized electronic money/central banking systems. The decentralized control is related to the use of bitcoin's blockchain transaction database in the role of a distributed ledger.

Cryptocurrency exchanges or digital currency exchanges are businesses that allow customers to trade cryptocurrencies or digital currencies for other assets, such as conventional fiat money, or different digital currencies. They can be market makers that typically take the bid/ask spreads as transaction commissions for their services or simply charge fees as a matching platform. DCEs may be brick-and-mortar businesses, exchanging traditional payment methods and digital currencies, or strictly online businesses, exchanging electronically transferred money and digital currencies. Most digital currency exchanges operate outside of Western countries, avoiding regulatory oversight and complicating prosecutions, but DCEs often handle Western fiat currencies, sometimes maintaining bank accounts in several countries to facilitate deposits in various national currencies. They may accept credit card payments, wire transfers, postal money orders, cryptocurrency or other forms of payment in exchange for digital currencies. They can send cryptocurrency to your personal cryptocurrency wallet. Many can convert digital currency balances into anonymous prepaid cards, which can be used to withdraw funds from ATMs worldwide. Some digital currencies are backed by real-world commodities such as gold. Creators of digital currencies are often independent of the DCEs that trade the currency. In one type of system, digital currency providers, or DCPs, are businesses that keep and administer accounts for their customers, but generally do not issue digital currency to those customers directly. Customers buy or sell digital currency from DCEs, who transfer the digital currency into or out of the customer's DCP account. Some DCEs are subsidiaries of DCP, but many are legally independent businesses. The denomination of funds kept in DCP accounts may be of a real or fictitious currency.

Digital Asset, in essence, is anything that exists in a binary format and comes with the right to use. Data that do not possess that right are not considered assets. Digital assets include but are not exclusive to: digital documents, audible content, motion picture, and other relevant digital data that are currently in circulation or are, or will be stored on digital appliances such as: personal computers, laptops, portable media players, tablets, storage devices, telecommunication devices, and any and all apparatuses which are, or will be in existence once technology progresses to accommodate for the conception of new modalities which would be able to carry digital assets; notwithstanding the proprietorship of the physical device onto which the digital asset is located.

Digital Wallet refers to an electronic device that allows an individual to make electronic transactions. This can include purchasing items on-line with a computer or using a smartphone to purchase something at a store. An individual's bank account can also be linked to the digital wallet. They might also have their driver's license, health card, loyalty card(s) and other ID documents stored on the phone. The credentials can be passed to a merchant's terminal wirelessly via near field communication (NFC). Increasingly, digital wallets are being made not just for basic financial transactions but to also authenticate the holder's credentials. For example, a digital wallet can verify the age of the buyer to the store while purchasing alcohol. The system has already gained popularity in Japan, where digital wallets are known as "wallet mobiles". A cryptocurrency wallet is a digital wallet where private keys are stored for cryptocurrencies like bitcoin.

Micropayment Channel or Payment Channel is class of techniques designed to allow users to make multiple Bitcoin transactions without committing all of the transactions to the Bitcoin block chain. In a typical payment channel, only two transactions are added to the block chain but an unlimited or nearly unlimited number of payments can be made between the participants. Several channel designs have been proposed or implemented over the years. This article describes some of them. Many designs are vulnerable to transaction malleability. Specifically, many designs require a way to be able to spend an unsigned transaction data, electronic payment data, in order to ensure that the channel can be opened atomically. Thus, these designs require a malleability fix that separates the signatures from the part of the transaction that is hashed to form the txid.

Domestic Payments, At a procedural level, the process of inter-bank clearing requires an intricate coordination of resource-intensive steps between banks, clearing houses, and the central bank. These steps are typically not executed at a constant basis, but rather as a processing cycle, which happens several times a day. The outcome of it is that payment can often end up credited one or more days after their initiation, especially over weekends or holidays. The intricacy of the current system constitute a procedural challenge for payment service providers, and highlights the need for a more efficient system for real-time payment, both domestically and internationally.

International Payments, to achieve real-time payments on an international scale, there will be a need to introduce foreign exchange (FX) market makers to the blockchain network. They will perform currency conversions on transactions between consumer bank accounts. Central bank participation on the network in a market maker capacity would also be needed between payment service providers in different currency jurisdictions. In this way, real-time payments can potentially be achieved on a cost-effective basis.

Smart Contract, a smart contract is a computer protocol intended to facilitate, verify, or enforce the negotiation or performance of a contract. Smart contracts allow to perform credible transactions without third parties. These transactions are traceable and irreversible. Smart contracts were first proposed by Nick Szabo in 1994. Proponents of smart contracts claim that many kinds of contractual clauses may be made partially or fully self-executing, self-enforcing, or both. The aim with smart contracts is to provide security that is superior to traditional contract law and to reduce other transaction costs associated with contracting. Smart contracts have been used primarily in association with cryptocurrencies. The first real-world smart contract to gain mainstream coverage was The DAO, a decentralized autonomous organization for venture capital funding, running on Ethereum, which was launched with US $250 million in crowdfunding in May 2016 and was hacked and drained of 3,689,577 ETH three weeks later.

Virtual Currency, also known as virtual money, is a type of unregulated, digital money, which is issued and usually controlled by its developers, and used and accepted among the members of a specific virtual community. The Financial Crimes Enforcement Network (FinCEN), a bureau of the US Treasury, defined virtual currency in its guidance published in 2013. In 2014, the European Banking Authority defined virtual currency as "a digital representation of value that is neither issued by a central bank or a public authority, nor necessarily attached to a fiat currency, but is accepted by natural or legal persons as a means of payment and can be transferred, stored or traded electronically". By contrast, a digital currency that is issued by a central bank is defined as "central bank digital currency".

Chipless RFID tags are RFID tags that do not require a microchip in the transponder. RFIDs offer longer range and ability to be automated, unlike barcodes that require a human operator for interrogation. The main challenge to their adoption is the cost of RFIDs. The design and fabrication of ASICs needed for RFID are the major component of their cost, so removing ICs altogether can significantly reduce its cost. The major challenges in designing chipless RFID is data encoding and transmission.

Chipless EMFID, also known as RF fibers is one that does not make use of any integrated circuit technology to store information. The tag uses fibers or materials that reflect a portion of the reader's signal back; the unique return signal can be used as an identifier. The fibers are shaped in varying ways; thin threads, fine wires or even labels or laminates. At volume, they range in cost from ten cents to twenty-five cents per unit. Chinless EMFID tags can be used in many varying environments than EMFID tags with electronic circuitry. They tend to work over a wider temperature range; these tags also are less sensitive to RF interference. Chinless tags are sometimes used in anti-counterfeiting with documents. However, since the tags cannot transmit a unique serial number, they are less usable in the supply chain.

Contactless RFID Smart Card refers to identification cards (for example, some credit cards) that do not need to make contact with the reader to be read, or swiped in a special slot. This capability is implemented using a tiny EMFID tag in the card; the intent is to provide the user with greater convenience by speeding checkout or authentication processes.

Contactless RFID Credit Card is varying from an ordinary credit card. A contactless credit card uses EMFID technology to store information about your account and to transfer it to the merchant. Standard credit cards carry data on a magnetic strip; when the card is swiped against a reader, the data is transferred. It is expected that, by the end of 2006, between 35 and 50 million contactless cards will be in use in the United States at as many as 50,000 merchant locations.

Digital Mapping is the process by which an automatic identification data collection is compiled and formatted into a virtual image. The primary function of this technology is to produce maps that give accurate representations of a particular area, detailing major road arteries and other points of interest (which can be used according to the present developments further including the use of EMFID tags, GPS, RTLS, mobile mapping, and location mapping).

Ear Tag is a plastic or metal object used for identification of domestic livestock and other animals. If the ear tag uses Radio Frequency Identification Device (RFID) technology it is referred to as an electronic ear tag. Electronic ear tags conform to international standards ISO 11784 and ISO 11785 working at 134.2 kHz, as well as ISO/IEC 18000-6C operating in the UHF spectrum. There are other non-standard systems such as Destron working at 125 kHz. Although there are many shapes of ear tags, the main types in current use are as follows: Flag-shaped ear tag: two discs joined through the ear, one or both bearing a wide, flat plastic surface on which identification details are written or printed in large, easily legible script. Button-shaped ear tag: two discs joined through the ear. Plastic clip ear tag: a molded plastic strip, folded over the edge of the ear and joined through it. Metal ear tag: an aluminum, steel or brass rectangle with sharp points, clipped over the edge of the ear, with the identification stamped into it. Electronic Identification Tags, include the EID number and sometimes a management number on the button that appears on the back of the ear. These can at times be combined as a matched set, which includes Visual tags with Electronic Identification Tags. Each of these except the metal type may carry a RFID chip, which normally carries an electronic version of the same identification number.

EAS Tags only identify if an item has been paid or not. Electronic Article Surveillance (EAS). This system uses tags that can be disabled by authorized agents. For example, when you purchase a hardback book from your local bookstore, the clerk places the book on a special plate and activates an electromagnet that disables the tag. Biosensors are placed at exit points; if the sensor detects a tagged object with an active tag, an alarm goes off.

Electronic Product Code (EPC) Tags is a set of digits intended to complement barcodes like the Universal Product Code. An EPC is segmented, with digits that identify the manufacturer, the product category and the individual item. When product data is placed on an EMFID tag, a special piece of data called an error correcting code is created based on the product data using a known algorithm. The algorithm (or rule) used to create the correcting code is called the error correcting protocol. When the tag is activated and read, the reader pulls out the product data as well as the ECC.

Electronic Tagging is a form of surveillance, which uses an electronic device, fitted to the person. for example an ankle monitor is used for people who have been sentenced to electronic monitoring by a court, or are required to wear a tag upon release from prison. It is also used in healthcare settings with people with dementia and in immigration contexts in some jurisdictions. If the device is based on GPS technology, it is usually attached to a person by a probation officer, law enforcement or a private monitoring services company field officer, and is capable of tracking the wearer's location wherever there is the satellite signal to do so. Electronic monitoring tags can be also used in combination with curfews to confine defendants or offenders to their home as a condition of bail, as a stand-alone order or as a form of early release from prison. The combination of electronic monitoring with a curfew usually relies on radio frequency (RF) technology, which differs from GPS technology.

Electromagnetic Frequency (EMF) Identification, as the broadest term, non-limiting examples include, but are not limited to, Radio waves; Infrared; Ultraviolet; and Soft X-rays (Freq./Wavelength), that can be used for communication as: Radio waves: ELF to EHF: Extremely Low Frequency (ELF: 3 Hz/100 Mm); SuperLF: (30 Hz/10 Mm); UltaLF (voice) (300 Hz/1 Mm); (very low frequency (VLF) as (3 kHz/100 km), LF (30 kHz/10 km); Medium Freq (300 kHz/1 km); HighF (3 MHz/100 m); VeryHF (30 MHz/10 m); UltraHF (300 MHz/1 m); Microwaves are SHF and EHF of radio waves (SuperHF (3 GHz/1 dm); ExtremelyHF (30 GHz/1 cm); Terahertz radiation is between Microwaves and Far IR: (100-10,000 GHz/3 cm-1 mm); then: Infrared (IR): Far IR (300 GHz/1 mm); Mid IR (3 THz/100 microM); Near IR: (30 Hz/10 microM); (Note Visible Light is 400-700 nm wavelength) between IF and UV; Ultraviolet (UV): NearUV (300 THz/1 microM); ExtremeUV (3 PHz/100 nm); and Soft X-rays (30 PHz/10 nm) to (3 EHz/100 pm); Low Frequency (LF); High Frequency (HF); and Ultra High Frequency (UHF).

EMFID, as the broadest term, which includes the wireless use of electromagnetic fields, radio frequency (RF) or Wi-Fi frequency ranges, EMFID hardware or software EMFID, to transfer data that can be encrypted to other devices and/or physical objects, including without limitation, (e.g., wearable banking wristbands, kitchen appliances, garments, fashion apparel, household items, internet things, remote controls, TVs, cabinets, walls, flooring, automobiles, radio clocks, electronics, wallets, digital wallets, transmitters, airport scanners, readers, printers, tags, smart labels, UHF passive RFID transceiver chips, inlays & labels, fixed & mobile readers, smartphones, mobile devices, blue tooth devices or other wireless devices, keys, currency, passport cards, enhanced drivers' license (EDL), barcodes, drugs, cigarettes, EMFID labels of pharmaceutical products, electronic product code (EPC), EMFID inventory tracking, EMFID logistic applications, animal identification, Garment EMFID Inventory Management System (GIMS), EMFID chip vaccinations, clothing, merchandise, pharma/healthcare, products or other services or experiences, mobile coupons, electronic skin tattoos, electronic hologram EMFID tags, payment cards, student ID cards, corporate identification cards or integration of biometric ID cards, wireless biosensors, laptops, computers, PCs, and other devices, etc.) for real-time tracking of EMFID communications, security, routing, analysis, storage, access and retrieval using a wireless device for detection of EMFID tracking of personal data for one or more individuals or end user that uses a higher spectrum of light, sound and electromagnetic frequency (EMF) identification (EMFID) technologies for multiple EMFID tag communications enabled objects, EMFID labels of pharmaceutical products, electronic product code (EPC), EMFID inventory tracking, EMFID logistic applications, animal identification, Garment EMFID Inventory Management System (GIMS), EMFID chip vaccinations and/or embedded in any physical objects, including without limitation, EMFID edible drugs, Medical EMFID card with prescription, EMFID labels of pharmaceutical products, electronic product code (EPC), EMFID inventory tracking, EMFID logistic applications, animal identification, Garment EMFID Inventory Management System (GIMS), EMFID chip vaccinations, EMFID packaging, EMFID passports, EMFID credit cards, EMFID debit cards, other forms of EMFID payment systems, EMFID travel cards, edible EMFID tags, EMFID navigation systems, EMFID vehicle tags, EMFID retail, EMFID clothing, EMFID pharma/healthcare, EMFID merchandise, EMFID smart dust, EMFID mobile devices, EMFID wireless devices, EMFID international mobile equipment identity (IMEI), other EMFID wireless or EMFID handheld devices, computers, PCs, currency, identification cards, products or other services or experiences and/or EMFID microchip and/or nanobots implant subdermal in animals and/or individuals to link health records, credit history and digital wallet. The tags contain electronically stored information. Some tags are powered by electromagnetic induction from magnetic fields produced near the reader. Some types collect energy from the interrogating radio waves and act as a passive transponder. Other types have a local power source such as a battery and may operate at hundreds of meters from the reader. Unlike a barcode, the tag does not necessarily need to be within line of sight of the reader, and may be embedded in any physical objects. EMFID is one method for Automatic identification Data Capture (AIDC).

EMFID Antennas, EMFID antenna offers a variety of gain, polarization and radiation pattern options.

EMFID Control Systems in which the tracked objects never leave the company or organization. All of the data related to the object is stored in one place; the complete history of the object is readily available. The usual concerns about EMFID standards do not apply, since the object tracked does not leave the system.

RF Fibers, also known as chipless EMFID, is a kind of EMFID tag that does not make use of any integrated circuit technology to store information. Fibers or materials are used that reflect a portion of the reader's signal back; the unique return signal can be used as an identifier. Thin threads, fine wires or even labels or laminates—RF fibers are available in many forms. At volume, they range in cost from ten cents to twenty-five cents per unit. RF fibers can be used in more environments than EMFID tags with electronic circuitry. They tend to work over a wider temperature range; these tags also are less sensitive to RF interference. RF fibers are sometimes used in anti-counterfeiting with documents. However, since the tags cannot transmit a unique serial number, they are less usable in the supply chain.

EMFID Fixed Readers, smart EMFID readers to reduce the communications on a network or servers.

EMFID Handheld Readers combines the power of a mobile device with wireless networking and multi-protocol EMFID capabilities.

EMFID Microchip or Nanobot Implants is a human EMFID microchip and/or nanobots implant is an identifying integrated circuit device or EMFID transponder encased in silicate glass and implanted in the body of a human being. A subdermal implant typically contains a unique ID number that can be linked to information contained in an external database, such as personal identification, medical history, medications, allergies, and contact information.

EMFID Printers, with an Intermec EMFID printer, print and encode smart labels to enable EMFID tracking for quick and accurate data collection.

EMFID Tags, including Smart Labels, are used in many industries. An EMFID tag enabled an automobile during production can be used to track its progress through the assembly line. Pharmaceuticals can be tracked through warehouses. Livestock and pets may have tags injected, allowing positive identification of the animal. Since EMFID tags can be enabled cash, clothing, possessions, or even implanted within people, the possibility of reading personally linked information without consent has raised serious privacy concerns. An EMFID tag is an EMFID microchip and/or nanobots combined with an antenna in a compact package; the packaging is structured to allow the EMFID tag to be enabled an object to be tracked. The tag's antenna picks up signals from an EMFID reader or scanner and then returns the signal, usually with some additional data (like a unique serial number or other customized information). EMFID tags can be very small—the size of a large rice grain. Others may be the size of a small paperback book.

EMFID Reader is a device that is used to interrogate an EMFID tag. The reader has an antenna that emits radio waves; the tag responds by sending back its data. A number of factors can affect the distance at which a tag can be read (the read range). The radio frequency used for identification, the antenna gain, the orientation and polarization of the reader antenna and the transponder antenna, as well as the placement of the tag on the object to be identified will all have an impact on the EMFID system's read range.

EMFID Tag Collision in EMFID systems happens when multiple tags are energized by the EMFID tag reader simultaneously, and reflects their respective signals back to the reader at the same time. This problem is often seen whenever a large volume of tags must be read together in the same RF field. The reader is unable to differentiate these signals; tag collision confuses the reader. Varying systems have been invented to isolate individual tags; the system used may vary by vendor. For example, when the reader recognizes that tag collision has taken place, it sends a special signal (a "gap pulse"). Upon receiving this signal, each tag consults a random number counter to determine the interval to wait before sending its data. Since each tag gets a unique number interval, the tags send their data at varying times.

EMFID Reader Collision occurs in EMFID systems when the coverage area of one EMFID reader overlaps with that of another reader. This causes two varying problems: Signal interference☐ The RF fields of two or more readers may overlap and interfere. This can be solved by having the readers programmed to read at fractionally varying times. This technique (called time division multiple access—TDMA) can still result in the same tag being read twice. Multiple reads of the same tag☐ The problem here is that the same tag is read one time by each of the overlapping readers. The only solution is to program the EMFID system to make sure that a given tag (with its unique ID number) is read only once in a session.

EMFID Vehicle Mount Readers, mobility meets the convenience of hands-free scanning with or no human intervention.

Employee Management EMFID Technology, can be used by employers to create an employee management system. The tag on the card can tell the system when a card is checked in and checkout via the reader, creating an automated punch-card type system that is more accurate in tracking the amount of time employees spend working. This can be used to create more accurate statements for hourly wages.

EMFID Impression(s), non-limiting examples include, but are not limited to, a view or an ad view, is a term that refers to the point in which an ad is viewed once by a visitor, or displayed once on a web page. The number of EMFID tag communications of a particular advertisement is determined by the number of times the particular page is located and loaded. It is a measurement of how many times an advertising placement would be served up on a web site on a computer, PC, mobile devices, blue tooth devices or other wireless devices, EMFID tags or multiple EMFID devices. EMFID impression refers to any type of Impression as described or defined herein, or as known in the art.

Enhanced Driver's License (EDL), is a state issued identity document that has the features of a conventional drivers' license, but additionally carries an RFID tag like that in a Passport Card. As with the Passport Card, an EDL is valid for land and sea entry into the United States.

Error Correcting Code, the reader uses the error correcting protocol on the product data, and compares the result to the ECC. If they match, the reader knows that the data has been read correctly. Similar methods are used in most data transfer systems to ensure the correctness of each data packet as it moves from one part of the system to another. A reader that performs this check automatically is said to be in error correcting mode.

Excite, the tag reader transmits radio frequency energy to stimulate a passive EMFID tag (to provide power to transmit its data back); the tag reader is said to excite the EMFID tag.

Factory Programming is when the information on an EMFID tag has been set during the manufacturing process, the resulting read-only tag is said to have factory programming.

Field Programming refers to the process of placing data on an EMFID tag after the manufacturing process has been completed. Field programming is usually performed before the tag is installed on the product or object. Such tags typically have some form of non-volatile memory; "non-volatile" means that the memory chip retains information without having to use electricity to power the chip. Some field-programmable EMFID tags have two forms of memory; a programmable chip and a form of read-only memory containing a unique serial number imposed at the factory.

Frequency Hopping is a technique used to keep two or more EMFID readers from interfering with each other while reading EMFID tags in the same area. For example, UHF EMFID readers in the United States are said to operate at 915 MHz They actually operates between 902 and 928 MHz, jumping randomly (or in a predetermined sequence) to frequencies in between 902 and 928 MHz. The chances of interference (of two readers attempting to interrogate the same tag) are small if the band of the reader is wide enough.

Frequency Modulation, a means of communication between an EMFID tag and a reader; the data is contained in changes between the two frequencies of the carrier wave sent out by the reader.

Garment EMFID Inventory Management System (GIMS), as in the broadest terms, use RFID technologies to track items location and usage, employee assignments of uniform, daily pickup, cleaning including automatic billing by department, purchasing, selling, repairs, alterations, tracking history of repair and productivity of tailors.

GIS Technologies is a system designed to capture, store, manipulate, analyze, manage and present all types of geographical data.

Hologram EMFID Tag, non-limiting examples include, but are not limited to, a the hologram EMFID tags combines two technologies with a view of making tacking and verifying the authenticity of a product as watertight as possible. Future applications are likely to include using it to secure batches of medicines. Hologram EMFID tags interactions encrypt the data.

Harvest, a passive EMFID tag is said to harvest energy from an EMFID reader antenna; passive tags have no energy source of their own, and they take what little they need from the reader.

Human Microchip Implant is typically an identifying integrated circuit device or RFID transponder encased in silicate glass and implanted in the body of a human being. This type of subdermal implant usually contains a unique ID number that can be linked to information contained in an external database, such as personal identification, law enforcement, medical history, medications, allergies, and contact information.

ISO, the International Organization for Standardization, is an independent, non-governmental organization, the members of which are the standards organizations of the 163 member countries. It is the world's largest developer of voluntary international standards and facilitates world trade by providing common standards between nations. Over twenty thousand standards have been set covering everything from manufactured products and technology to food safety, agriculture and healthcare. Use of the standards aids in the creation of products and services that are safe, reliable and of good quality. The standards help businesses increase productivity while minimizing errors and waste. By enabling products from different markets to be directly compared, they facilitate companies in entering new markets and assist in the development of global trade on a fair basis. The standards also serve to safeguard consumers and the end-users of products and services, ensuring that certified products conform to the minimum standards set internationally.

ISO 11784 & 11785 are international standards that regulate the radio frequency identification (RFID) of animals, which is usually accomplished by implanting, introducing or attaching a transponder containing a microchip to an animal. RF identification of animals requires that the bits transmitted by a transponder are interpretable by a transceiver. Usually the bit stream contains data bits, defining the identification code and a number of bits to ensure correct reception of the data bits. ISO 11784 specifies the structure of the identification code. ISO 11785 specifies how a transponder is activated and how the stored information is transferred to a transceiver (the characteristics of the transmission protocols between transponder and transceiver. These standards are updated and expanded in ISO 14223, which regulates "advanced" transponders for animals, and ISO 24631, which regulates testing procedures for conformance with ISO 11784 & 11785 as well as performance.

Inductive Coupling is the transfer of energy from one circuit (such as a conductive antenna and associated circuitry) to another by means of mutual inductance between the two circuits. Some EMFID tags and readers exchange information using inductive coupling between their antennas.

International Mobile Equipment Identify or IMEI, uniquely identifies mobile phone used on a network.

Internet of Things, is an amalgamation of sensors, RFID, cloud computing, advanced analytics, big data, wireless, mobile and other technologies that create a network of smart devices, all with unique identifiers and ability to communicate information and conditions over the Internet or similar wide area network.

Location-Based EMFID Advertising, non-limiting examples of location-based advertising include a new form of advertising that integrates mobile advertising with location-based services (which can be used according to the present developments further including the use of EMFID tags, GPS, RTLS, mobile mapping, and location mapping) and online or mobile payment system for coupons, location-based promotions, location-based offers, location-based coupons, information, social media content, promotions or offers in connection with an online EMFID tag or mobile EMFID tag and online or mobile coupons and information, social media content, promotions or offers for products and/or other services, of interest, of past, present or future customers, users, targets and/or target markets. The technology is used to pinpoint user/consumer's location and provide location specific geotargeted or geotagged EMFID advertisements on their mobile device.

Location-Based EMFID Commerce, (L-Commerce) refers to the localization of products and services through mobile commerce and context aware computing technologies. L-commerce revolves around 5 key service areas: a) Transaction data, electronic payment data, location data, track movement data, logistics data, transportation data, physical, emotional and mental state data, integration of biometric data, healthcare, physical health conditions, medical conditions, track movement, logistics, transportation, track diseases for pets, livestock, dairy cows, cattle or other animals, diseases and conditions for disease control and prevention, monitoring antibiotics, pharmaceutical data and other data to develop a profile for one or more end user, pet, livestock, dairy cows, cattle or other animals, including tracking movement, logistics data, and/or location data using radio and other frequency tags and relaying data from EMFID tag interactions on different codes and readers to a database that can be accessed by members of a network, and readers, electronic health record data (EHR), physical, emotional and mental state data, integration of biometric data, healthcare, physical health conditions, medical conditions, track movement, logistics, transportation, track diseases for pets, livestock, dairy cows, cattle or other animals, diseases and conditions for disease control and prevention, monitoring antibiotics, pharmaceutical data communications EMFID scanner and readers, wherein predictive analytics are used for one or more individuals analysis, marketing, determining the basic position of a person or a thing; b) EMFID navigation: plotting a route from one location to another; c) Tracking: monitoring the movement of a person or a thing; d) Mapping: creating maps of specific geographical locations; e) Timing: determining the precise time at a specific location; f) Providing location-based services involves several technologies; g) Position Determining Equipment (PDE)—identifies location of mobile device. h) Mobile Positioning Center (MPC)—a server that manages the location info from PDE; i) Geographic Information System (GIS)—geographic contents consists of streets, road maps, addresses, and points of interest; and j) Location-specific content—used in conjunction with geographic content to provide the location of particular services, of interest, of past, present or future customers, users, targets and/or target markets.

Location-Based EMFID Deals and Offers, non-limiting examples of location-based deals and offers are based upon where you are and online or mobile payment system for coupons, location-based promotions, location-based offers, location-based coupons, information, social media content, promotions or offers in connection with an online EMFID tag or mobile EMFID tag and online or mobile coupons and information, social media content, promotions or offers for products and/or other services, of interest, of past, present or future customers, users, targets and/or target markets. The technology is used to pinpoint user/consumer's location and provide location specific geo-targeted or geo-tagged advertisements and/or location-based promotions, location-based offers, location-based coupons, information, social media content, promotions or offers in connection with an online EMFID tag or mobile EMFID tag across the web and on mobile device (which can be used according to the present developments further including the use of EMFID tags, GPS, RTLS, mobile mapping, and location mapping.

Location-Based EMFID Services, non-limiting examples include, but are not limited to, a general class of computer program level services used to include specific controls for location and time data as control features in computer programs and online or mobile information, social media content, promotions or offers and/or payment systems for location-based promotions, location-based offers, location-based coupons, information, social media content, promotions or offers in connection with an online EMFID tag or mobile EMFID tag and online or mobile coupons and information, social media content, promotions or offers for products and/or other services (which can be used according to the present developments further including the use of EMFID tags, GPS, RTLS, mobile mapping, and location mapping).

Location EMFID Mapping is the place or point that something is at and closely related to location-based services and includes a check-in feature that ties in social networking integration and location-based services (which can be used according to the present developments further including the use of EMFID tags, GPS, RTLS, mobile mapping, and location mapping).

Location Mapping, refers to any type of mapping of any user, product provider, service provider, target market, or demographic group location, e.g., but not limited to GPS, RTLS, GIS, mapping, holographic mapping, 2D mapping, 3D mapping, triangulation, digital mapping, social mapping, position based mapping, web mapping, location mapping, mapping technologies, mobile mapping, and the like, as defined herein and/or as known in the art.

Longitudinal Scalar Waves, are better for private bidirectional one-to-one communication systems, while transverse electromagnetic (EM) waves are best used for one-way broadcast transmissions like radio, television.

Mapped EMFID Ads, includes a form of advertising in which information or products or other services or experiences are added to online mapping services, of interest, of past, present or future customers, users, targets and/or target markets.

Microchip Implant is an identifying integrated circuit placed under the skin of an animal. The chip, about the size of a large grain of rice, uses passive RFID (Radio Frequency Identification) technology, and is also known as a PIT (Passive Integrated Transponder) tag. Externally attached microchips such as RFID ear tags are commonly used to identify farm and ranch animals, with the exception of horses. Some external microchips can be read with the same scanner used with implanted chips.

Microwave Auditory Effect, describes a technology with the ability to transfer radio-frequency (RF) energy into a human target. The energy is perceived by the brain as sounds inside the target's head as the microwaves are absorbed by the target's body. This technology has already been proven capable of carrying modulated frequencies that sound like recognizable speech to the recipient. Application of the microwave hearing technology can facilitate a private message transmission. It may be useful to provide a disruptive condition to a person not aware of the technology.

Modulation refers to the process by which the EMFID tag changes the carrier signal of the reader antenna to convey information. A variety of schemes to accomplish this are available:

Nanorobotics is the technology field creating machines or robots whose components are at or close to the scale of ananometer ($10^{-9}$ meters). More specifically, nanorobotics refers to the nanotechnology engineering discipline of designing and building nanorobots, with devices ranging in size from 0.1-10 micrometers and constructed of nanoscale or molecular components. The names nanobots, nanoids, nanites, nanomachines or nanomites have also been used to describe these devices currently under research and development. Another definition is a robot that allows precision communications with nanoscale objects, or can manipulate with nanoscale resolution. Such devices are more related to microscopy or scanning probe microscopy, instead of the description of nanorobots as molecular machine. Following the microscopy definition even a large apparatus such as an atomic force microscope can be considered a nanorobotic instrument when configured to perform nanomanipulation. For this perspective, macroscale robots or microrobots that can move with nanoscale precision can also be considered nanorobots.

Nanosensors, are any biological, chemical, or surgical sensory points used to convey information about nanoparticles to the macroscopic world. Nanosensors include various medicinal purposes and as gateways to building other nanoproducts, such as computer chips that work at the nanoscale and nanorobots. Presently, there are several ways proposed to make nanosensors, including top-down lithography, bottom-up assembly, and molecular self-assembly. Nanosensors will be able to store and transfer even greater amount of information than EMFID chips. As with EMFID, not only will pallets be trackable, but also individual items can be tracked, followed and monitored from the production facility to the warehouse to the store and ultimately to the consumer.

National Animal Identification System, (NAIS) is a government-run program in the United States intended to extend government animal health surveillance by identifying and tracking specific animals.

National Animal Identification System (NAIS) is designed to identify all livestock animals and poultry and track their movements. The USDA claims that the NAIS will be able to identify all premises on which animals and poultry are located, and all animals that have had contact with a disease of concern, within 48 hours of discovery. In reality, NAIS provides no food safety benefit and threatens small-scale organic farmers and ranchers, while accelerating farm consolidation and benefiting factory farms.

Network Surveillance, the vast majority of computer surveillance involves the monitoring of data and traffic on the Internet.

Notifiable Disease is any disease that is required by law to be reported to government authorities. The collation of information allows the authorities to monitor the disease, and provides early warning of possible outbreaks. In the case of livestock diseases, there may also be the legal requirement to destroy the infected Inotification. Many governments have enacted regulations for reporting of both human and animal (generally livestock) diseases.

Passive Tag is an EMFID tag that does not contain a battery; the reader supplies the power. When radio waves from the reader are encountered by a passive EMFID tag, the coiled antenna within the tag forms a magnetic field. The tag draws power from it, energizing the circuits in the tag. The tag then sends the information encoded in the tag's memory.

Pet Tag, Dog Tag, pet ID tag is a small flat tag worn on pets' collars or harnesses. Humane societies and rescue organizations recommend that dogs and cats wear these tags, which contain information to enable someone encountering a stray animal to contact the owner. Tags may make noise as animals move. A collar-mount tag, either slide-on or riveted-on, flat to a collar's surface, is silent and therefore eliminates the noise. A tag silencer encloses loose tags in a small neoprene pouch or a soft rubbery plastic ring around the edge of a tag and may reduce noise. The resemblance of human identification tags to this method of display led to military identification tags being called dog tags.

Phase Modulation, a means of communication between an EMFID tag and a reader; the data is contained in changes in the phase of the carrier wave sent out by the reader.

Prediction Markets, many predictions market tools have become available that make it easy to predict and bet on future events. This is a more formal version of social interaction, although it qualifies as a robust type of social software.

Predictive Analytics, or behavior is the study of when, why, how, and where people do or do not buy a product. It blends elements from psychology, sociology, social anthropology, human behavior and economics. It attempts to understand the buyer decision-making process, both individually and in groups. It studies characteristics of individual consumers such as demographics and behavioral variables in an attempt to understand people's wants. It also tries to assess influences on the consumer from one or more individuals or groups such as family, friends, reference groups, and society in general. Predictive analytics encompasses a variety of statistical techniques from modeling, machine learning, and data mining that analyze current and historical facts to make predictions about future, or otherwise unknown, events. In business, predictive models exploit patterns found in historical and transactional data to identify risks and opportunities. Models capture relationships among many factors to allow assessment of risk or potential associated with a particular set of conditions, guiding decision making for candidate transactions, Predictive analytics is used in actuarial science, marketing, financial services, insurance, telecommunications, retail, travel, healthcare, pharmaceuticals and other fields. One of the most well known applications is credit scoring, which is used throughout financial services. Scoring models process a customer's credit history, loan application, customer data, etc., in order to rank-order individuals by their likelihood of making future credit payments on time.

Products means any Product or Products described herein, or as known in the art: non-limiting examples of Products provided through Information, social media content, promotions or offers by the present developments.

Profile Targeting EMFID Tag Communications, non-limiting examples include, but are not limited to, a user or member profile targeting involves a target ads based on a user's profile information, which is stored during the registration process. Advertisers can choose the delivery limitation by targeting to the specific peoples. For instance, on collecting the gender, users can serve unique ads to males and females.

Product Review EMFID Tag Communications, non-limiting examples include, but are not limited to, a view or impression of a product review. Product Reviews are ranked in the major search engines and continue to make sales for years! Survey statistics show that approximately 83% of user/consumers say that product reviews influence their online purchasing decisions; Approximately 70% of online shoppers actively seek out product reviews before they buy; More than half of US online shoppers surveyed, read user reviews as part of their product research; Nearly 9 of 10 U.S. online buyers read reviews at least "some of the time" before making a purchase.

Price Comparison EMFID Tag Communications, a view or impression of a price comparison "allows people to see varying lists of prices for specific products." Basically it is a way to see similar products from varying companies so that users can compare the price and save money.

Promotions, as used herein the term "promotion," or "promotions," or "promoting," or "offer," "offers," or "offering," means providing any type of information in any language or translated into any language or scripting social media content in any language or translated into any language relating to any product or service for the purpose of promoting that product or service, and includes, but is not limited to, any type of Advertisement, Advertising, Ad, marketing, coupon, discount, offer, daily deal, auction, or Impression used for promotion or offer, and the like.

Pulse Duration means of communication between an EMFID tag and a reader; the data is contained in duration of pulses of the carrier wave sent out by the reader, which includes alternative auto identification capabilities designed to bring increased levels of visibility, efficiency and innovation to the communications between an EMFID tag and a reader.

Readers, query tags via radio signals and the tags respond with identifying information.

Radio Tomographic Imaging (RTI), which can "see," locate and track moving people or objects in an area surrounded by inexpensive radio transceivers that send and receive signals. People don't need to wear radio-transmitting ID tags.

Radio-Frequency identification (RFID) uses electromagnetic fields to automatically identify and track tags attached to objects. The tags contain electronically stored information. Passive tags collect energy from a nearby RFID reader's interrogating radio waves. Active tags have a local power source (such as a battery) and may operate hundreds of meters from the RFID reader. Unlike a barcode, the tag need not be within the line of sight of the reader, so it may be embedded in the tracked object. RFID is one method for Automatic Identification and Data Capture (AIDC). RFID tags are used in many industries, for example, an RFID tag attached to an automobile during production can be used to track its progress through the assembly line; RFID-tagged pharmaceuticals can be tracked through warehouses; and implanting RFID microchips in livestock and pets allows for positive identification of animals. Since RFID tags can be attached to cash, clothing, and possessions, or implanted in animals and people, the possibility of reading personally-linked information without consent has raised serious privacy concerns. These concerns resulted in standard specifications development addressing privacy and security issues. ISO/IEC 18000 and ISO/IEC 29167 use on-chip cryptography methods for untraceability, tag and reader authentication, and over-the-air privacy. ISO/IEC 20248 specifies a digital signature data structure for RFID and barcodes providing data, source and read method authenticity. This work is done within ISO/IEC JTC 1/SC 31 Automatic identification and data capture techniques. Tags can also be used in shops to expedite checkout, and to prevent theft by customers and employees. In 2014, the world RFID market was worth US $8.89 billion, up from US $7.77 billion in 2013 and US $6.96 billion in 2012. This figure includes tags, readers, and software/services for RFID cards, labels, fobs, and all other form factors. The market value is expected to rise to US $18.68 billion by 2026.

RFID Tagging is an ID system that uses small radio frequency identification devices for identification and tracking purposes. An RFID tagging system includes the tag itself, a read/write device, and a host system application for data collection, processing, and transmission. An RFID tag (sometimes called an RFID transponder) consists of a chip, some memory and an antenna.

Real-Time Location Systems (RTLS) is used to automatically identify and track the location of objects or people in real time.

Scalar Detectors are for picking up magnetic longitudinal waves.

Scalar Wave, is not a single wave but a result of the interaction (interference) of multiple waves of very high frequency which seem to modulate and encode each other in a harmonious holistic complexity, similar to a hologram. The resulting bidirectional standing wave patterns emanates out of a fixed source point and can be received and decoded by a similar resonant quantum-connected receiver point.

Semantic Advertising, applies semantic analysis techniques to web pages. The process is meant to accurately interpret and classify the meaning and/or main subject of the page and then populate it with targeted advertising spots. By closely linking content to advertising, it is assumed that the viewer will be more likely to show an interest (i.e., through engagement) in the advertised product or service.

Served EMFID Tag Communications, ad networks like "served EMFID tag communications" as it let's them record more EMFID tag communications and charge more money to advertisers.

Service means any service described herein, or as known in the art, non-limiting examples of services provided through information, social media content, promotions or offers by the present developments, can include, but are not limited to: search engines or search requests; social, local, mobile search, mobile services, mobile banking and mobile wallet services, entertainment shopping, online auctions, and the like.

Smart Label, as the broadest terms, which includes a barcode label that contains an EMFID transponder, is called an EMFID smart label. Since the label is able to store information (like a serial number) and communicate with an EMFID reader, it is considered "smart."

Smart Dust EMFID, an EMFID system; the smart objects are located by the readers. Each location is a node. A node can be a production unit, a storage place, a vehicle equipped with a smart object, a warehouse, a sales point as well as any reader unit or group of EMFID readers. Just like the objects, the nodes must have an identification code that is unique on a worldwide scale. It is this, which guarantees an event registered on a particular node will not be mixed with other events.

Smart ID, smart IDs are EMFID equipped identification cards. The card itself can present basic information on its surface, including a picture, name and any relevant information. However, the card's EMFID tag can be linked to a database that can be accessed by members of a network that contains far more information, including police records, medical information, a list of related addresses and other personal information. By scanning the card with a reader, this information can be called up for relevant use.

Social Advertising EMFID Tag Communications, an impression (in the context of online advertising) is a measure of the number of times an ad is displayed, whether it is clicked on or not. Each time an ad displays is counted as one impression. Counting EMFID tag communications is the method by which most Web advertising is accounted and paid for, and the cost is quoted in CPM (cost per thousand EMFID tag communications). (Contrast CPC, which is click- and not impression-based.) Because of the possibility of click fraud, robotic activity is usually filtered and excluded, and a more technical definition is given for accounting purposes by the IAB, a standards and watchdog industry group: Impression—a measurement of responses from a Web server to a page request from the user browser, which is filtered from robotic activity and error codes, and is recorded at a point as close as possible to opportunity to see the page by the user.

Social Functionality, (e.g., the "Like" button) is spreading from host platforms to the wider web.

Social Graph EMFID Tag Communications, represents the connections between people, their friends and family and interests with user/consumer data, location and map data connecting the user/consumer and their friends with the brand or advertiser for a more interactive shopping experience.

Social Shopping, is a method of e-commerce where shoppers' friends become involved in the shopping experience. Social shopping attempts to use technology to mimic the social communications found in physical malls and stores.

Tags, non-limiting examples include, but are not limited to, an assigned to a piece of information such as an Internet bookmark, digital image or computer file.

Target Group or Target Marketing Group, means any group for which information, social media content, promotions or offers are analyzed, generated or provided for.

The Animal Disease Traceability (ADT) Rule, which took effect in March 2013, establishes minimum national official identification and documentation requirements for the traceability of livestock moving interstate. The purpose of the ADT Rule is to improve disease traceability, enhance disease response, and minimize losses. The identification and documentation requirements for each kind of animal covered by the Rule are summarized in the USDA's ADT Rule Summary of General Requirements by Species and outlined briefly below. Some states have even more stringent requirements in place. For specific state requirements, check the USDA's webpage on State Regulations for Importing Animals or contact the State Veterinarian's office for the state in question. Bisos. Official identification requirements apply to all sexually intact bison 18 months of age or over; bison of any age used for rodeo or recreational events; and bison of any age used for shows or exhibitions. Interstate CVIs or other accepted movement documentation are required for all bison moved interstate unless otherwise exempt. Also see Animal Disease Traceability Requirements for Cattle and Bison Moving Interstate (APHIS-VS factsheet). Captive cervids (e.g., deer and elk). The ADT Rule references existing regulations on transporting captive cervids, and there are no changes in the requirements (9 CFR part 77) for interstate movement of these animals. Additionally, 9 CFR Part 55, Control of Chronic Wasting Disease (CWD), establishes official identification requirement for the CWD Herd Certification Program. Cattle. Official identification requirements apply to all sexually intact cattle 18 months of age or over; all female dairy cattle of any age and all dairy males born after Mar. 11, 2013; cattle of any age used for rodeo or recreational events; and cattle of any age used for shows or exhibitions. Interstate CVIs or other accepted movement documentation are required for all cattle moved interstate unless otherwise exempt. Also see Animal Disease Traceability Requirements for Cattle and Bison Moving Interstate (APHIS-VS factsheet). Goats. The ADT Rule references existing regulations on transporting goats, and there are no changes in the requirements (9 CFR part 79) for interstate movement of these animals. Also see Animal Disease Traceability: A Guide to Identifying Sheep and Goats for Interstate Movement (APHIS-VS factsheet). Horses and other equines. In addition to the requirements established by the ADT Rule, equines moving commercially to slaughter must be accompanied by documentation in accordance with 9 CFR part 88, and equine infectious anemia reactors moving interstate must be accompanied by documentation as required by 9 CFR part 75. Also see Animal Disease Traceability: A Guide to Identifying Horses and other Equines for Interstate Movement (APHIS-VS factsheet). Poultry. All poultry, including backyard and pet poultry, are encompassed with certain exceptions, and previous requirements established through the National Poultry Improvement Plan remain. Also see Animal Disease Traceability: A Guide to Identifying Poultry for Interstate Movement (APHIS-VS factsheet). Sheep. The ADT Rule references existing regulations on transporting sheep, and there are no changes in the requirements (9 CFR part 79) for interstate movement of these animals. Also see Animal Disease Traceability: A Guide to Identifying Sheep and Goats for Interstate Movement (APHIS-VS factsheet). Swine. The ADT Rule references existing regulations on transporting all swine (including pet swine), and there are no changes in the requirements (9 CFR part 71.19 and, if applicable, part 85) for interstate movement of these animals. Also see Animal Disease Traceability: A Guide to Identifying Swine for Interstate (APHIS-VS factsheet).

Third Party Click-Through, third party click-through counts are also used by the Internet advertising industry at large to determine the effectiveness of a banner ad (its location, design, etc.) Often the click-through rate (i.e., the percentage of users or members who clicked on the banner after seeing it) is used as a metric to determine the cost of placing the banner ad on a particular Web page.

United States Animal Identification Plan (USAIP)—Officials from approximately 70 animal industry organizations and government agencies have been working since early 2002 on a plan for a national system to identify that might follow food animals from birth to slaughter. The primary purpose is to trace animals back from slaughter through all premises within 48 hours of an animal disease outbreak, in order to determine the disease's origin and to contain it quickly. The plan calls for recording the movement of individual animals or groups of animals in a central database or in a seamlessly linked database infrastructure. USDA's Animal and Plant Health Inspection Service (APHIS) is to coordinate animal ID activities in cooperation with state animal health authorities and producers for disease tracking purposes. Congressional interest in animal ID intensified after a cow with bovine spongiform encephalopathy (BSE) was discovered in the United States in December 2003. USDA in 2004 accelerated work on animal ID, and is incorporating major elements of the USAIP into what it has termed the National Animal Identification System (NAIS). Among the issues in establishing a national program are privacy of producer records, implementation cost and who should pay, and whether animal ID should be mandatory or voluntary.

Unique Behavioral Profile of Users, profile user's web browsing behavior for the purpose of user identification.

User Comment EMFID Tag Communications, gives a user control over their comments on a social networking site. With this module users or members can administer, approve, and delete comments on nodes they create. Permissions are on a per node type basis, so it's a great way to, e.g., allow users or members to manage comments on their own blogs.

Washable EMFID Tags are used to manage inventory of bed sheets, tablecloths, towels, bathrobes, uniforms, hampers and other washable garments.

Wearable Banking Wristbands allows the consumer to pay for goods with their wrists without producing a credit card. The technology combines data masking already in use in various medical record database technologies. The wearable device utilizes a secure microcontroller and small antenna embedded to communicate with a reader through a contactless radio frequency interface during a transaction.

Web Bot is a software program that is claimed to be able to predict future events by tracking keyword EMFID tag communications, revenue or revenue sharing EMFID tag communications entered on the Internet. Internet bots monitor articles, post blogs, forums and other forms of Internet chatter. Words in the lexicon are assigned numeric values for emotional quantifiers such as duration, impact, immediacy, intensity and others.

Web Feeds, or news feed is a data transfer to a database that can be accessed by members of a network format used for providing users or members with frequently updated content marketing EMFID tag communications.

Widgets, is a software widget for the web. A stand along application that can be embedded in any physical objects, including without limitation, EMFID edible drugs, Medical EMFID card with prescription, EMFID labels of pharmaceutical products, electronic product code (EPC), EMFID inventory tracking, EMFID logistic applications, animal identification, Garment EMFID Inventory Management System (GIMS), EMFID chip vaccinations, EMFID packaging, EMFID passports, EMFID credit cards, EMFID debit cards, other forms of EMFID payment systems, EMFID travel cards, edible EMFID tags, EMFID navigation systems, EMFID vehicle tags, EMFID retail, EMFID clothing, EMFID pharma/healthcare, EMFID merchandise, EMFID smart dust, EMFID mobile devices, EMFID wireless devices, EMFID international mobile equipment identity (IMEI), other EMFID wireless or EMFID handheld devices, computers, PCs, currency, identification cards, products or other services or experiences and/or implanted subdermal into third party sites by any user on a page where they have rights of authorship, (e.g. webpage blog or profile on a site).

Radio-Frequency Identification (RFID) is the wireless use of electromagnetic fields to transfer data, for the purposes of automatically identifying and tracking tags attached to objects, and which are included in one or more embodiments of the present developments, as disclosed herein and as known in the art. The tags contain electronically stored information. Some tags are powered by electromagnetic induction from magnetic fields produced near the reader. Some types collect energy from the interrogating radio waves and act as a passive transponder. Other types have a local power source such as a battery and may operate at hundreds of meters from the reader. Unlike a barcode, the tag does not necessarily need to be within line of sight of the reader, and may be embedded in the tracked object. Radio frequency identification (RFID) is one method for Automatic Identification Data Capture (AIDC). RFID tags are used in many industries. An RFID tag attached to an automobile during production can be used to track its progress through the assembly line. Pharmaceuticals can be tracked through warehouses. Livestock and pets may have tags injected, allowing positive identification of the animal. RFID tags can be attached to cash, clothing, possessions, or even implanted within people.

Tags. A radio-frequency identification system can optionally use tags, or labels attached to the objects to be identified. Two-way radio transmitter-receivers called interrogators or readers send a signal to the tag and read its response. RFID tags can be either passive, active or battery-assisted passive. An active tag has an on-board battery and periodically transmits its ID signal. A battery-assisted passive (BAP) has a small battery on board and is activated when in the presence of an RFID reader. A passive tag is cheaper and smaller because it has no battery; instead, the tag uses the radio energy transmitted by the reader. However, to operate a passive tag, it must be illuminated with a power level roughly a thousand times stronger than for signal transmission. That makes a difference in interference and in exposure to radiation. Tags may either be read-only, having a factory-assigned serial number that is used as a key into a database, or may be read/write, where object-specific data can be written into the tag by the system user. Field programmable tags may be write-once, read-multiple; "blank" tags may be written with an electronic product code (EPC) by the user.

RFID tags can optionally contain at least two parts: an integrated circuit for storing and processing information, modulating and demodulating a radio-frequency (RF) signal, collecting DC power from the incident reader signal, and other specialized functions; and an antenna for receiving and transmitting the signal. The tag information is stored in a non-volatile memory. The RFID tag includes either fixed or programmable logic for processing the transmission and sensor data, respectively. An RFID reader can optionally transmit an encoded radio signal to interrogate the tag. The RFID tag receives the message and then responds with its identification and other information. This may be only a unique tag serial number, or may be product-related information such as a stock number, lot or batch number, production date, or other specific information. Since tags have individual serial numbers, the RFID system design can discriminate among several tags that might be within the range of the RFID reader and read them simultaneously.

Readers. RFID systems can optionally be classified by the type of tag and reader. A Passive Reader Active Tag (PRAT) system has a passive reader which only receives radio signals from active tags (battery operated, transmit only). The reception range of a PRAT system reader can be adjusted from 1-2,000 feet (0-600 m), allowing flexibility in applications such as asset protection and supervision. An Active Reader Passive Tag (ARPT) system has an active reader, which transmits interrogator signals and also receives authentication replies from passive tags. An Active Reader Active Tag (ARAT) system uses active tags awoken with an interrogator signal from the active reader. A variation of this system can also use a Battery-Assisted Passive (BAP) tag, which acts like a passive tag but has a small battery to power the tag's return reporting signal. Fixed readers are set up to create a specific interrogation zone, which can be tightly controlled. This allows a highly defined reading area for when tags go in and out of the interrogation zone. Mobile readers may be hand-held or mounted on carts or vehicles.

| Frequencies. RFID frequency bands | | | | |
|---|---|---|---|---|
| Band | Regulations | Range | Data speed | Remarks |
| 120-150 kHz (LF) | Unregulated | 10 cm | Low | Animal identification data collection |
| 13.56 MHz (HF) | ISM band worldwide | 10 cm-1 m | Low to moderate | Smart cards (MIFARE, ISO/IEC 14443) |
| 433 MHz (UHF) 865-868 MHz (Europe) 902-928 MHz (North America) | Short Range Devices | 1-100 m | Moderate | |
| UHF | ISM band | 1-12 m | Moderate to high | EAN, various standards |
| 2450-5800 MHz (microwave) | ISM band | 1-2 m | High | 802.11 WLAN, Bluetooth standards |
| 3.1-10 GHz (microwave) | Ultra wide band | to 200 m | High | semi-active or active tags |

Signaling. Signaling between the reader and the tag is done in several different incompatible ways, depending on the frequency band used by the tag. Tags operating on LF and HF bands are, in terms of radio wavelength, very close to the reader antenna because they are only a small percentage of a wavelength away. In this near field region, the tag is closely coupled electrically with the transmitter in the reader. The tag can modulate the field produced by the reader by changing the electrical loading the tag represents. By switching between lower and higher relative loads, the tag produces a change that the reader can detect. At UHF and higher frequencies, the tag is more than one radio wavelength away from the reader, requiring a different approach. The tag can backscatter a signal. Active tags may contain functionally separated transmitters, airport scanners and receivers, and the tag need not respond on a frequency related to the reader's interrogation signal. An electronic product code (EPC) is one common type of data stored in a tag. When written into the tag by an RFID printer, the tag contains a 96-bit string of data. The first eight bits are a header, which identifies the version of the protocol. The next 28 bits identify the organization that manages the data for this tag; the organization number is assigned by the EPC-Global consortium. The next 24 bits are an object class, identifying the kind of product; the last 36 bits are a unique serial number for a particular tag. These last two fields are set by the organization that issued the tag. Rather like a URL, the total electronic product code (EPC) number can be used as a key into a global database to uniquely identify a particular product. Often more than one tag will respond to a tag reader, for example, many individual products with tags may be shipped in a common box or on a common pallet. Collision detection is important to allow reading of data. Two different types of protocols are used to "singulate" a particular tag, allowing its data to be read in the midst of many similar tags. In a slotted Aloha system, the reader broadcasts an initialization command and a parameter that the tags individually use to pseudo-randomly delay their responses. When using an "adaptive binary tree" protocol, the reader sends an initialization symbol and then transmits one bit of ID data at a time; only tags with matching bits respond, and eventually only one tag matches the complete ID string. Bulk reading is a strategy for interrogating multiple tags at the same time, but lacks sufficient precision for inventory control.

Miniaturization. RFIDs are easy to conceal or incorporate in other items. For example, in 2009 researchers at Bristol University successfully glued RFID micro-transponders to live ants in order to study their behavior. This trend towards increasingly miniaturized RFIDs is likely to continue as technology advances. Manufacture is enabled by using the silicon-on-insulator (SOI) process. These dust-sized chips can store 38-digit numbers using 128-bit Read Only Memory (ROM).

Uses. The RFID tag can be affixed to an object and used to track and manage inventory, assets, people, and the like. For example, it can be affixed to cars, computer equipment, books, mobile phones, and the like. RFID offers advantages over manual systems or use of barcodes. The tag can be read if passed near a reader, even if it is covered by the object or not visible. The tag can be read inside a case, carton, box or other container, and unlike barcodes, RFID tags can be read hundreds at a time. Barcodes can only be read one at a time using current devices. Non limiting examples of uses include, but are not are limited to, Electronic Lock with RFID Card System, ANSI; Electronic key for RFID based lock system; Access management; Tracking of goods; Tracking of persons and animals; Toll collection and contactless payment; Machine readable travel documents; Smart dust (for massively distributed sensor networks); Tracking sports memorabilia to verify authenticity; Airport baggage tracking logistics; Timing sporting events; the adoption of a stable international standard around UHF passive RFID.

Commerce. RFID provides a way for organizations to identify and manage tools and equipment (asset tracking), without manual data entry. RFID is being adopted for item level tagging in retail stores. This provides electronic article surveillance (EAS), and a self-checkout process for consumers. Automatic identification with RFID can be used for inventory systems. Manufactured products such as automobiles or garments, fashion apparel can be tracked through the factory and through shipping to the customer. Casinos can use RFID to authenticate poker chips, and can selectively invalidate any chips known to be stolen.

Access control. RFID tags can optionally be used in identification badges, replacing earlier magnetic stripe cards. Tags can also be placed on vehicles, which can be read at a distance, to allow entrance to controlled areas without having to stop the vehicle and present a card or enter an access code.

Advertising non limiting examples can include using UHF Passive RFID tags in entry passes, RFID cards at most of live events to allow guests to automatically capture and post photos; brands use RFID for social media product placement; RFID for social media marketing. Promotion tracking. To prevent retailers diverting products, manufacturers are exploring the use of RFID tags on promoted merchandise so that they can track exactly which product has sold through the supply chain at fully discounted prices.

Transportation and logistics. Yard management, shipping and freight and distribution centers use RFID tracking. In transportation and shipping, RFID tags mounted on trucks, locomotives and rolling stock identify the owner, identification number and type of equipment and its characteristics. This can be used with a database to identify the lading, origin, destination, and the like. of the commodities being carried. In commercial aviation, RFID can be used to support maintenance on commercial aircraft. RFID tags are used to identify baggage and cargo at several airports and airlines. RFID can be used for vehicle registration and enforcement. RFID can help detect and retrieve stolen cars. Intelligent transportation systems can use RFID, e.g., RFID EZ-Pass reader attached to the pole and antenna (right) used in traffic monitoring. RFID is used in intelligent transportation systems. RFID readers can optionally be deployed at intersection to track E-ZPass tags as a mean to for monitoring traffic flow. The data is fed through the broadband wireless infrastructure to the traffic management center to be used in adaptive traffic control of the traffic lights. Hose stations and conveyance of fluids. An RFID antenna can be installed where the coupling half (fixed part) unmistakably identifies the RFID transponder placed in the other coupling half (free part) after completed coupling. When connected the transponder of the free part transmits all-important information contactless to the fixed part. The coupling's location can be clearly identified by the RFID transponder coding. The control is enabled to automatically start subsequent process steps. Public transport. RFID cards can optionally be used for access control to public transport. RFID cards can optionally be used on aircraft, subway buses, trains, and ferries to identify the traveller at each turnstile and so the system can calculate the fare.

RFID Chip Animal, a microchip implant is an identifying integrated circuit placed under the skin of an animal. The chip, about the size of a large grain of rice, uses passive RFID (Radio Frequency Identification) technology, and is also known as a PIT (Passive Integrated Transponder) tag. Externally attached microchips such as RFID ear tags are commonly used to identify farm and ranch animals, with the exception of horses. Some external microchips can be read with the same scanner used with implanted chips.

RFID passports can be used which can, in addition to information also contained on the visual data page of the passport, can optionally record the travel history (time, date, and place) of entries and exits from a country. Standards for RFID passports are determined by the International Civil Aviation Organization (ICAO), and are contained in ICAO Document 9303, Part 1, Volumes 1 and 2 (6th edition, 2006). ICAO refers to the ISO/IEC 14443 RFID chips in e-passports as "contactless integrated circuits." ICAO standards provide for e-passports to be identifiable by a standard e-passport logo on the front cover. RFID can also optionally include the same information that is printed within the passport, and include a digital picture of the owner, and can implement Basic Access Control (BAC), which functions as a Personal Identification Number (PIN) in the form of characters printed on the passport data page. Before a passports tag can be read, this PIN must be entered into an RFID reader. The BAC also enables the encryption of any communication between the chip and interrogator.

Transportation payments. RFID tags can be used to pay for mass transit fares on bus, trains, or subways, or to collect tolls on highways. Some bike lockers are operated with RFID cards assigned to individual users. A prepaid card is required to open or enter a facility or locker and is used to track and charge based on how long the bike is parked. Car-sharing service uses RFID cards for locking and unlocking cars and for member identification.

Animal identification. RFID tags for animals include ranches, rough terrain, animal identification management. An implantable RFID tag or transponder can also be used for animal identification. The transponders can be passive RFID, or "chips" on animals, and can be a replacement for barcode tags. Currently CCIA tags are used. Human identification. Implantable RFID chips can also be used in humans. The Food and Drug Administration in the United States has approved the use of RFID chips in humans. Some business establishments give customers the option of using an RFID-based tab to pay for service.

Veterinary medicine is the branch of medicine that deals with the prevention, monitoring antibiotics, diagnosis and treatment of disease, disorder and injury in non-human animals. The scope of veterinary medicine is wide, covering all animal species, both domesticated and wild, with a wide range of conditions, which can affect different species. Veterinary medicine is widely practiced, both with and without professional supervision. Professional care is most often led by a veterinary physician (also known as a vet, veterinary surgeon or veterinarian), but also by paraveterinary workers such as veterinary nurses or technicians. This can be augmented by other paraprofessionals with specific specialisms such as animal physiotherapy or dentistry, and species relevant roles such as farriers. Veterinary science helps human health through the monitoring and control of zoonotic disease (infectious disease transmitted from non-human animals to humans), food safety, and indirectly through human applications from basic medical research. They also help to maintain food supply through livestock health monitoring and treatment, and mental health by keeping pets healthy and long living. Veterinary scientists often collaborate with epidemiologists, and other health or natural scientists depending on type of work. Ethically, veterinarians are usually obliged to look after animal welfare.

Institutions. Hospitals and healthcare. RFID can be used in the medical industry and can use both active and passive RFID, e.g., in hospitals, e.g., active RFID to track high-value, or frequently moved items, and where passive technology tracks smaller, lower cost items that only need room-level identification. For example, medical facility rooms can collect data from transmissions of RFID badges worn by patients and employees, as well as from tags assigned to facility assets, such as mobile medical devices. A physical RFID tag may be incorporated with browser-based software to increase its efficacy. This software allows for different groups or specific hospital staff, nurses, and patients to see real-time data relevant to each piece of tracked equipment or personnel. Real-time data is stored and archived to make use of historical reporting functionality and to prove compliance with various industry regulations.

This combination of RFID real-time locating system hardware and software provides a powerful data collection tool for facilities seeking to improve operational efficiency and reduce costs. The trend is toward using ISO 18000-6c as the tag of choice and combining an active tagging system that relies on existing 802.11X wireless infrastructure for active tags, which can also include workflow and inventory management, and to prevent mix-ups of therapies, treatments, and drug administration. For example, 134 kHz RFID chips can be implanted in humans and incorporate personal medical information and can save lives and limit injuries from errors in medical treatments.

Libraries. RFID tags used in libraries can include square book tag, round CD/DVD tag and rectangular VHS tags. Libraries can use RFID to replace the barcodes on library items. The tag can contain identifying information or may just be a key into a database. An RFID system may replace or supplement barcodes and may offer another method of inventory management and self-service checkout by patrons. It can also act as a security device, taking the place of the more traditional electromagnetic security strip.

RFID tags can optionally be used in one or more of clothing, backpacks, and IDs and to keep tabs on individuals by tracking radio chips in their clothing. An RFID card system can optionally be used to check in and out of buildings or properties, e.g., to track individuals, workers, or employees attendance and prevent unauthorized entrance, and for buying items at a shop and food establishment, and for attendance.

Sports. Participants can be RFID tagged to track location, races, speed, practice, metrics, biometrics, order in a race or competition, start and stop times, as a replacement to a stopwatch, and logistics of practice or competition events. Passive and active RFID systems are used in events to track their progress and can include GPS, real-time location systems (RTLS) to automatically identify and track the location of objects or people in real time or other location data and the data can be transferred to smart phones or other computing devices.

The storage of data associated with tracking items will require data storage and filtering, categorizing, and analysis of RFID data is needed to create useful information. Products and services can be tracked by using RFID tags, and can optionally include or replace at the package level Universal Product Code (UPC) or EAN from unique barcodes. A unique identity is important for proper use of RFID tags, or can include special choice of the numbering scheme. RFID tag data capacity is large enough that each individual tag can have a unique code. The uniqueness of RFID tags means that a product may be tracked as it moves from location to location, finally ending up in the consumer's hands. This can also be used to combat theft and other forms of product loss. The tracing of products is an important feature that gets well supported with RFID tags containing a unique identity of the tag and also the serial number of the object. This can help companies cope with quality deficiencies and resulting recall campaigns, but also contributes to concern about tracking and profiling of consumers after the sale.

Telemetry. Active RFID tags also have the potential to function as low-cost remote sensors that broadcast telemetry back to a base station. Applications of tagometry data can include sensing of road conditions by implanted beacons, weather reports, and noise level monitoring. Passive RFID tags can also report sensor data. For example, the Wireless Identification and Sensing Platform is a passive tag that reports temperature, acceleration and capacitance to commercial Gen2 RFID readers. It is also possible that active or battery-assisted passive (BAP) RFID tags, can broadcast a signal to an in-store receiver to determine whether the RFID tag (product) is in the store.

Low-frequency (LF: 125-134.2 kHz and 140-148.5 kHz) (LowFID) tags and high-frequency (HF: 13.56 MHz) (HighFID) tags can be used globally without a license. Ultra-high-frequency (UHF: 865-928 MHz) (Ultra-HighFID or UHFID) tags cannot be used globally as there is no single global standard. In North America, UHF can be used unlicensed for 902-928 MHz (±13 MHz from the 915 MHz center frequency), but restrictions exist for transmission power. In Europe, RFID and other low-power radio applications are regulated by ETSI recommendations EN 300 220 and EN 302 208, and ERO recommendation 70 03, allowing RFID operation with somewhat complex band restrictions from 865-868 MHz. Readers are required to monitor a channel before transmitting ("Listen Before Talk"); this requirement has led to some restrictions on performance, the resolution of which is a subject of current research. The North American UHF standard is not accepted in France as it interferes with its military bands. On Jul. 25, 2012, Japan changed its UHF band to 920 MHz, more closely matching the United States' 915 MHz band. For China, there is no regulation for the use of UHF. Each application for UHF in these countries needs a site license, which needs to be applied for at the local authorities, and can be revoked. For Australia and New Zealand, 918-926 MHz are unlicensed, but restrictions exist for transmission power. Standards that have been made regarding RFID include: ISO 14223—Radiofrequency [sic] identification of animals—Advanced transponders: ISO/IEC 14443: This standard is a popular HF (13.56 MHz) standard for HighFIDs which is being used as the basis of RFID-enabled passports under ICAO 9303. The Near Field Communication standard that lets mobile devices act as RFID readers/transponders is also based on ISO/IEC 14443. ISO/IEC 15693: This is also a popular HF (13.56 MHz) standard for HighFIDs widely used for non-contact smart payment and credit cards.

ISO/IEC 18000: Information technology—Radio frequency identification for item management includes the following standards: Part 1: Reference architecture and definition of parameters to be standardized; Part 2: Parameters for air interface communications below 135 kHz; Part 3: Parameters for air interface communications at 13.56 MHz; Part 4: Parameters for air interface communications at 2.45 GHz; Part 6: Parameters for air interface communications at 860-960 MHz; Part 7: Parameters for active air interface communications at 433 MHz; Other standards include: ISO/IEC 18092 Information technology—Telecommunications and information exchange between systems—Near Field Communication—Interface and Protocol (NFCIP-1); ISO 18185: This is the industry standard for electronic seals or "e-seals" for tracking cargo containers using the 433 MHz and 2.4 GHz frequencies; ISO/IEC 21481 Information technology—Telecommunications and information exchange between systems—Near Field Communication Interface and Protocol-2 (NFCIP-2); ASTM D7434, Standard Test Method for Determining the Performance of Passive Radio Frequency Identification (RFID) Transponders on Palletized or Unitized Loads; ASTM D7435, Standard Test Method for Determining the Performance of Passive Radio Frequency Identification (RFID) Transponders on Loaded Containers; ASTM D7580, Standard Test Method for Rotary Stretch Wrapper Method for Determining the Readability of Passive RFID Transponders on Homogenous Palletized or Unitized Loads; and ISO 28560-2: specifies encoding standards and data model to be used within libraries.

Description of Non-Limiting Exemplary Embodiments

Optional embodiments provide analytic measurement for products or other services or experiences or promotions via the Internet, communications, and social media content for users such as global enterprises, advertising agencies, sales and marketing departments, media companies, government agencies, financial institutions, global brands, dairy farmers, milk production and dairy products or milk products, animal farming companies, cattle farmers, industrial livestock production companies, pharmaceutical companies, merchants, retailers, and virtually any entity requiring real-time or near real-time access to such information. This frequency location and identification data transfer to a database that can be accessed by members of a network for products or other services or experiences or promotions via the Internet, communications, and social media content is quantified and provided in a relevant and user-friendly manner to these entities using a wireless interface such as a graphical user interface (GUI). These embodiments provide both historical and current measurements to enable analysis of past and present information. Frequency location and identification data transfer to a database that can be accessed by members of a network for products or other services or experiences or promotions via the Internet, communications, and social media content is collected, sorted, and provided to relevant groups or entities. Certain embodiments describe EMFID (e.g., EMFID) tracking tags analytics platform using a wireless device for detection of EMFID tracking of personal data for one or more individuals or end user that uses a higher spectrum of light, sound and electromagnetic frequency (EMF) identification (EMFID) technologies to provide data transfer and communications for EMFID sensors for automatic identification data collection of personal data for one or more individuals or end user, multiple EMFID tag communications, remotely storing, monitoring and retrieving data, location data and other data to develop a profile for one or more end user, pet, livestock, dairy cows, cattle or other animals, including tracking movement, logistics data, and/or location data using radio and other frequency tags and relaying data from EMFID tag interactions to a database that can be accessed by members of a network, physical, emotional and mental state data, integration of biometric data, healthcare, physical health conditions, medical conditions, track movement, logistics, transportation, track diseases for pets, livestock, dairy cows, cattle or other animals, diseases and conditions for disease control and prevention, monitoring antibiotics, pharmaceutical data and other data to develop a profile for one or more end user, pet, livestock, dairy cows, cattle or other animals, including tracking movement, logistics data, and/or location data using radio and other frequency tags and relaying data from EMFID tag interactions on different codes and readers to a database that can be accessed by members of a network, and readers, GPS, RTLS location tracking and mapping location data and information to identify an item being tracked and to store data on a database, EMFID communications between customers and companies, patients, retailers, global brands, dairy farmers, milk production and dairy products or milk products, animal farming companies, cattle farmers, industrial livestock production companies, pharmaceutical companies, mapping location data and information, social media communications and human behavior and other products or other services or experiences and other data, tracking to companies, organizations, and governmental agencies that can be used to increase the top-line growth and margins of its recipients. Additionally, this social media information can be analyzed to determine trends in one or more of the above discussed categories.

Monitoring and analyzing this new information source may be used on its own or in conjunction with traditional research and measurements such as, for example, quantitative and qualitative market research, paid media tracking, and traditional web site analytics. This process is automated so that qualitative measurements can be analyzed, quantified, and presented with minimal human intervention. At least certain embodiments contemplate a collecting process referred to herein as "scraping" where social media sources are discovered or located and exploited for relevant information. The content is then analyzed and quantified in a manner relevant to the industry or other category. The analyzed and quantified radio frequency location and identification data transfer to a database that can be accessed by members of a network for products or other services or experiences or promotions via the Internet, communications, and social media content is then provided to the user of the electromagnetic frequency (EMF) identification (EMFID) technologies in an efficient, timely and user-friendly manner using the interface. In one embodiment, the interface is user-specific.

Examples of the quantitative location and identification data transfer to a database that can be accessed by members of a network for products or other services or experiences or promotions via the Internet, communications, and social media content data that can be provided by embodiments include: brand product/service consumer or brand sentiment for users and their competition; the share of voice of the brand (e.g., volume of discussion about the brand, product or service) over the social media versus the competition; topics and keywords used by online discussion participants for the brand the competition; information on the opinion leaders for the category (e.g., online social content authors with the most influential voices); top websites resulting from the brand search; automated alerts for changes in consumer or brand sentiment; keywords, terms or phrases in posts to the online social media websites; and much more. This information is analyzed, quantified, and provided to users in real-time or near-real-time for the purpose of, for example, marketing, public relations, advertising, sales, customer service, brand management, product development, investor relations, and so on. The result of this process is to provide highly relevant and timely actionable wireless use of the data to provide data, tracking and analysis to companies, organizations, and governmental agencies to users of the wireless device.

This information may be advantageous for several reasons including brand product/service perception or consumer or brand sentiment analysis, trend recognition and opportunity identification, early warnings about customer service or quality issues, opinion leader identification and engagement, competitor monitoring, and optimized online advertising to name a few. This information allows users to quantify opinion on social media sites to gain insights into current consumer or brand sentiment about the users' products or other services or experiences, global brands, dairy farmers, milk production and dairy products or milk products, animal farming companies, cattle farmers, industrial livestock production companies, pharmaceutical companies & products, and technologies and those of their competitors. This information also enables users of the wireless device to recognize trends in consumer buzz about new technologies, product or service types, and attributes. In addition, users may receive early-warning signs to identify dissatisfied customers. Users also may identify and target opinion leaders for a given product/service or category using this information. Embodiments can also supplies users with a list of highly relevant websites where high-affinity users are exchanging opinions and making purchasing decisions. This information can also be made widely available inside users' organizations using a wireless interface to push analytics to potentially everyone inside the organization instead of just the top-level marketing staff enabling entire organizations to establish an overall better sense of the voice of their customers and to make informed decisions at the customer level because embodiments focus on the social behavior of potential customers using online user online activity and social media sources and provide far better insight into commercially relevant interests.

The present developments provide in one aspect a system and method for providing actionable frequency identification including inventory and other data, tracking, surveillance, consumer sentiments on products or other services or experiences, EMFID communications between customers and companies, patients, retailers, global brands, dairy farmers, milk production and dairy products or milk products, animal farming companies, cattle farmers, industrial livestock production companies, pharmaceutical companies & products or other services or experiences or promotions, to companies, organizations, and/or governmental agencies, to provide location-based promotions or offers, targeted, actionable information using combined technologies for communications using tracking, predictive analytics, and implementing online user/consumer behavior information or internet activity across the web or in conjunction with social networking, for global brands, dairy farmers, milk production and dairy products or milk products, animal farming companies, cattle farmers, industrial livestock production companies, pharmaceutical companies and branding, and promoting or selling products or other services or experiences, optionally on a mapping display, to provide Location-Based promotions or offers EMFID Tracking or monitoring EMFID Tags for Global Products or other services or experiences based on Real-Time Location System on Human Behavior and Location and Social Networking ("LBTT-GPS, RTLS-HBL-SN").

The use of EMFID tag interactions, web mapping, mapping location data and information, GPS, RTLS, location mapping, social mapping, digital mapping, 3D holographic mapping and/or mobile mapping technologies with for associating information to specific places can included, but it not limited to, one or more of: Live links to places and events; Data on the landscape; Zoom to birds-eye and human scale ad view EMFID tag communications; 3D custom audio/visual content marketing EMFID tag communications; Interactive 360 panoramas; Fly-through tours with content marketing EMFID tag communications, narration, music; Stunning imagery and videos; 3D buildings and landscaping, e-commerce and mobile banking tools and hooks; Advertising on the landscape; Advanced search for private and public information; Social shopping and social networking, social networking communications between members and generate marketing and mapping relationships between members of a social network or website, social networking websites or third party websites or applications; Self-posting for uploading user generated content marketing EMFID tag communications; Custom tools, mobile and EMFID tag communications, mobile products EMFID tag communications, mobile app EMFID tag communications, social business app EMFID tag communications, social enterprise app EMFID tag communications, third party app EMFID tag communications, mobile ad products, targeted mobile ad EMFID tag communications, mobile advertising network for mobile publishers and advertisers EMFID tag communications, mobile user's location, phone brand, model and retail price EMFID tag communications and widgets; and the like. Connecting buyers and sellers with EMFID, GPS, RTLS and mapping location data and information to identify an item being tracked and to store data on a database, EMFID communications between customers and companies, patients, retailers, global brands, dairy farmers, milk production and dairy products or milk products, animal farming companies, cattle farmers, industrial livestock production companies, pharmaceutical companies, mapping location data and information, social media communications and human behavior and other information for products or other services or experiences or promotions.

The present developments thus provide any known alternative geo-tagging, real-time geo-tagging, geo-coding, geo-targeted, geo-location EMFID tag communications, mobile geo-tagging, geo-fencing, mobile mapping technologies with LBP, LBDDD, LBA, LBDO & LBS services, GPS, RTLS and GIS technologies, and the like, in the location-based promotions, location-based offers, location-based information, social media content, promotions or offers in connection with an online EMFID tag or mobile EMFID tag, location-based advertising, mobile location-based advertising and promotions or offers and marketing EMFID tag communications and online or mobile coupons and promotions or offers for online or mobile coupons and promotions or offers for products or other services or experiences or promotions, EMFID, GPS, RTLS and mapping location data and information to identify an item being tracked and to store data on a database, EMFID communications between customers and companies, patients, retailers, global brands, dairy farmers, milk production and dairy products or milk products, animal farming companies, cattle farmers, industrial livestock production companies, pharmaceutical companies, mapping location data and information, social media communications and human behavior and other information, which are accessible across one or multiple websites or third party applications with two or three dimensional images on EMFID tag interactions platform using cloud-type configuration and using cloud services in combination with geo-mapping and mobile mapping technologies with social, local, mobile search, mobile services, mobile location-based advertising and promotions' or offers.

The present developments also provides alternative affiliated promotion or offer or advertising functions, components, and systems, including, but not limited to: one or more of, (1) advertising content management system and method; (2) advertising method and product; (3) affiliate distribution of geo-target geo-targeted or geo-tagged advertisements and/or location-based promotions, location-based offers, location-based information, social media content, promotions or offers in connection with an online EMFID tag or mobile EMFID tag and with compensation for affiliate; (4) affiliate system and affiliate device; (5) affiliate system on social networking or social networking websites or third party websites or applications; (6) affiliated advertising widget; (7) apparatus and method for internet advertising compensation; (8) apparatus, method and article to evaluate affiliate performance; (9) arranging delivery of geo-tagging, real-time geo-tagging, geo-coding, geo-targeted, geo-location EMFID tag communications, mobile geo-tagging, geo-fencing, mobile mapping technologies with LBP, LBDDD, LBA, LBDO & LBS services, GPS, RTLS and GIS technologies, and the like, in the location-based promotions, location-based offers, location-based information, social media content, promotions or offers in connection with an online EMFID tag or mobile EMFID tag, position-based services, location-based advertising, mobile location-based advertising and promotions or offers and marketing EMFID tag communications and online or mobile coupons and promotions or offers for online or mobile coupons and promotions or offers for Products, and/or other services, which are accessible across one or multiple websites or third party applications with two or three dimensional images on EMFID tag interactions on different codes and readers platform using cloud-type configuration and using cloud services in combination with geo-mapping and mobile mapping technologies with social, local, mobile search, mobile services, mobile location-based advertising and promotions' or offers' EMFID tag communications, mobile social networking EMFID tag communications, location-based mobile ads, mobile ad network, mobile advertising for mobile publishers and advertisers and mobile commerce, mobile location-based advertising and promotions or offers associated with location or maps in a social network or website online or mobile device, location-based mobile coupons, mobile grocery coupons, mobile and EMFID tag communications, mobile products EMFID tag communications, mobile app EMFID tag communications, social business app EMFID tag communications, social enterprise app EMFID tag communications, third party app EMFID tag communications, mobile ad products, targeted mobile ad EMFID tag communications, mobile advertising network for mobile publishers and advertisers EMFID tag communications, mobile user's location, phone brand, model and retail price EMFID tag communications, and mobile coupons, mobile grocery coupons, mobile banking and mobile wallet services, customer loyalty cards, discounts and promotions or offers and online or mobile payment system for coupons, location-based promotions, location-based offers, location-based information, social media content, promotions or offers in connection with an online EMFID tag or mobile EMFID tag and online or mobile coupons and promotions or offers for products and/or other services, of interest, of past, present or future customers, users, targets and/or target markets.

Figure 5:
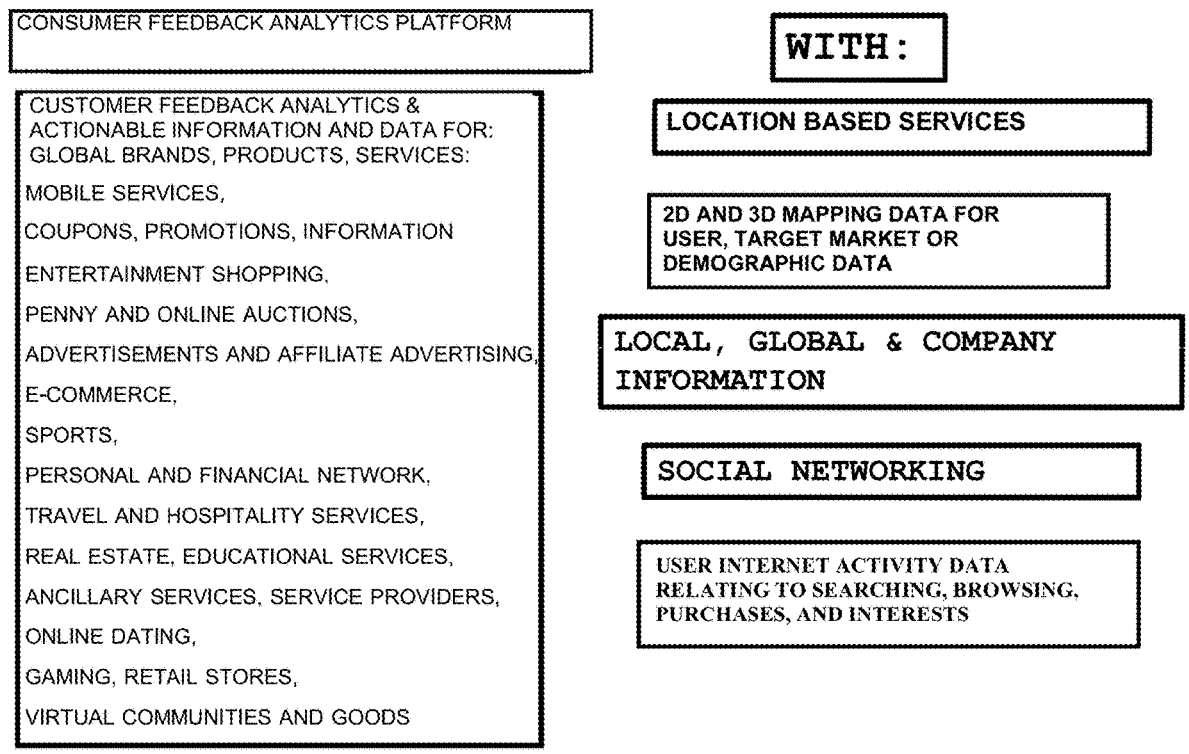
FIG. 5 provides tables showing types of location-based user customized online promotions or offers that can be used with EMFID device communications.

As presented in FIG. 5, the present developments provide in one aspect a delivery system for providing, using, and using delivering advertising search impressions consumer feedback frequency identification social analytics platform to advertisers brands provide actionable data in evaluating and other third parties for improving consumer perception of products, services or experiences, or experiences or promotions thereof, in order to generate to provide data transfer and communications for tracking of EMFID communications, security, routing, analysis, storage, access and retrieval using a wireless device for detection of EMFID tracking of personal data for one or more individuals or end user that uses a higher spectrum of light, sound and electromagnetic frequency (EMF) identification (EMFID) technologies for multiple EMFID tag communications enabled objects, EMFID labels of pharmaceutical products, electronic product code (EPC), EMFID inventory tracking, EMFID logistic applications, animal identification, garment EMFID Inventory Management System (GIMS), EMFID chip vaccinations and/or embedded in any physical objects, including without limitation, EMFID edible drugs, Medical EMFID card with prescription, EMFID labels of pharmaceutical products, electronic product code (EPC), EMFID inventory tracking, EMFID logistic applications, animal identification, Garment EMFID Inventory Management System (GIMS), EMFID chip vaccinations, EMFID packaging, EMFID passports, EMFID credit cards, EMFID debit cards, other forms of EMFID payment systems, EMFID travel cards, edible EMFID tags, EMFID navigation systems, EMFID vehicle tags, EMFID retail, EMFID clothing, EMFID pharma/healthcare, EMFID merchandise, EMFID smart dust, EMFID mobile devices, EMFID wireless devices, EMFID international mobile equipment identity (IMEI), other EMFID wireless or EMFID handheld devices, computers, PCs, currency, identification cards, products or other services or experiences and/or EMFID microchip and/or nanobots implant subdermal in animals and/or individuals for feedback tracking or monitoring EMFID tags that companies and others can use to provide global brands, dairy farmers, milk production and dairy products or milk products, animal farming companies, cattle farmers, industrial livestock production companies, pharmaceutical chain online information and targeted marketing of location-based promotions, location-based offers, location-based information, social media content, promotions or offers in connection with an online or mobile news feed connection with an online EMFID tag or mobile EMFID tag, position-based services, location-based advertising, mobile location-based advertising and promotions or offers and marketing impressions EMFID tag communications for EMFID tag interactions website for a multidimensional representation of information and/or scalable versions of web and mobile device content marketing impressions EMFID tag communications for an infrastructure and global platform that provides users or members and businesses of all types and sizes with access to broad markets for the delivery of delivering advertising search impressions EMFID tag communications to advertisers brands and other third parties for online marketing of location-based promotions, location-based offers, location-based information, social media content, promotions or offers in connection with an online or mobile news feed connection with an online EMFID tag or mobile EMFID tag, location-based advertising, mobile location-based advertising and promotions or offers and marketing impressions EMFID tag communications, coupons and/or location-based deals and offers and location-based services in real-time via a mobile device geo-tagging, real-time geo-tagging, geo-coding, geo-targeted, geo-location impressions EMFID tag communications, mobile geo-tagging, geo-fencing, mobile mapping technologies with location-based advertisements, location-based deals and offers, social networking, social networking communications between members and generate marketing and mapping relationships between members of a social network or website and social networking websites or third party websites or applications, location impression-based services, GPS, RTLS and GIS technologies, and the like, social, local, mobile search, mobile services, mobile location-based advertising and promotions' or offers' impressions EMFID tag communications, mobile social networking impressions EMFID tag communications, location-based mobile ads, mobile ad network, mobile advertising for mobile publishers and advertisers and mobile commerce, mobile location-based advertising and promotions or offers associated with location or maps in a social network or website online or mobile device, location-based mobile coupons, mobile grocery coupons, mobile and impressions EMFID tag communications, mobile products impressions EMFID tag communications, mobile app impressions EMFID tag communications, social business app EMFID tag communications, social enterprise app EMFID tag communications, third party app EMFID tag communications, mobile ad products, targeted mobile ad EMFID tag communications, mobile advertising network for mobile publishers and advertisers EMFID tag communications, mobile user's location, phone brand, model and retail price EMFID tag communications, and mobile coupons, mobile grocery coupons, mobile banking and mobile wallet services, customer loyalty cards, discounts and promotions or offers and online or mobile payment system for coupons, location-based promotions, location-based offers, location-based information, social media content, promotions or offers in connection with an online EMFID tag or mobile EMFID tag and online or mobile coupons and promotions or offers for products and/or other services, social shopping and social networking, social networking communications between members and generate marketing and mapping relationships between members of a social network or website, social networking websites or third party websites or applications, EMFID, GPS, RTLS and mapping location data and information to identify an item being tracked and to store data on a database, EMFID communications between customers and companies, patients, retailers, global brands, dairy farmers, milk production and dairy products or milk products, animal farming companies, cattle farmers, industrial livestock production companies, pharmaceutical companies, mapping location data and information, social media communications and human behavior and other information online or mobile coupons and promotions or offers for products or other services or experiences or promotions, and/or other services from advertisers, brands, and/or merchants from around the world.

Embodiments provide analytic measurement for products or other services or experiences or promotions via the Internet, communications, and social media content for users such as global enterprises, advertising agencies, sales and marketing departments, media companies, government agencies, financial institutions, global brands, dairy farmers, milk production and dairy products or milk products, animal farming companies, cattle farmers, industrial livestock production companies, merchants, retailers, and virtually any entity requiring real-time or near real-time access to such information. This frequency location and identification data transfer to a database that can be accessed by members of a network for products or other services or experiences or promotions via the Internet, communications, and social media content is quantified and provided in a relevant and user-friendly manner to these entities using a wireless interface such as a graphical user interface (GUI). These embodiments provide both historical and current measurements to enable analysis of past and present information. Frequency location and identification data transfer to a database that can be accessed by members of a network for products or other services or experiences or promotions via the Internet, communications, and social media content is collected, sorted, and provided to relevant groups or entities. Certain embodiments describe EMFID tracking tags analytics platform using a wireless device for detection of EMFID tracking of personal data for one or more individuals or end user that uses a higher spectrum of light, sound and electromagnetic frequency (EMF) identification (EMFID) technologies to provide data transfer and communications for EMFID sensors for automatic identification data collection of personal data for one or more individuals or end user, multiple EMFID tag communications, remotely storing, monitoring and retrieving data, location data and other data to develop a profile for one or more end user, pet, livestock, dairy cows, cattle or other animals, including tracking movement, logistics data, and/or location data using radio and other frequency tags and relaying data from EMFID tag interactions to a database that can be accessed by members of a network, physical, emotional and mental state data, integration of biometric data, healthcare, physical health conditions, medical conditions, track movement, logistics, transportation, track diseases for pets, livestock, dairy cows, cattle or other animals, diseases and conditions for disease control and prevention, monitoring antibiotics, pharmaceutical data and other data to develop a profile for one or more end user, pet, livestock, dairy cows, cattle or other animals, including tracking movement, logistics data, and/or location data using radio and other frequency tags and relaying data from EMFID tag interactions to a database that can be accessed by members of a network, and readers, scalar electromagnetic fields, radio frequency (RF) or Wi-Fi frequency ranges not current used, EMFID applicable hardware or software EMFID for real-time tracking of EMFID communications, security, routing, analysis, storage, access, and retrieval collecting and converting raw radio frequency location and identification data transfer to a database that can be accessed by members of a network for products or other services or experiences or promotions via the Internet, communications, and social media content into actionable wireless use of electromagnetic fields, radio frequency (RF) or Wi-Fi frequency ranges EMFID, EMFID hardware or software EMFID, electromagnetic fields EMFID to provide data transfer for real-time tracking of EMFID communications, security, routing, analysis, storage, access and retrieval using a wireless device for detection of EMFID tracking of personal data for one or more individuals or end user that uses a higher spectrum of light, sound and electromagnetic frequency (EMF) identification (EMFID) technologies for multiple EMFID tag communications enabled objects, EMFID labels of pharmaceutical products, electronic product code (EPC), EMFID inventory tracking, EMFID logistic applications, animal identification, Garment EMFID Inventory Management System (GIMS), EMFID chip vaccinations and/or embedded in any physical objects, including without limitation, EMFID edible drugs, Medical EMFID card with prescription, EMFID labels of pharmaceutical products, electronic product code (EPC), EMFID inventory tracking, EMFID logistic applications, animal identification, Garment EMFID Inventory Management System (GIMS), EMFID chip vaccinations, EMFID packaging, EMFID passports, EMFID credit cards, EMFID debit cards, other forms of EMFID payment systems, EMFID travel cards, edible EMFID tags, EMFID navigation systems, EMFID vehicle tags, EMFID retail, EMFID clothing, EMFID pharma/healthcare, EMFID merchandise, EMFID smart dust, EMFID mobile devices, EMFID wireless devices, EMFID international mobile equipment identity (IMEI), other EMFID wireless or EMFID handheld devices, computers, PCs, currency, identification cards, products or other services or experiences and/or EMFID microchip and/or nanobots implant subdermal in animals and/or individuals using EMFID tags electromagnetic frequency (EMF) identification (EMFID) technologies to provide data transfer and communications for EMFID sensors for automatic identification data collection of personal data for one or more individuals or end user, multiple EMFID tag communications, remotely storing, monitoring and retrieving data, location data and other data to develop a profile for one or more end user, pet, livestock, dairy cows, cattle or other animals, including tracking movement, logistics data, and/or location data using radio and other frequency tags and relaying data from EMFID tag interactions to a database that can be accessed by members of a network, physical, emotional and mental state data, integration of biometric data, healthcare, physical health conditions, medical conditions, track movement, logistics, transportation, track diseases for pets, livestock, dairy cows, cattle or other animals, diseases and conditions for disease control and prevention, monitoring antibiotics, pharmaceutical data and other data to develop a profile for one or more end user, pet, livestock, dairy cows, cattle or other animals, including tracking movement, logistics data, and/or location data using radio and other frequency tags and relaying data from EMFID tag interactions to a database that can be accessed by members of a network, and readers, GPS, RTLS location tracking and mapping location data and information to identify an item being tracked and to store data on a database, EMFID communications between customers and companies, patients, retailers, global brands, dairy farmers, milk production and dairy products or milk products, animal farming companies, cattle farmers, industrial livestock production companies, pharmaceutical companies, mapping location data and information, social media communications and human behavior and other products or other services or experiences and other data, tracking to companies, organizations, and governmental agencies that can be used to increase the top-line growth and margins of its recipients. Additionally, this analysis of social media information can be analyzed to determine trends in one or more of the above discussed categories.

Monitoring and analyzing this new information source may be used on its own or in conjunction with traditional research and measurements such as, for example, quantitative and qualitative market research, paid media tracking, and traditional web site analytics. This process is automated so that qualitative measurements can be analyzed, quantified, and presented with minimal human intervention. At least certain embodiments contemplate a collecting process referred to herein as "scraping" where social media sources are discovered or located and exploited for relevant information. The content is then analyzed and quantified in a manner relevant to the industry or other category. The analyzed and quantified radio frequency location and identification data transfer to a database that can be accessed by members of a network for products or other services or experiences or promotions via the Internet, communications, and social media content is then provided to the user of the electromagnetic frequency (EMF) identification (EMFID) technologies in an efficient, timely and user-friendly manner using the interface. In one embodiment, the interface is user-specific.

Examples of the quantitative location and identification data transfer to a database that can be accessed by members of a network for products or other services or experiences or promotions via the Internet, communications, and social media content data that can be provided by embodiments include: brand product/service consumer or brand sentiment for users and their competition; the share of voice of the brand (e.g., volume of discussion about the brand, product or service) over the social media versus the competition; topics and keywords used by online discussion participants for the brand the competition; information on the opinion leaders for the category (e.g., online social content authors with the most influential voices); top websites resulting from the brand search; automated alerts for changes in consumer or brand sentiment; keywords, terms or phrases in posts to the online social media websites; and much more. This information is analyzed, quantified, and provided to users in real-time or near-real-time for the purpose of, for example, marketing, public relations, advertising, sales, customer service, brand management, product development, investor relations, and so on. The result of this process is to provide highly relevant and timely actionable wireless use of electromagnetic fields, radio frequency (RF) or Wi-Fi frequency ranges EMFID, EMFID hardware or software EMFID, electromagnetic fields EMFID to provide data transfer for real-time tracking of EMFID communications, security, routing, analysis, storage, access and retrieval using a wireless device for detection of EMFID tracking of personal data for one or more individuals or end user that uses a higher spectrum of light, sound and electromagnetic frequency (EMF) identification (EMFID) technologies for multiple EMFID tag communications enabled objects, EMFID labels of pharmaceutical products, electronic product code (EPC), EMFID inventory tracking, EMFID logistic applications, animal identification, Garment EMFID Inventory Management System (GIMS), EMFID chip vaccinations and/or embedded in any physical objects, including without limitation, EMFID edible drugs, Medical EMFID card with prescription, EMFID labels of pharmaceutical products, electronic product code (EPC), EMFID inventory tracking, EMFID logistic applications, animal identification, Garment EMFID Inventory Management System (GIMS), EMFID chip vaccinations, EMFID packaging, EMFID passports, EMFID credit cards, EMFID debit cards, other forms of EMFID payment systems, EMFID travel cards, edible EMFID tags, EMFID navigation systems, EMFID vehicle tags, EMFID retail, EMFID clothing, EMFID pharma/healthcare, EMFID merchandise, EMFID smart dust, EMFID mobile devices, EMFID wireless devices, EMFID international mobile equipment identity (IMEI), other EMFID wireless or EMFID handheld devices, computers, PCs, currency, identification cards, products or other services or experiences and/or EMFID microchip and/or nanobots implant subdermal in animals and/or individuals using EMFID tags electromagnetic frequency (EMF) identification (EMFID) technologies to provide data transfer and communications for EMFID sensors for automatic identification data collection of personal data for one or more individuals or end user, multiple EMFID tag communications, remotely storing, monitoring and retrieving data, location data and other data to develop a profile for one or more end user, pet, livestock, dairy cows, cattle or other animals, including tracking movement, logistics data, and/or location data using radio and other frequency tags and relaying data from EMFID tag interactions to a database that can be accessed by members of a network, physical, emotional and mental state data, integration of biometric data, healthcare, physical health conditions, medical conditions, track movement, logistics, transportation, track diseases for pets, livestock, dairy cows, cattle or other animals, diseases and conditions for disease control and prevention, monitoring antibiotics, pharmaceutical data and other data to develop a profile for one or more end user, pet, livestock, dairy cows, cattle or other animals, including tracking movement, logistics data, and/or location data using radio and other frequency tags and relaying data from EMFID tag interactions to a database that can be accessed by members of a network, and readers, GPS, RTLS location tracking and mapping location data and information to identify an item being tracked and to store data on a database, EMFID communications between customers and companies, patients, retailers, global brands, dairy farmers, milk production and dairy products or milk products, animal farming companies, cattle farmers, industrial livestock production companies, pharmaceutical companies, mapping location data and information, social media communications and human behavior and other products or other services or experiences and other data, tracking to companies, organizations, and governmental agencies to users of the wireless device.

This information may be advantageous for several reasons including brand product/service perception or consumer or brand sentiment analysis, trend recognition and opportunity identification, early warnings about customer service or quality issues, opinion leader identification and engagement, competitor monitoring, and optimized online advertising to name a few. This information allows users to quantify opinion on social media sites to gain insights into current consumer or brand sentiment about the users' products or other services or experiences, global brands, dairy farmers, milk production and dairy products or milk products, animal farming companies, cattle farmers, industrial livestock production companies, pharmaceutical companies & products, and technologies and those of their competitors. This information also enables users of the wireless device to recognize trends in consumer buzz about new technologies, product or service types, and attributes. In addition, users may receive early-warning signs to identify dissatisfied customers. Users also may identify and target opinion leaders for a given product/service or category using this information. Embodiments of the EMFID Tracking Analytics can also supplies users with a list of highly relevant websites where high-affinity users are exchanging opinions and making purchasing decisions. This information can also be made widely available inside users' organizations using a wireless interface to push analytics to potentially everyone inside the organization instead of just the top-level marketing staff enabling entire organizations to establish an overall better sense of the voice of their customers and to make informed decisions at the customer level because embodiments focus on the social behavior of potential customers using online user online activity and social media sources and provide far better insight into commercially relevant interests.

Figure 6:
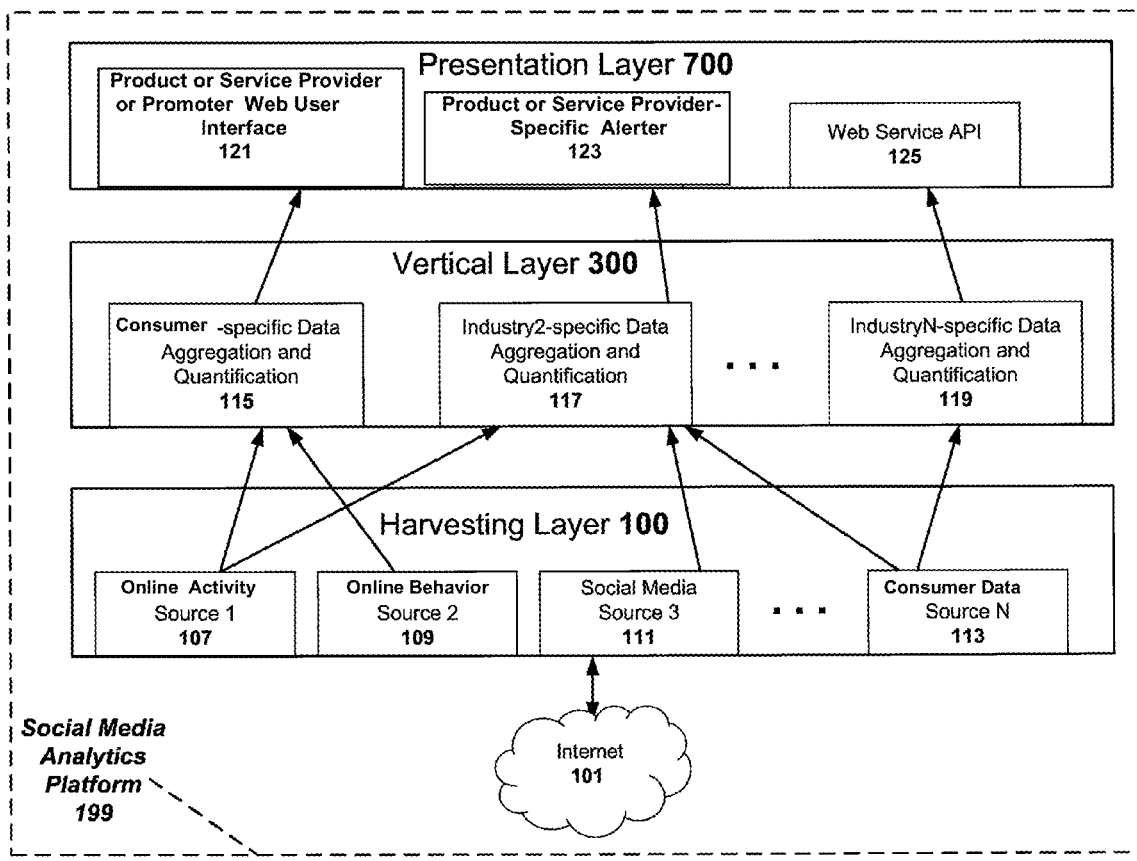
FIG. 6 illustrates a block diagram\m of electromagnetic frequency (EMF) identification (EMFID) technologies analytics, such as, but not limited, social media analytics according to an exemplary embodiment hereof.

FIG. 6 illustrates a block diagram of electromagnetic frequency (EMF) identification (EMFID) technologies according to an exemplary embodiment hereof. In the illustrated embodiment, the INVENTION 199 is separated into three layers or phases—the collecting layer 100, vertical layer 300 and presentation layer 700. The collecting layer 100 includes locating or discovering online activity, behavior, location, diagnosis and social media sources (e.g., websites) from the Internet related to a particular industry or other category, and collecting the relevant content from those sources. The collecting layer may process the relevant content from these Internet sources at any frequency such as daily, hourly, weekly, and minute-by-minute. The vertical layer includes analyzing and electronically quantifying on a computer system, network or system using a wireless device for detection of EMFID tracking of personal data for one or more individuals or end user that uses processors the collected social media content, and the presentation layer includes a user interface to display the quantified radio frequency location and identification data transfer to a database that can be accessed by members of a network for products or other services or experiences or promotions via the Internet, communications, and social media content as an alerted to alert users of the EMFID Tracking Analysis platforms 199 in a real-time or near real-time manner when changes occur in consumer or brand sentiment. The basic structure includes data collection and storage for products or other services or experiences or promotions via the Internet, communications, and social media content for specific industries or other categories. The data collection and storage for products or other services or experiences or promotions via the Internet, communications, and social media content may be performed for any type of category or product line.

The collecting layer 100 of FIG. 6 includes online user online activity and social media sources discovered or located on the Internet 101 including online activity source 1_107, online behavior source 2_109, social media source 3_111, and so on through consumer data source N_113. Vertical layer 300 of a Frequency identification Social Media Analysis (FI-TTA) platforms 199 is where the radio frequency location and identification data transfer to a database that can be accessed by members of a network for products or other services or experiences or promotions via the Internet, communications, and social media content relevant to each industry is analyzed, quantified, and stored in a database. In the illustrated embodiment, Product/Service-specific data analysis and quantification 115 receives content from online activity source 1_107 and online behavior source 2_109 of collecting layer 109, Industry-specific data analysis and quantification 117 receives content from online activity source 1_107, social media source 3_111, and consumer data source N_113, and Category-specific data analysis and quantification 119 receives content from consumer data source N_113. For every identified source, relevant frequency location and identification data transfer to a database that can be accessed by members of a network for products or other services or experiences or promotions via the Internet, communications, and social media content and is retrieved and processed.

The vertical layer 300 stores the analyzed and quantified radio frequency location and identification data transfer to a database that can be accessed by members of a network for products or other services or experiences or promotions via the Internet, communications, and social media content in a database and supplies the content to the presentation layer 700 for display. Presentation layer 700 of FIG. 6 includes product/service-specific web user interface 121 for display of the analyzed and quantified radio frequency location and identification data transfer to a database that can be accessed by members of a network for products or other services or experiences or promotions via the Internet, communications, and social media content received from vertical layer 300. Presentation layer 700 also includes a web service application-programming interface (API) to provide fully automatic identification data integration into third-party analytics or data presentation systems, and a product/service-specific alerter 123 to provide alerts relating to changes in online social media consumer or brand sentiment. The product/service-specific alerter 123 may be tailored for each user of the INVENTION platform 199.

Figure 7:
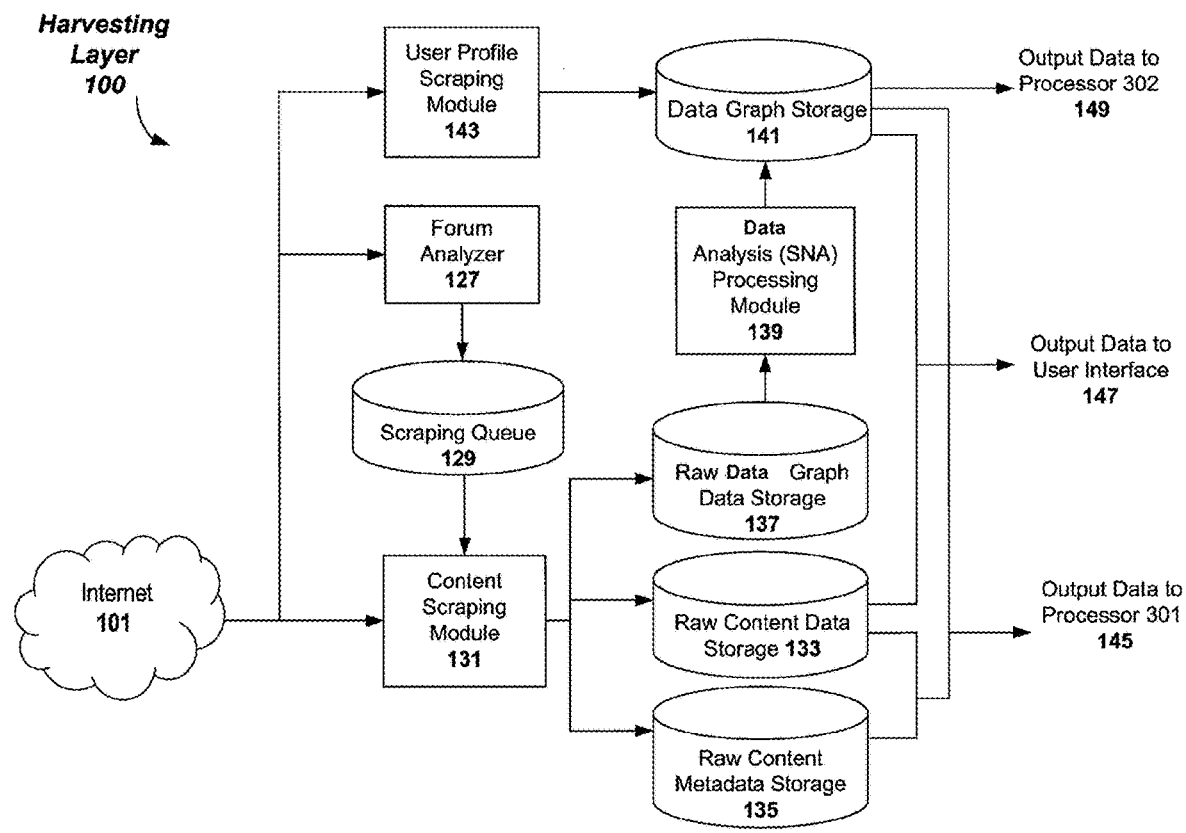
FIG. 7 illustrates a block diagram of the collecting personal data and location data according to an exemplary embodiment hereof.
Figure 8:
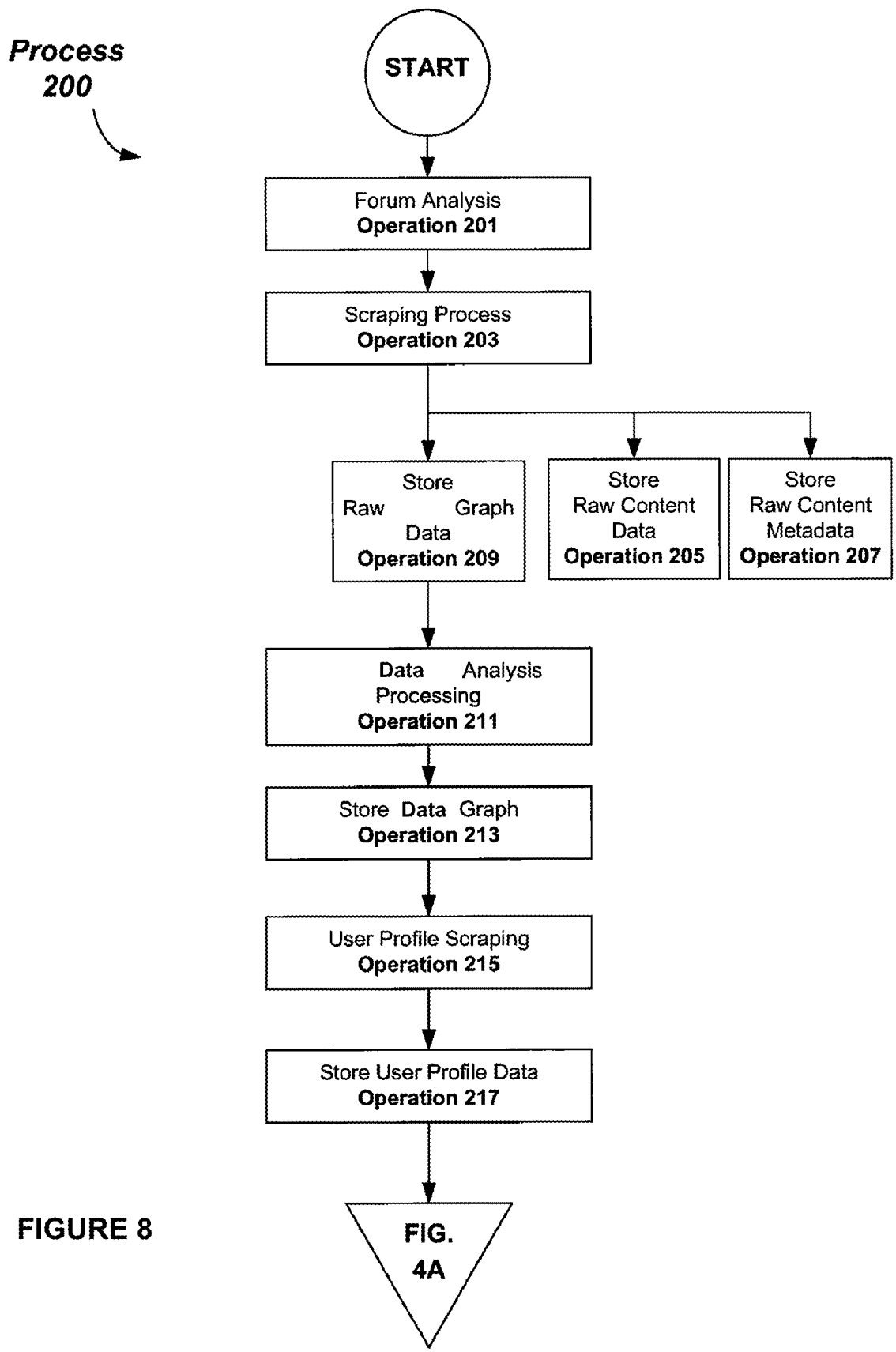
FIG. 8 illustrates collecting personal data and location data of one or more individuals processing according to an exemplary embodiment hereof.

FIG. 7 illustrates a block diagram of the collecting layer according to an exemplary embodiment hereof. As discussed above, the collecting layer 100 locates frequency location and identification data transfer to a database that can be accessed by members of a network for products or other services or experiences or promotions via the Internet, communications, and social media content sources on the Internet and collects relevant content from them. The block diagram components of the collecting layer 100 will be discussed in conjunction with process 200 of FIG. 8, which illustrates collecting layer processing according to an exemplary embodiment. Process 200 begins with performing forum analysis using forum analyzer 127 (operation 201).

The function of the forum analyzer 127 is to scour the Internet 101 searching for frequency location and identification data transfer to a database that can be accessed by members of a network for products or other services or experiences or promotions via the Internet, communications, and social media content (threads) relevant to a particular industry, product/service or other category. In at least certain embodiments, the forum analyzer 127 accomplishes this using automated tools for identifying industry-specific social media data sources from which to collect information and provide to the users of the wireless device platform. This includes a forum analysis to locate or discover which forums and/or sub-forums are relevant to a specific user's industry or other category from which the radio frequency location and identification data transfer to a database that can be accessed by members of a network for products or other services or experiences or promotions via the Internet, communications, and social media content should be collected. To accomplish this, search results from publicly available online search engines are processed to determine relevant websites based on the relevance score of each site for the keywords of interest. Each website found through this process is then accessed by the system to determine structural properties such as the technical nature of the source (e.g., RSS feeds, certain discussion forum software packages) and to identify the entry page locations later used in the content scraping module 131. The radio frequency location and identification data transfer to a database that can be accessed by members of a network for products or other services or experiences or promotions via the Internet, communications, and social media content sources that are identified in this operation are then staged in the scraping queue 129 to feed the content scraping module 131 for the scraping process (operation 203).

At operation 203 the scraping process is performed including scouring the identified online user online activity and social media sources for online communications and activity relevant to a particular sector or other category and breaking down the content into pieces to be stored for later processing. The scraping process starts at an overview page typically provided by each social media source and identifies hyperlinks to potentially relevant subpages and content pages based on the structural properties of these hyperlinks. The process then iteratively drills down multiple levels of subpages in the same manner until a specific relevant discussion thread is found. Each discussion thread is then analyzed in order to isolate its atomic content components for further processing. For example, a particular relevant social media source (e.g., website) may have a web page with a thread containing 20 varying posts relating to the Audi A6 automobile. In such a case, the web page would be retrieved and broken apart into 20 pieces, with each piece stored individually along with the user-profile information of the authors who posted the content.

The results of the scraping process include: the raw online communications and activity of each social media post referred to as the raw post content data; the metadata of the raw post content; and information relating to the author of each post, as well as relationships between authors, referred to as the raw EMFID graph data. The raw post content retrieved from the online user online activity and social media sources are stored in raw content storage 133 (operation 205). This includes the actual text of the relevant social media post. The raw content metadata is also stored in raw content metadata storage 135 (operation 207). The raw content metadata includes information such as the URL of the social media website, and the length, context, and time of the post. Additionally, the raw EMFID graph data is stored in raw EMFID graph data storage 137 (operation 209). This data may include the social media posts author profile data such as the author's username, demographic information, number of posts to the social media website, those responding to the author's posts, and the author's contacts.

In the illustrated embodiment, the data analysis (DN) processing is then performed on the raw EMFID graph data stored in raw EMFID graph data storage 137 (operation 211). Here, information on each author of a social media post and on those responding to the author's post is retrieved from the raw data graph storage 137 and used to data for real-time tracking of EMFID communications, security, routing, analysis, storage, access and retrieval using a wireless device for detection of EMFID tracking of personal data for one or more individuals or end user that uses a higher spectrum of light, sound and electromagnetic frequency (EMF) identification (EMFID) technologies for multiple EMFID tag communications enabled objects, EMFID labels of pharmaceutical products, electronic product code (EPC), EMFID inventory tracking, EMFID logistic applications, animal identification, Garment EMFID Inventory Management System (GIMS), EMFID chip vaccinations and/or embedded in any physical objects, including without limitation, EMFID edible drugs, Medical EMFID card with prescription, EMFID labels of pharmaceutical products, electronic product code (EPC), EMFID inventory tracking, EMFID logistic applications, animal identification, Garment EMFID Inventory Management System (GIMS), EMFID chip vaccinations, EMFID packaging, EMFID passports, EMFID credit cards, EMFID debit cards, other forms of EMFID payment systems, EMFID travel cards, edible EMFID tags, EMFID navigation systems, EMFID vehicle tags, EMFID retail, EMFID clothing, EMFID pharma/healthcare, EMFID merchandise, EMFID smart dust, EMFID mobile devices, EMFID wireless devices, EMFID international mobile equipment identity (IMEI), other EMFID wireless or EMFID handheld devices, computers, PCs, currency, identification cards, products or other services or experiences and/or EMFID microchip and/or nanobots implant subdermal in animals and/or individuals for a social graph which includes an analysis of social network information that can be useful in several contexts. For example, the social graph data may be analyzed to determine information about the author's social network including which authors are communicating about what topics, who is responding to which posts, what the related content is, and so on. The SNA processing is used to develop this information on networks of related authors and posts and to determine which authors are the most influential within these networks based on the social graph. The SNA processing first calculates a so-called centrality value for each author that expresses the author's degree of influence in a given social network. Authors that are connected to a large number of other authors and also connected to distinct sub-groups of authors are assumed to have higher influence than less well-connected authors. In order to calculate the centrality value, a version of Brands' Betweenness Centrality algorithm is applied to the raw social graph for each website. The resulting raw centrality value is then modified with the activity level of the author, i.e. the number of posts written by this person, and an importance score for the website where that author is active. Within graph theory and network analysis, there are various measures of the centrality of a vertex within a graph that determine the relative importance of a vertex within the graph. Betweenness is a centrality measure of a vertex within a graph. Vertices that occur on many shortest paths between other vertices have higher betweenness than those that do not. For instance, an influential author on a large website such as MySpace® will receive a higher influence score than the author of a little known blog. In at least one embodiment, the influence score for each author is calculated by the following formula:

Influence score=$bc*(c_a+a/p_a)*(c_p+p)$, where bc is the raw betweenness centrality value for the author;
a is the number of active authors on the website where the author is active;
p is the number of posts that the author has contributed;
$c_a$, $p_a$, and $c_p$ are correction parameters that are fine-tuned for the purposes of a specific vertical (i.e., a specific category of interest, according to methods know in the art or described herein).

The SNA processing also provides information including: the websites on which each of the social media authors have contributed; registrations in social networks; the status of influence of the authors; the author's sentiment towards a given brand, product or service; known demographic and geographic information about the authors; and trends in all of the above.

The social graph is then stored in data graph storage 141 (operation 213). An additional input into the data graph storage 141 is from user-profile scraping data accumulated from the Internet 101 using user-profile scraping module 143. At operation 215, the user profile-scraping module 143 scours the Internet 101 to find any other information about the authors of the radio frequency location and identification data transfer to a database that can be accessed by members of a network for products or other services or experiences or promotions via the Internet, communications, and social media content. Whatever information associated with the author that can be collected from the Internet 101 is collected and stored along with the social graph in data graph storage 141 (operation 217). This completes the collecting layer process 200 according to an exemplary embodiment.

Figure 9:
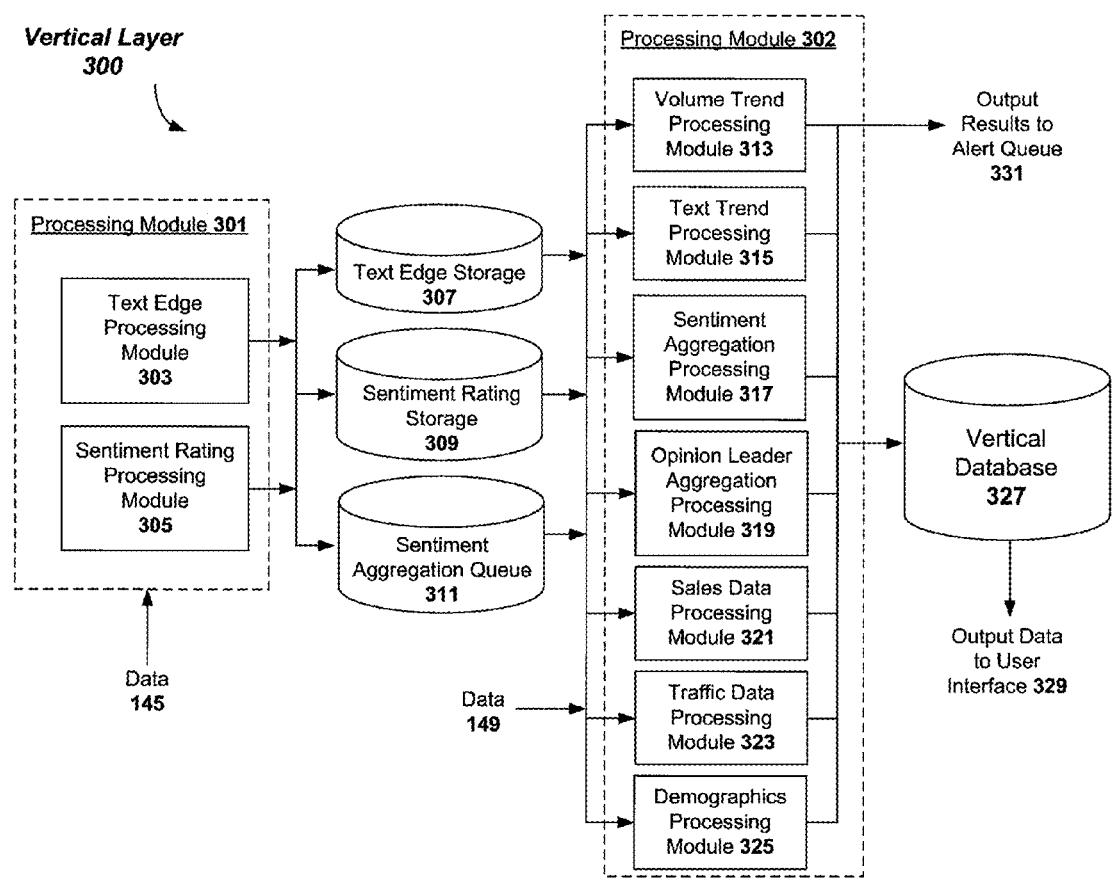
FIG. 9 illustrates a block diagram of the detection and tracking of user's data that uses electromagnetic frequency (EMF) identification (EMFID) technologies according to an exemplary embodiment hereof.

FIG. 9 illustrates a block diagram of the vertical layer according to an exemplary embodiment hereof. As discussed previously, the data collected using the scraping process 100 is fed into the vertical layer 300. The vertical layer 300 is a grouping based on sector, industry, or other category. A vertical layer may be generated for every conceivable category such as industry, topic of interest, type of website, geographic region, and so on. There is essentially no limit to the types of categories that can be collected, analyzed and quantified to provide relevant, timely and actionable wireless use of electromagnetic fields, radio frequency (RF) or Wi-Fi frequency ranges EMFID, EMFID hardware or software EMFID, electromagnetic fields EMFID to provide data transfer for real-time tracking of EMFID communications, security, routing, analysis, storage, access and retrieval using a wireless device for detection of EMFID tracking of personal data for one or more individuals or end user that uses a higher spectrum of light, sound and electromagnetic frequency (EMF) identification (EMFID) technologies for multiple EMFID tag communications enabled objects, EMFID labels of pharmaceutical products, electronic product code (EPC), EMFID inventory tracking, EMFID logistic applications, animal identification, Garment EMFID Inventory Management System (GIMS), EMFID chip vaccinations and/or embedded in any physical objects, including without limitation, EMFID edible drugs, Medical EMFID card with prescription, EMFID labels of pharmaceutical products, electronic product code (EPC), EMFID inventory tracking, EMFID logistic applications, animal identification, Garment EMFID Inventory Management System (GIMS), EMFID chip vaccinations, EMFID packaging, EMFID passports, EMFID credit cards, EMFID debit cards, other forms of EMFID payment systems, EMFID travel cards, edible EMFID tags, EMFID navigation systems, EMFID vehicle tags, EMFID retail, EMFID clothing, EMFID pharma/healthcare, EMFID merchandise, EMFID smart dust, EMFID mobile devices, EMFID wireless devices, EMFID international mobile equipment identity (IMEI), other EMFID wireless or EMFID handheld devices, computers, PCs, currency, identification cards, products or other services or experiences and/or EMFID microchip and/or nanobots implant subdermal in animals and/or individuals using EMFID tags electromagnetic frequency (EMF) identification (EMFID) technologies to provide data transfer and communications for EMFID sensors for automatic identification data collection of personal data for one or more individuals or end user, multiple EMFID tag communications, remotely storing, monitoring and retrieving data, location data and other data to develop a profile for one or more end user, pet, livestock, dairy cows, cattle or other animals, including tracking movement, logistics data, and/or location data using radio and other frequency tags and relaying data from EMFID tag interactions to a database that can be accessed by members of a network, physical, emotional and mental state data, integration of biometric data, healthcare, physical health conditions, medical conditions, track movement, logistics, transportation, track diseases for pets, livestock, dairy cows, cattle or other animals, diseases and conditions for disease control and prevention, monitoring antibiotics, pharmaceutical data and other data to develop a profile for one or more end user, pet, livestock, dairy cows, cattle or other animals, including tracking movement, logistics data, and/or location data using radio and other frequency tags and relaying data from EMFID tag interactions to a database that can be accessed by members of a network, and readers, GPS, RTLS location tracking and mapping location data and information to identify an item being tracked and to store data on a database, EMFID communications between customers and companies, patients, retailers, global brands, dairy farmers, milk production and dairy products or milk products, animal farming companies, cattle farmers, industrial livestock production companies, pharmaceutical companies, mapping location data and information, social media communications and human behavior and other products or other services or experiences and other data, tracking to companies, organizations, and governmental agencies to users of the wireless device platform. The block diagram components of the vertical layer 300 will be discussed in conjunction with process 400A of FIG. 10 and process 400B of FIG. 11.

Figure 10:
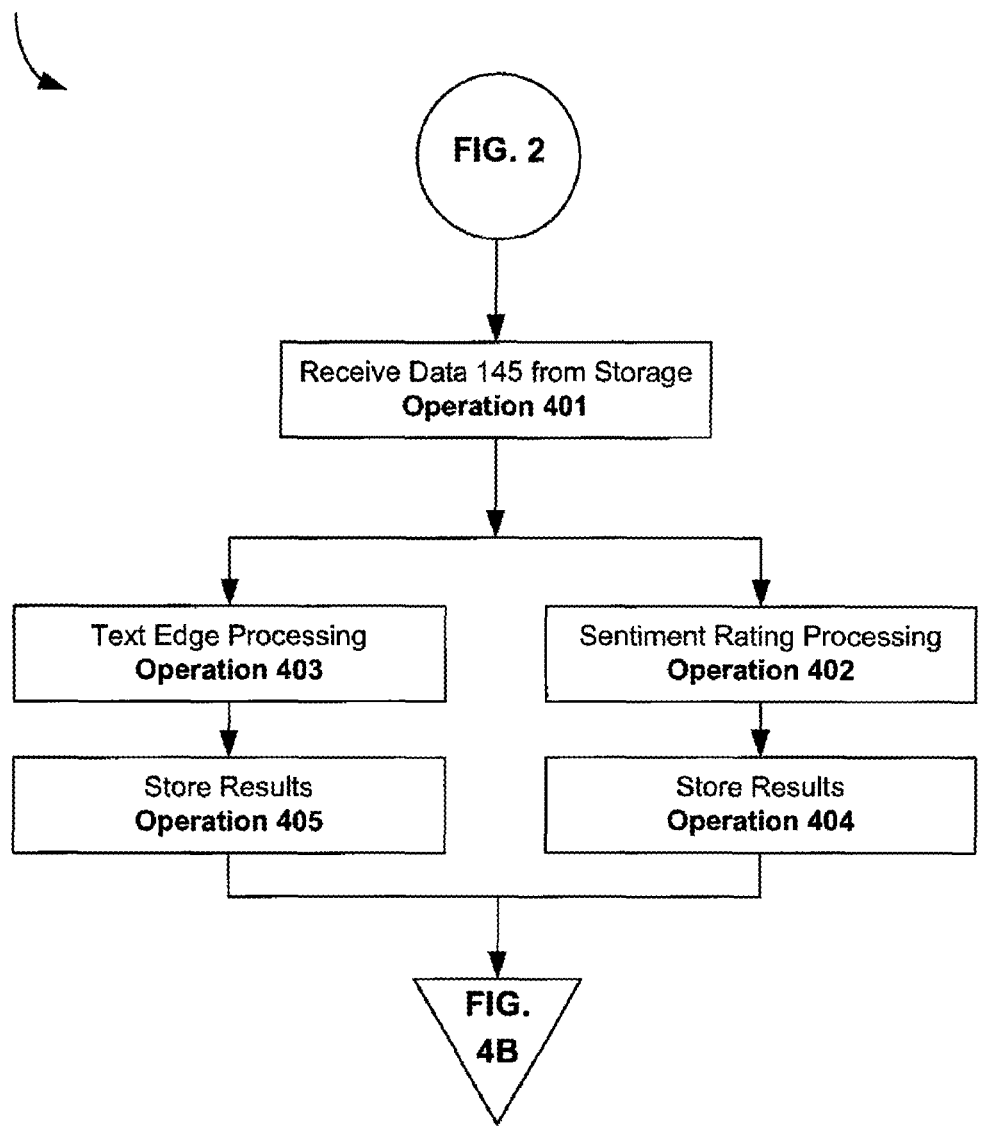
FIG. 10 illustrates data transfer and communications for EMFID sensors for automatic identification data collection processing according to an exemplary embodiment hereof.
Figure 11:
FIG. 11 illustrates multiple EMFID tag interactions and location data processing according to an exemplary embodiment hereof.

FIG. 10 illustrates vertical layer processing according to an exemplary embodiment hereof and FIG. 11 illustrates additional vertical layer processing according to an exemplary embodiment hereof. Process 400A begins with receiving data 145 at processing module 301 from storage (operation 401). The data 145 received from storage is the output data 145 including the raw content data collected from raw content data storage 133, the raw content metadata collected from raw content metadata storage 135, and the social graph data collected from data graph storage 141. Process 400A continues with performing text edge processing on the raw content data collected from raw content data storage 133 and the raw content metadata collected from raw content metadata storage 135 (operation 403). Text edge processing is performed using text edge processing module 303 of processing module 301. Text edge processing, in one embodiment, utilizes graph theory to analyze the terms and concepts contained within the radio frequency location and identification data transfer to a database that can be accessed by members of a network for products or other services or experiences or promotions via the Internet, communications, and social media content to determine the radio frequency of occurrence of these terms and concepts in conjunction with the relevant brand, product or service and the relatedness of the concepts and/or terms in the post to that brand, product or service. Relationships between these terms are analyzed to determine graph edges, which indicate the strength of these relationships. In a first step, a relevant sentence is parsed and split up into individual words and tuples of adjacent words. Stop words with little informational value such as "of," "it," "is" and so on are excluded in this step. Next, the relationship between the main term of interest (e.g., a brand, service or product name) and each found word or tuple is stored.

Figure 12:
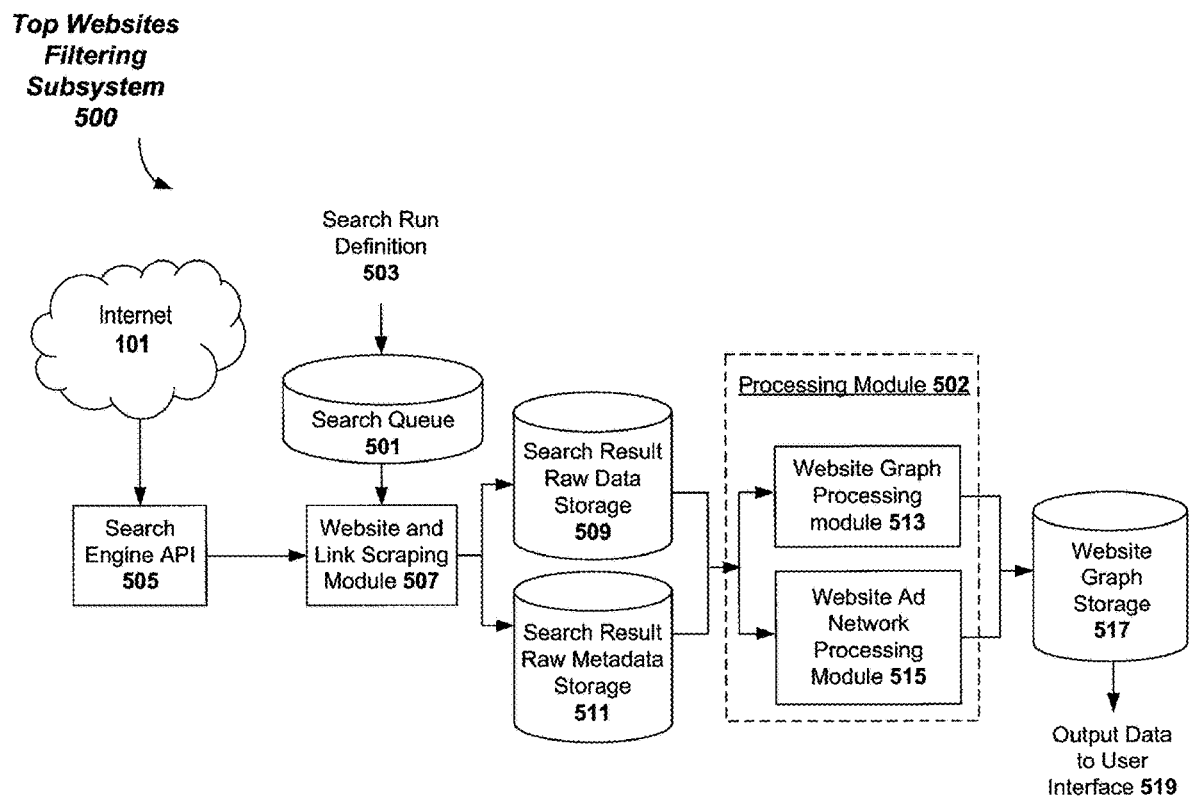
FIG. 12 illustrates a block diagram of the biosensors that remotely storing, monitoring and retrieving of transaction data, electronic payment data, location data, track movement data, logistics data, transportation data, physical, emotion and mental state data subsystem according to an exemplary embodiment hereof.
Figure 13:
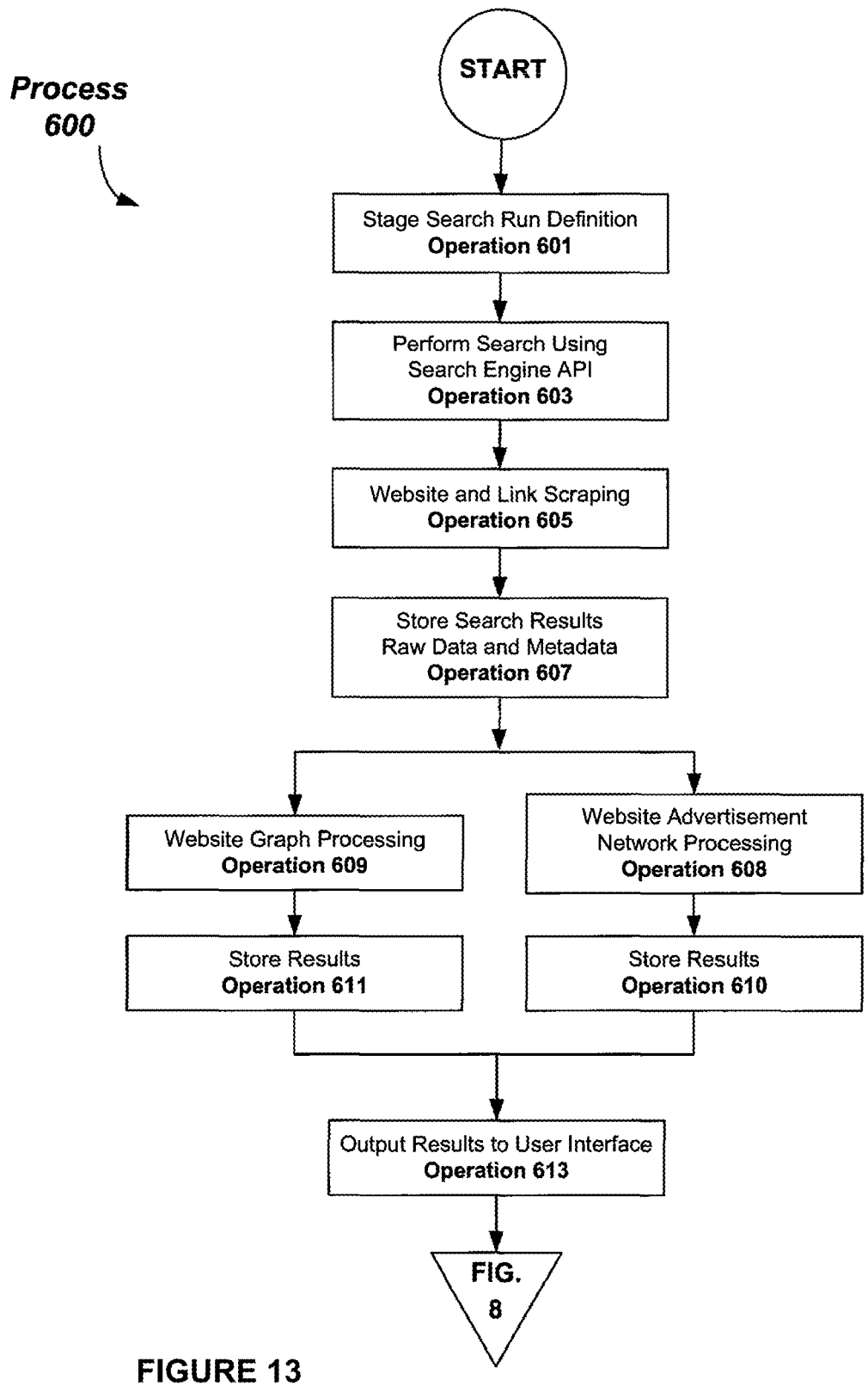
FIG. 13 illustrates performing integration of biometric data, healthcare, physical health conditions, medical conditions, track movement, logistics, transportation, track diseases for pets, livestock, dairy cows, cattle or other animals, diseases and conditions for disease control and prevention, monitoring antibiotics, pharmaceutical data and other data to develop a profile for one or more individuals according to an exemplary embodiment hereof.

FIG. 12 illustrates a block diagram of the top websites filtering subsystem according to an exemplary embodiment. The top websites filtering subsystem 500 is considered a part of the vertical layer 300 and determines websites that are the most relevant to a particular user. Subsystem 500 performs one or more searches using a search engine API (such as Google, Yahoo or Technorati), pulls out search results from the search engine, and assembles the search results data to model search behaviors of search engine users so that a list of the most relevant websites for a users' brands, products or other services or experiences can be compiled and provided to users of the wireless device platform. This can provide users with a list of websites having a high affinity for the users' industry or products/services so that targeted advertising campaigns can be launched, for example. Interestingly, this may not always be the websites with the highest traffic volume. This information is also fed into the user interface 705 of the presentation layer 700. The block diagram components of the top websites filtering subsystem 500 will be discussed in conjunction with process 600 of FIG. 13, which illustrates performing top websites filtering according to an exemplary embodiment.

Process 600 begins with staging one or more search run definitions 503 for processing in search queue 501 (operation 601). Search run definitions contain one or more brand or product names in combination with any number of other relevant keywords that a consumer might be searching for. One or more searches of the Internet 101 corresponding to the one or more search run definitions 503 staged in search queue 501 are then performed using one or more search engine APIs 505 (operation 603). The results of these searches are fed into website and link scraping module 507. Website and link scraping is then performed (operation 605) using the website and link scraping module 507. During this operation, the top websites filtering subsystem 500 actually goes into the websites found in the one or more searches and follows the website links within one or more of these websites. The websites found in the searches and the links within these websites is assembled for the purpose of attempting to model search engine users' behavior by determining which websites search engine users will likely visit when they run each of the one or more searches. In at least one embodiment, this information can provide users of the wireless device platform with a list of websites with a high affinity for the users' industry or products/services, of interest, of past, present or future customers, users, targets and/or target markets. This information may be useful in a variety of circumstances including allowing users to launch targeted advertising campaigns. For example, the top websites filtering subsystem 500 may run a search in Google for digital cameras and determine that a typical search engine user will only look at the first 3 web pages listed in the search results. The top websites filtering subsystem 500 will then follow the links in these 3 web pages to find more web pages and then follow the links in those web pages, and so on. The top websites filtering subsystem 500 will assemble this information and use it to build up a website and link network graph discussed below. The raw search result data resulting from website and link scraping module 507 is then stored in search result raw data storage 509 and the metadata is stored in search result raw metadata storage 511 (operation 607) to be provided to processing module 502.

Figure 14:
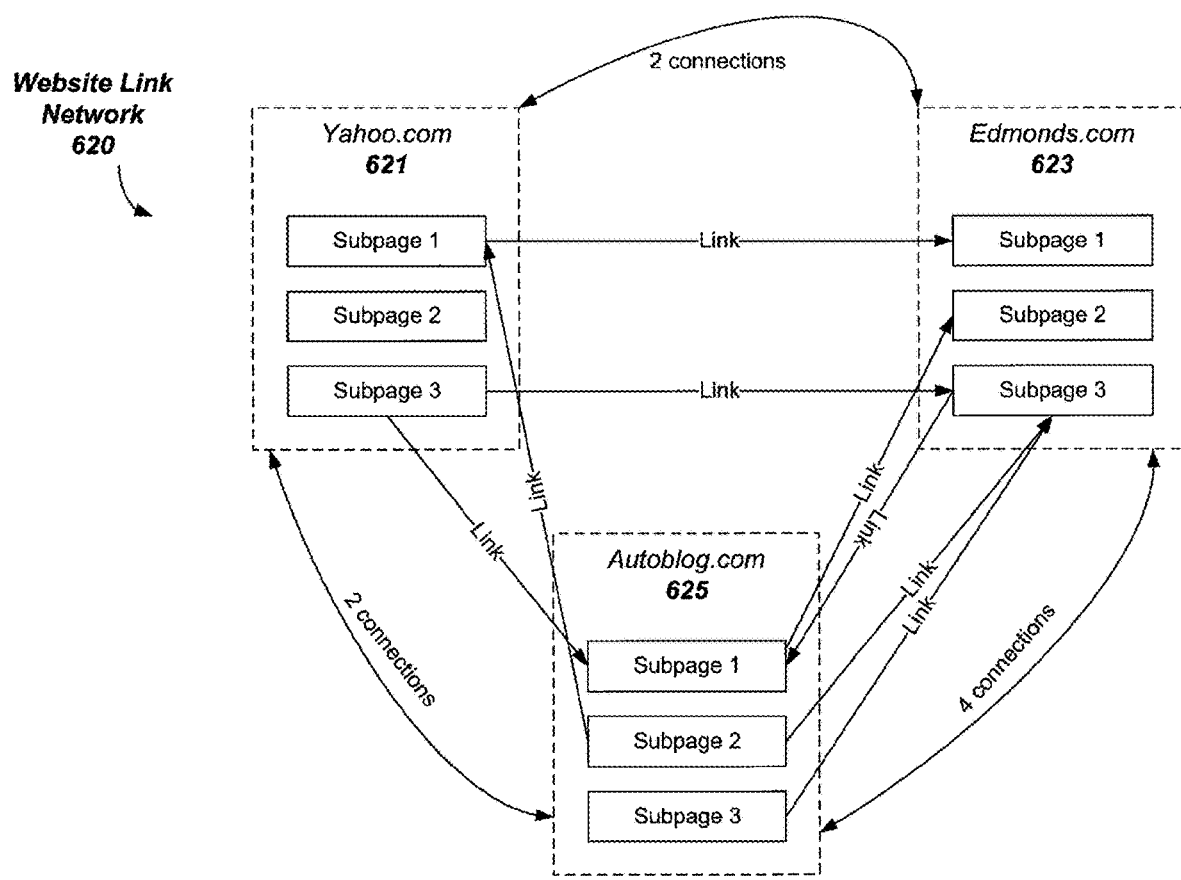
FIG. 14 illustrates an exemplary member network according to one embodiment hereof.
Figure 15:
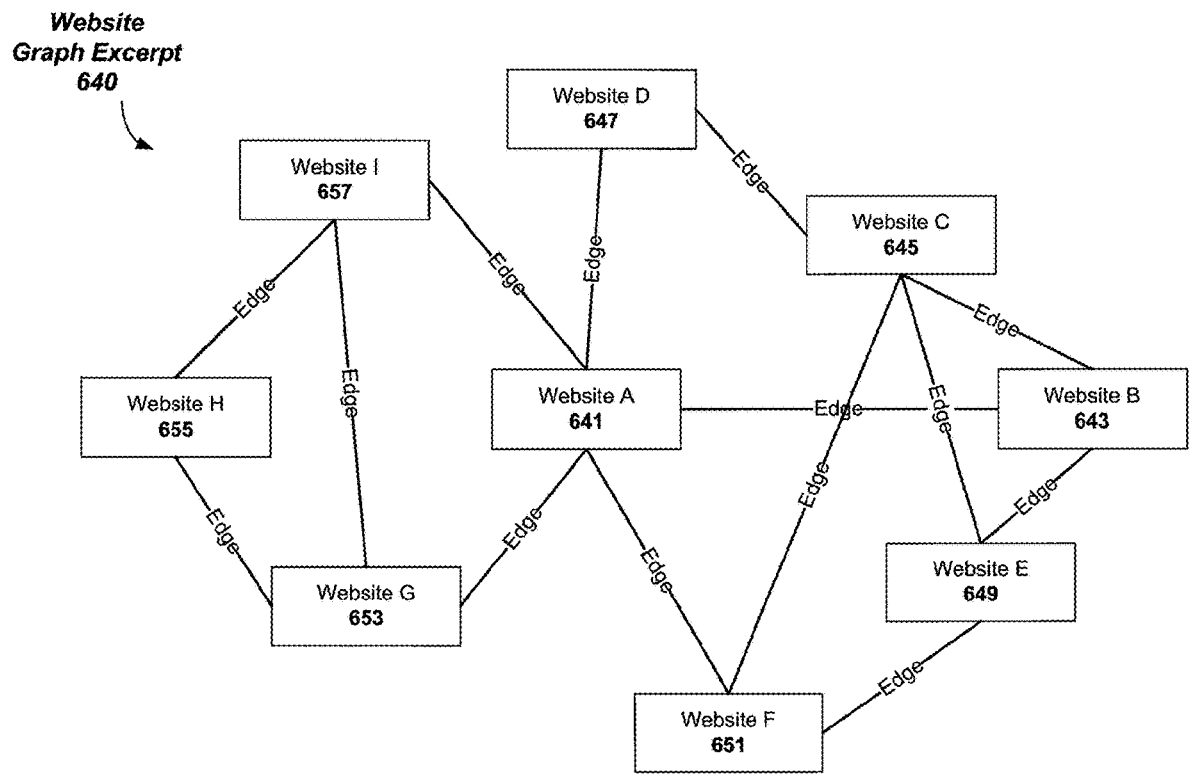
FIG. 15 illustrates an exemplary diagram of a data transfer and communication of user's data using nanotechnology and nanobiotechnology for the manipulation of matter on an atomic, molecular and supramolecular scale technologies and nanoparticles to perform functions such as targeted delivery, imaging or providing diagnostics and feedback/use/need for medicine for the detection, prevention and treatment of medical conditions, diseases and conditions for disease control and prevention according to an exemplary embodiment hereof.

Process 600 continues with performing website graph processing (operation 609). In at least one embodiment, the website graph processing includes using graph theory to analyze the website network to determine the radio frequency of occurrence of each website in the website network in connection with the relevant brand, product or service and to determine the relatedness of each website in the website network to that brand, product or service. Relationships between these websites and the relevant brand, product or service are analyzed to determine graph edges, which indicate the strength of these relationships. First, links between websites that contain content relevant to the brand, product or service are counted. The number of links between two websites provides an indication of how strongly the two websites are interconnected. FIG. 14 illustrates an exemplary website link network according to one embodiment. In the illustrated embodiment, website link network 620 includes three websites with links connecting to one another. In the example, there are two (2) connections between the websites Yahoo.com 621 and Edmunds.com 623 including a link from subpage 1 of Yahoo.com 621 to subpage 1 of Edmunds.com 623 and a link from subpage 3 of Yahoo.com 621 to subpage 3 of Edmunds.com 623. Likewise, there are four (4) connections between the websites Edmunds.com 623 and Autoblog.com 625 and two (2) connections between the websites Autoblog.com 625 and Yahoo.com 621 in the exemplary website link network 620. Once the number of links between each pair of websites is counted, a version of Brands' Betweenness Centrality algorithm is applied to the resulting graph. This algorithm calculates centrality values that indicate how strongly connected a given website is to other relevant websites, either directly or indirectly. This is depicted in FIG. 15 which illustrates an excerpt from a website graph according to an exemplary embodiment. In the illustrated embodiment, website graph excerpt 640 includes lines representing "edges" where each "edge" is a connection between each pair of websites in the graph. Website A 641 is connected to website B 643, website D 647, website F 651, website G 653 and website I 647 within one (1) edge. Website A 641 is further connected to website C 645, website E 649 and website H 655 within two (2) edges. Therefore, website A 641 is connected to each other website within one or two edges, so it will receive a high centrality value in comparison to the other websites. Internet users that find any of the other websites in the graph when looking for information are very likely to end up on website A 641; therefore, it is assumed that website A 641 is highly relevant to this graph. In this manner websites that are the most relevant to a particular user of the INVENTION platform are located.

Figure 16:
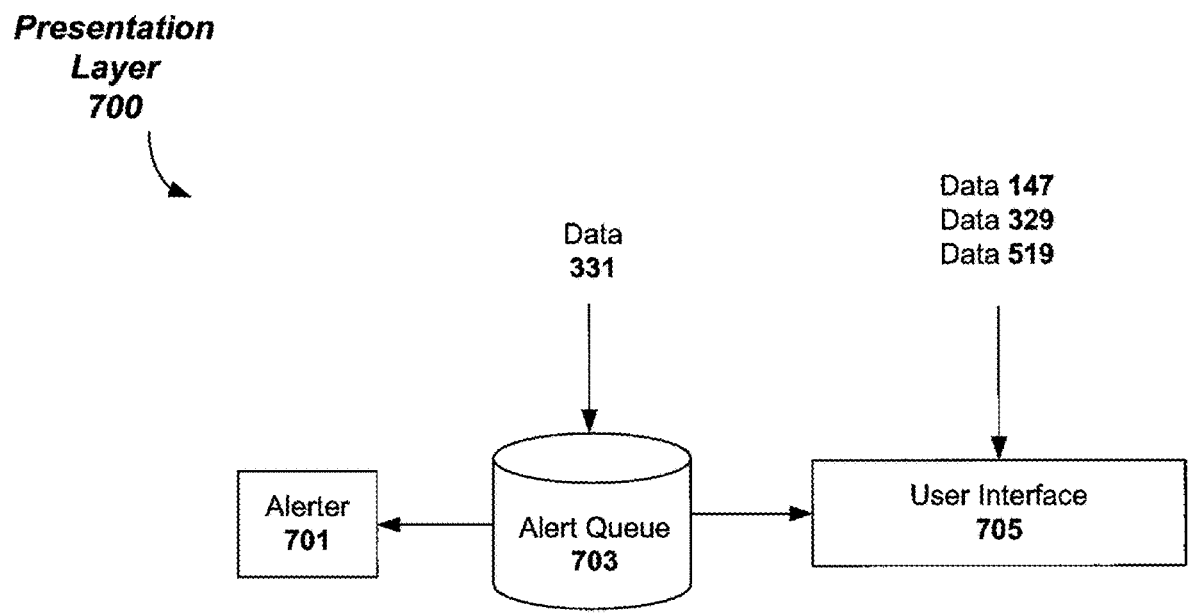
FIG. 16 illustrates an exemplary diagram of a data transfer and communication of user's data using EMFID sensors and integration of biometric data, transaction data, electronic payment data, location data, track movement data, logistics data, transportation data, and biosensors that remotely store, monitor and retrieve molecular data, physical, emotional and mental state data, emotions data, healthcare and pharmaceutical data and real-time tracking of nanobot interactions, location data and record movements of people, pets, livestock and objects and other data according to an exemplary embodiment hereof.

The resulting website network graph generated by the website graph processing module 513 is then stored in website graph storage 517 (operation 611) and the data 519 from the website graph storage 517 is output to the user interface 705 of the presentation layer 700 of FIG. 16 (operation 613). Process 600 continues at operation 608 where website advertisement network processing is performed using website ad network processing module 151. The website advertisement network processing, in at least certain embodiments, uses typical link patterns to identify advertisement networks that put advertisements on the analyzed websites. Since each advertisement network uses a particular type of software to provide advertisement banners, sponsored text links or other forms of online advertising, the resulting link patterns identify each advertisement network. Each website might carry advertisements from one or multiple networks, or no advertising at all. The website advertisement network processing is performed to provide users of the wireless device platform with information as to which advertisement networks are the most relevant for advertising their brands, products, or other services, of interest, of past, present or future customers, users, targets and/or target markets. The resulting website advertisement network information generated by the website ad network processing module 515 is also stored in website graph storage 517 (operation 610) and output to the user interface 705 of the presentation layer 700 in FIG. 16 (operation 613). This completes the top websites filtering process 600 according to an exemplary embodiment. In short, the top websites filtering subsystem 500 is used to locate websites users of the wireless device platform are most likely to reach when searching online for information about a particular brand, product or service.

Figure 17:
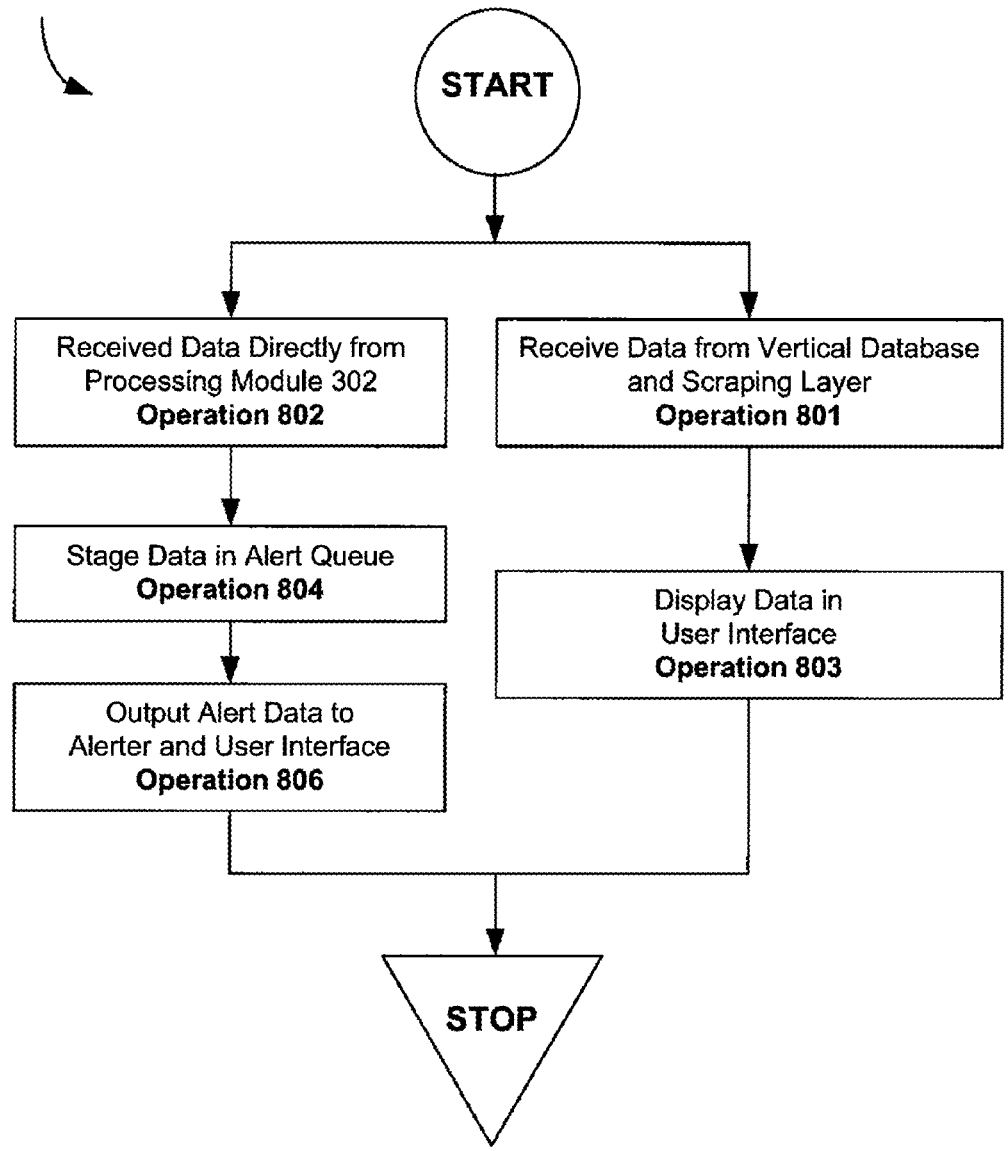
FIG. 17 illustrates presenting the analyzed and quantified radio frequency location and identification data transfer to a database that can be accessed by members of a network for products or other services or experiences or promotions via the Internet, communications, and social media content to users of the EMFID tracking tags analytics platform according to an exemplary embodiment hereof.

FIG. 16 illustrates a block diagram of the presentation layer according to an exemplary embodiment. The results of the vertical layer 300 processing and the top websites filtering subsystem 500 processing are fed into the presentation layer 700. In the illustrated embodiment, data 147 of FIG. 7, data 329 of FIG. 9, and data 519 of FIG. 12 are each fed into user interface 705. That is, the raw radio frequency location and identification data transfer to a database that can be accessed by members of a network for products or other services or experiences or promotions via the Internet, communications, and social media content and stored in raw content data storage 133, the social graph stored in data graph storage 141, the data stored in vertical data base 327, and the website graph and website ad network data stored in website graph storage 517 are fed into the user interface 705. Likewise, the data 331 including the results of the processing performed within processing module 302 of FIG. 7 is fed into the alert queue 703. The user interface 705 may be a GUI, some embodiments of which are discussed infra. The block diagram components of the presentation layer 700 will be discussed in conjunction with process 800 of FIG. 17, which illustrates presenting the analyzed and quantified radio frequency location and identification data transfer to a database that can be accessed by members of a network for products or other services or experiences or promotions via the Internet, communications, and social media content to users of the wireless device platform according to an exemplary embodiment.

Process 800 begins by receiving the data stored in the vertical database 327 of the vertical layer 300 in FIG. 7, receiving the data stored in the data graph storage 141, and receiving the data stored in the raw content data storage 133 of the collecting layer 100 in FIG. 7 (operation 801). This data is received and displayed in the user interface 705 (operation 803). Process 800 also includes receiving data directly from the results of the processing performed in processing module 302 of FIG. 9 (operation 802). This data is received and staged in the alert queue 703 (operation 804) to be output to the alerter 701 and the user interface 705. Among other things, the alerter 701 is used for alerting users of the wireless device platform of real-time or near real-time changes in user or consumer or brand sentiment regarding their brands, products, or other services, of interest, of past, present or future customers, users, targets and/or target markets. This completes process 800 according to an exemplary embodiment.

Some of the advantages of the EMFID tracking tags analytics platform are that embodiments provide: brand/product/service-level analytics including websites frequently talking about the relevant brand, product or service; social media authors frequently talking about the brand/product/service; overall volume of opinions about the brand, product or service; overall consumer or brand sentiment towards the brand, product or service; volume and consumer or brand sentiment of opinions about competing brands, products or other services or experiences; competing brands, products or other services or experiences most frequently mentioned in connection with the users' own brand, product or service; terms used most frequently in connection with a brand, product or service; and trends and early-warning alerts for all of the above. Embodiments also provide site-level analytics including site traffic (unique visitors and pages viewed), topic distribution of site, overall consumer or brand sentiment towards a given brand, products, services or experiences or technology, number of active or contributing users, relevance of the active users, relationships to other relevant sites, and trends in all of the above. Finally, embodiments provide user-level analytics (users referred to here are participants in social media sites) including: sites on which users contributed content; known identities of users, users' registrations in social networks; influence of users; users' known ownership and/or use of a given products, services or experiences or technology; users' or consumers' sentiment toward a given brand, products, services or experiences or technology; users' known demographic and geographical attributes; and trends in all of the above.

In at least certain embodiments, a GUI is utilized to present the quantified and analyzed radio frequency location and identification data transfer to a database that can be accessed by members of a network for products or other services or experiences or promotions via the Internet, communications, and social media content in a manner relevant to the user. The GUI may be fully customizable giving users the ability to select which charts and graphs should appear on the login page of the interface. The GUI provides an intuitive display to visualize brand, product or service consumer or brand sentiment over time. This display is a quantitative measure of consumer opinion or sentiment for a brand, products, services or experiences, or its competitors and is derived from an automated analysis of consumer or brand sentiment ratings on each individual post to online social media about a brand, products, services or experiences and/or those of their competitors. The GUI includes various knobs or switches to manipulate the above information in a variety of ways. Among many other things, inside the GUI users can filter information by product/service or competitor, groups of websites, data ranges, or drill down to the lowest level of granularity of the information to see the actual text of online social media posts as it appears on the originating source website. The GUI provides a visualization that allows users to give context to each social media post and gain familiarity with the posting website. The GUI is designed to be used by non-expert users without help from consultants. The GUI not only provides standard spreadsheet-style visualization such as bar and pie charts, but also highly innovative approaches including: radar screen; heat maps; geographical visualization; 3D clustering, tag clouds, and timelines. Content may be collected from as far back as sources make available. For example, discussion boards can have posts from many years ago. The start date on the GUI is configurable and is designed for ease-of-use allowing for a visualization of the underlying data calculations and analysis instead of simply raw data.

Figure 18:
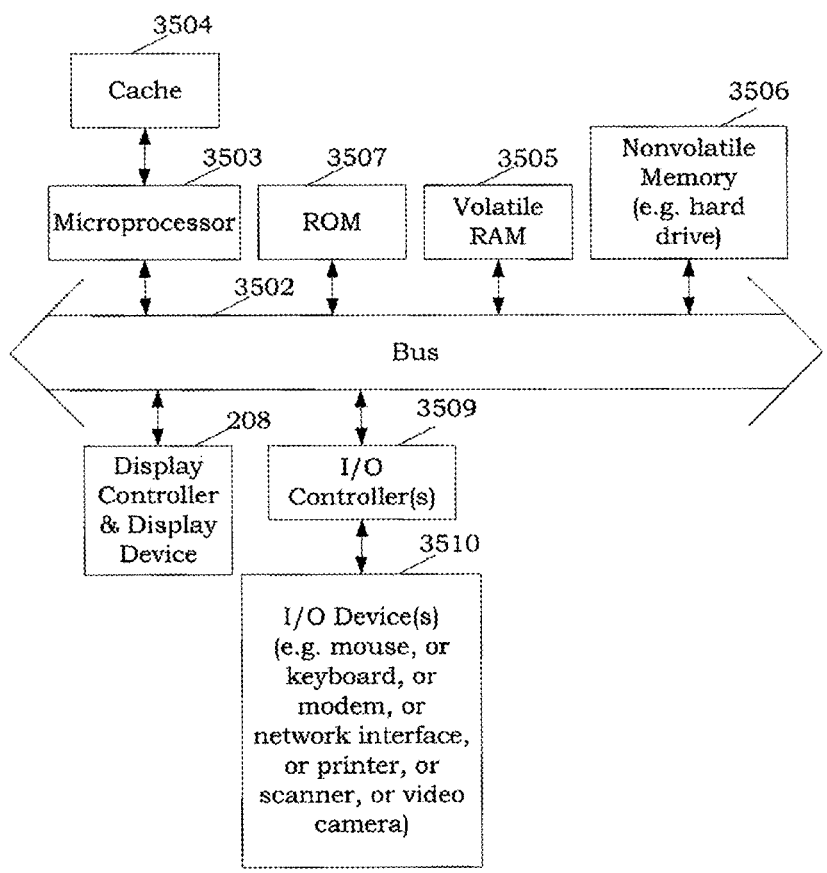
FIG. 18 illustrates an exemplary data processing system upon which the methods and apparatuses hereof may be implemented.

FIG. 18 illustrates an exemplary data processing system upon which the methods and apparatuses hereof may be implemented. Note that while FIG. 18 illustrates various components of a data processing system, it is not intended to represent any particular architecture or manner of interconnecting the components as such details are not germane hereto. It will also be appreciated that network computers and other data processing systems, which have fewer components or perhaps more components, may also be used. The data processing system of FIG. 18 may, for example, be a workstation, or a personal computer (PC) running a Windows operating system, or an Apple Macintosh computer.

As shown in FIG. 18, the data processing system 3501 includes a system bus 3502, which is coupled to a microprocessor 3503, a ROM 3507, a volatile RAM 3505, and a non-volatile memory 3506. The microprocessor 3503, which may be a processor designed to execute any instruction set, is coupled to cache memory 3504 as shown in the example of FIG. 18. The system bus 3502 interconnects these various components together and also interconnects components 3503, 3507, 3505, and 3506 to a display controller and display device 3508, and to peripheral devices such as input/output (I/O) devices 3510, such as keyboards, modems, network interfaces, printers, scanners, video cameras and other devices (e.g., wearable banking wristbands, kitchen appliances, garments, fashion apparel, household items, internet things, remote controls, TVs, cabinets, walls, flooring, automobiles, radio clocks, electronics, wallets, digital wallets, transmitters, airport scanners, readers, printers, tags, smart labels, UHF passive RFID transceiver chips, inlays & labels, fixed & mobile readers, smartphones, mobile devices, blue tooth devices or other wireless devices, keys, currency, passport cards, enhanced drivers' license (EDL), barcodes, drugs, cigarettes, EMFID labels of pharmaceutical products, electronic product code (EPC), EMFID inventory tracking, EMFID logistic applications, animal identification, Garment EMFID Inventory Management System (GIMS), EMFID chip vaccinations, clothing, merchandise, pharma/healthcare, products or other services or experiences, mobile coupons, electronic skin tattoos, electronic hologram EMFID tags, payment cards, student ID cards, corporate identification cards or integration of biometric ID cards, wireless biosensors, laptops, computers, PCs, and other devices, etc.) which are well known in the art. Typically, the I/O devices 3510 are coupled to the system bus 3502 through input/output controllers 3509. The volatile RAM 3505 is typically implemented as dynamic RAM (DRAM), which requires power continually in order to refresh or maintain the data in the memory. The non-volatile memory 3506 is typically a magnetic hard drive or a magnetic optical drive or an optical drive or a DVD RAM or other type of memory systems, which maintain data even after power is removed from the system. Typically, the non-volatile memory 3506 will also be a random access memory although this is not required. While FIG. 18 shows that the non-volatile memory 3506 is a local device coupled directly to the rest of the components in the data processing system, it will be appreciated that the present developments may utilize a non-volatile memory which is remote from the system, such as a network storage device which is coupled to the data processing system through a network interface such as a modem or Ethernet interface (not shown). The system bus 3502 may include one or more buses connected to each other through various bridges, controllers and/or adapters (not shown) as is well known in the art. In one embodiment the I/O controller 3509 includes a USB (Universal Serial Bus) adapter for controlling USB peripherals, and/or an IEEE-1394 bus adapter for controlling IEEE-1394 peripherals.

It will be apparent from this description that aspects hereof may be embodied, at least in part, in software, hardware, firmware, or in combination thereof. That is, the techniques may be carried out in a computer system or other data processing system in response to its processor, such as a microprocessor, executing sequences of instructions contained in a memory, such as ROM 3507, volatile RAM 3505, non-volatile memory 3506, cache 3504, or a remote storage device (not shown). In various embodiments, hardwired circuitry may be used in combination with software instructions to implement the present developments. Thus, the techniques are not limited to any specific combination of hardware circuitry and software or to any particular source for the instructions executed by the data processing system 3500. In addition, throughout this description, various functions and operations are described as being performed by or caused by software code to simplify description. However, those skilled in the art will recognize that what is meant by such expressions is that the functions result from execution of code by a processor, such as the microprocessor 3503.

The developments hereof also relate to apparatuses for performing the operations herein. These apparatuses may be specially constructed for the required purposes, or may comprise a general-purpose computer selectively activated or reconfigured by a computer program stored in the computer. Such a computer program may be stored or transmitted in a computer-readable medium. A computer-readable medium can be used to store software and data which when executed by a data processing system, such as data processing system 3500, causes the system to perform various methods hereof. This executable software and data may be stored in various places including for example ROM 3507, volatile RAM 3505, non-volatile memory 3506, and/or cache 3504 as shown in FIG. 18. Portions of this software and/or data may be stored in any one of these storage devices. A computer-readable medium may include any mechanism that provides (i.e., stores and/or transmits) information in a form accessible by a machine (e.g., a computer, network device, personal digital assistant, manufacturing tool, any device with a set of one or more processors, etc.) For example, a machine readable medium includes recordable/non-recordable media such as, but not limited to, a computer-readable storage medium (e.g., any type of disk including floppy disks, optical disks, CD-ROMs, and magnetic-optical disks, read-only memories (ROMs), random access memories (RAMs), EPROMs, EEPROMs, flash memory, magnetic or optical cards, or any type of media suitable for storing electronic instructions), or a computer-readable transmission medium such as, but not limited to, any type of electrical, optical, acoustical or other form of propagated signals (e.g., carrier waves, infrared signals, digital signals, etc.)

Additionally, it will be understood that the various embodiments described herein may be implemented with data processing systems, which have more or fewer components than system 3500. For example, such data processing systems may be a cellular telephone or a personal digital assistant (PDA) or an entertainment system or a media player or a consumer electronic device, and et cetera, each of which can be used to implement one or more of the embodiments hereof. The algorithms and displays presented herein are not inherently related to any particular computer system or other apparatus. Various general-purpose systems may be used with programs in accordance with the teachings herein, or it may prove convenient to construct more specialized apparatuses to perform the method operations. The structure for a variety of these systems appears from the description above. In addition, the developments are not described with reference to any particular programming language. It will be appreciated that a variety of programming languages may be used to implement the teachings hereof as described herein.

Throughout the specification, references to "one embodiment," "an embodiment," "an example embodiment," and et cetera, indicate that the embodiment described may include a particular feature, structure, or characteristic, but every embodiment may not necessarily include the particular feature, structure, or characteristic. Moreover, such phrases are not necessarily referring to the same embodiment. When a particular feature, structure, or characteristic is described in connection with an embodiment, it is submitted that it is within the knowledge of one skilled in the art to bring about such a feature, structure, or characteristic in connection with other embodiments whether or not explicitly described. Various changes may be made in the structure and embodiments shown herein without departing from the principles hereof. Further, features of the embodiments shown in various figures may be employed in combination with embodiments shown in other figures.

In the description as set forth above and claims, the terms "coupled" and "connected," along with their derivatives, may be used. It should be understood that these terms are not intended to be synonymous with each other. Rather, in particular embodiments, "connected" is used to indicate that two or more elements are in direct physical or electrical contact with each other. "Coupled" may mean that two or more elements are in direct physical or electrical contact. However, "coupled" may also mean that two or more elements are not in direct contact with each other, but yet still co-operate or interact with each other.

Some portions of the detailed description as set forth above are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the discussion as set forth above, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Embodiments may include various operations as set forth above or fewer operations or more operations or operations in an order, which is varying from the order described herein. The operations may be embodied in machine-executable instructions, which cause a general-purpose or special-purpose processor to perform certain operations. Alternatively, these operations may be performed by specific hardware components that contain hardwired logic for performing the operations, or by any combination of programmed computer components and custom hardware components.

Throughout the foregoing description, for the purposes of explanation, numerous specific details were set forth in order to provide a thorough understanding of the invention. It will be apparent, however, to one skilled in the art that the invention may be practiced without some of these specific details. Accordingly, the scope and spirit of the invention should be judged in terms of the claims, which follow as well as the legal equivalents thereof.

Figure 19:
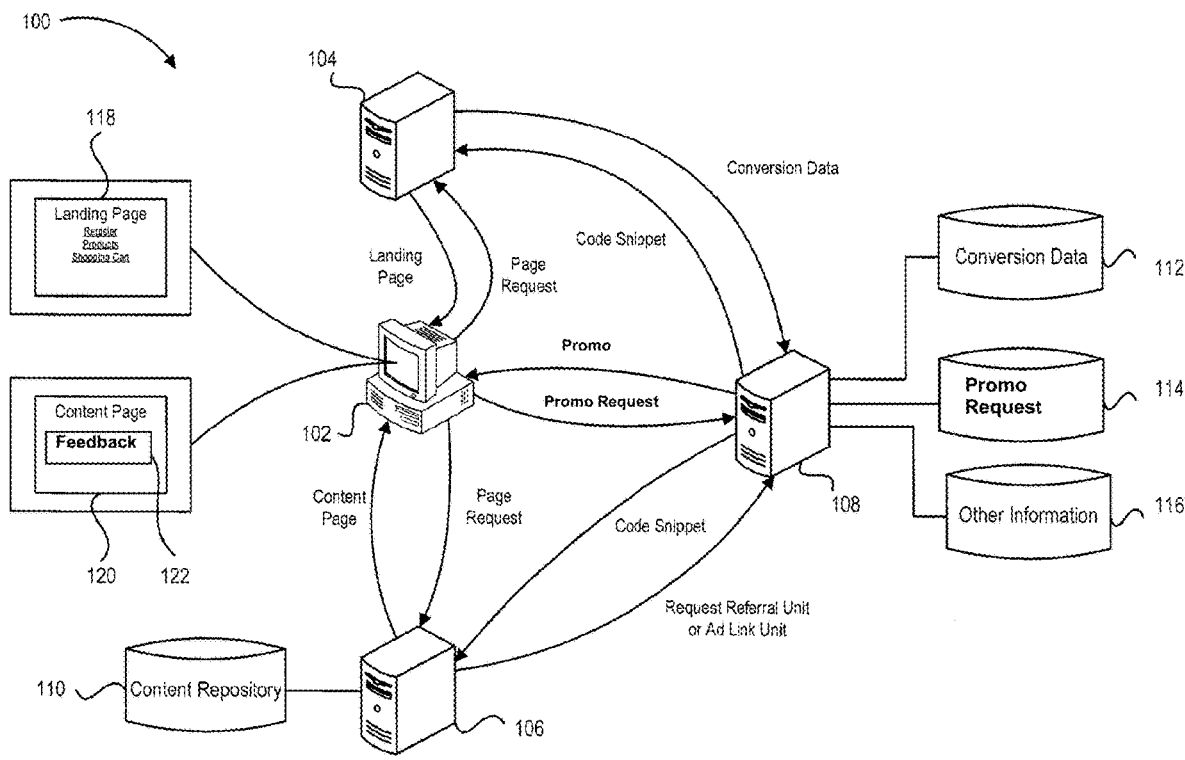
FIG. 19 is a block diagram of an example online system hereof.

FIG. 19 is a block diagram of an example online advertising system 100. In some implementations, one or more advertisers 104 can directly, or indirectly, enter, maintain, and track advertisement, ("ad") information in an ad management system 108. The ads can be stored in a repository 114 coupled to the system 108, (e.g., a MySQL® database). The ads may be in the form of graphical ads, such as banner ads or graphic color ads, sponsored video ads, digital promotions or offers, online classified ads, yellow page ads, white page ads, text message ads, interactive advertising, text only ads, image ads, audio ads, social video sharing EMFID tag communications, video ad EMFID tag communications, audio-video & photography EMFID tag communications, washable EMFID tags, near field communication (EMFID NFC), EMFID NFC tag communications, EMFID NFC tags, EMFID NFC boarding pass EMFID tag communications, mobile boarding pass EMFID tag communications, payment and tracking passenger EMFID tag communications, aggregator EMFID tag communications, viral EMFID tag communications, any language or translated into any language EMFID tag communications, sports ad EMFID tag communications, brand EMFID tag communications, global brands, dairy farmers, milk production and dairy products or milk products, animal farming companies, cattle farmers, industrial livestock production companies, pharmaceutical chain EMFID tag communications, product EMFID tag communications, goods EMFID tag communications, gambling EMFID tag communications, auction EMFID tag communications, real estate EMFID tag communications, shopping EMFID tag communications, banking EMFID tag communications, sports EMFID tag communications, travel & hospitality EMFID tag communications, social gaming EMFID tag communications, autos & vehicles EMFID tag communications, pets & animals EMFID tag communications, online communication EMFID tag communications, education EMFID tag communications, services EMFID tag communications, social tracking EMFID tag communications, social shopping EMFID tag communications, banking EMFID tag communications, sharing on a social networking system digital content EMFID tag communications, mobile social video sharing EMFID tag communications, video ad EMFID tag communications, audio-video & photography EMFID tag communications, washable EMFID tags, near field communication (EMFID NFC), EMFID NFC tag communications, EMFID NFC tags, EMFID NFC boarding pass EMFID tag communications, mobile boarding pass EMFID tag communications, payment and tracking passenger EMFID tag communications, aggregator EMFID tag communications, viral EMFID tag communications, any language or translated into any language EMFID tag communications, mobile ads, mobile ad network, mobile advertising for mobile publishers and advertisers and mobile commerce, mobile location-based advertising and promotions, ads combining one of more of any of such components, etc. The ads may also include embedded in any physical objects, including without limitation, EMFID edible drugs, Medical EMFID card with prescription, EMFID labels of pharmaceutical products, electronic product code (EPC), EMFID inventory tracking, EMFID logistic applications, animal identification, Garment EMFID Inventory Management System (GIMS), EMFID chip vaccinations, EMFID packaging, EMFID passports, EMFID credit cards, EMFID debit cards, other forms of EMFID payment systems, EMFID travel cards, edible EMFID tags, EMFID navigation systems, EMFID vehicle tags, EMFID retail, EMFID clothing, EMFID pharma/healthcare, EMFID merchandise, EMFID smart dust, EMFID mobile devices, EMFID wireless devices, EMFID international mobile equipment identity (IMEI), other EMFID wireless or EMFID handheld devices, computers, PCs, currency, identification cards, products or other services or experiences and/or implanted subdermal information, such as embedded in any physical objects, including without limitation, EMFID edible drugs, Medical EMFID card with prescription, EMFID labels of pharmaceutical products, electronic product code (EPC), EMFID inventory tracking, EMFID logistic applications, animal identification, Garment EMFID Inventory Management System (GIMS), EMFID chip vaccinations, EMFID packaging, EMFID passports, EMFID credit cards, EMFID debit cards, other forms of EMFID payment systems, EMFID travel cards, edible EMFID tags, EMFID navigation systems, EMFID vehicle tags, EMFID retail, EMFID clothing, EMFID pharma/healthcare, EMFID merchandise, EMFID smart dust, EMFID mobile devices, EMFID wireless devices, EMFID international mobile equipment identity (IMEI), other EMFID wireless or EMFID handheld devices, computers, PCs, currency, identification cards, products or other services or experiences and/or implanted subdermal media, links, meta-information, and/or machine executable instructions. One or more publishers 106 may submit requests for ads or company/brand/social/global EMFID tag interactions promotional data set to the system 108. The system 108 responds by sending ads, company/brand/social/global EMFID tag interactions promotional data set, or information that can allow for the retrieval from a ads or company/brand/social/global EMFID tag interactions promotional data set to the requesting publisher 106 for placement/serving one or more of the publisher's web properties, (e.g., websites and other network-distributed content marketing EMFID tag communications). The advertising search EMFID tag communications for location-based promotions, location-based offers, location-based information, social media content, promotions or offers in connection with an online EMFID tag or mobile EMFID tag, position-based services, location-based advertising, mobile location-based advertising and promotions or offers and marketing EMFID tag communications, online coupons and/or location-based deals and offers and location-based services in real-time via a mobile device or tablet device or mobile internet devices or holographic devices or holographic phone or wireless data transfer device, (such as a mobile phone networks or Wi-Fi networks) or computer, online coupons, position-based services, ad links, location-based promotions, location-based offers, location-based information, social media content, promotions or offers in connection with an online EMFID tag or mobile EMFID tag, discount ad EMFID tag communications, merchant ad EMFID tag communications, email coupon EMFID tag communications, location-based advertising, mobile location-based advertising and promotions or offers and marketing EMFID tag communications, in real time, or company/brand/social/global EMFID tag interactions promotional data set can be placed with or embedded in any physical objects, including without limitation, EMFID edible drugs, Medical EMFID card with prescription, EMFID labels of pharmaceutical products, electronic product code (EPC), EMFID inventory tracking, EMFID logistic applications, animal identification, Garment EMFID Inventory Management System (GIMS), EMFID chip vaccinations, EMFID packaging, EMFID passports, EMFID credit cards, EMFID debit cards, other forms of EMFID payment systems, EMFID travel cards, edible EMFID tags, EMFID navigation systems, EMFID vehicle tags, EMFID retail, EMFID clothing, EMFID pharma/healthcare, EMFID merchandise, EMFID smart dust, EMFID mobile devices, EMFID wireless devices, EMFID international mobile equipment identity (IMEI), other EMFID wireless or EMFID handheld devices, computers, PCs, currency, identification cards, products or other services or experiences and/or implanted subdermal in the publisher's content, (e.g., videos, articles, search results), which can be stored in a repository 110 at the publisher 106, and/or placed with content received from other sources, (e.g., other publishers, advertisers).

In some implementations, publisher's properties available in this system may also include both Internet-distributed and broadcast distributed content such as, but not limited to, television spots, radio spots, print advertising, billboard advertising, (electronic or printed), on-vehicle advertising, and the like.

Other entities, such as users or members 102 and advertisers 104, can provide usage information to the system 108, such as, for example, whether or not a conversion or click-through related to an ad has occurred. In some implementations, conversion data can be stored in a repository 112, where it can be used by the system 108 to improve ad-targeting performance. The usage information provided to the system 108 can include measured or observed human behavior related to ads that have been served. In some implementations, the system 108 performs payment systems, EMFID NFC transactions, EPC tag communications, contactless RFID communications, such as crediting the publishers 106 and charging the advertisers 104 based on the usage information.

A computer network, such as a local area network, (LAN), wide area network, (WAN), the Internet, wireless network or a combination thereof, can connect the location-based services, advertisers 104, the system 108, the publishers 106, and the users or members 102.

One example of a publisher 106 is a general content server that receives requests for content, (e.g., articles, electronic mail messages, discussion threads, music, video, graphics, network games, search results, web page listings, information feeds, dynamic web page content, etc.)3 and retrieves the requested content in response to the request. The content server may submit a request, (either directly or indirectly) for advertising search EMFID tag communications for location-based promotions, location-based offers, location-based information, social media content, promotions or offers in connection with an online EMFID tag or mobile EMFID tag or advertisements or company/brand/social/global EMFID tag interactions promotional data set to an ad server in the system 108. The location-based services or ad request may include a number of ads desired. The company/brand/social/global EMFID tag interactions promotional data set request may include a number of company/brand/social/global EMFID tag interactions promotional data set desired and the number of company/brand/social/global EMFID tag interactions per company/brand/social/global EMFID tag interactions promotional data set. The advertising search EMFID tag communications for location-based promotions or offers or advertisements or company/brand/social/global EMFID tag interactions promotional data set request may also include content request information. This information can include the content itself, (e.g., page or other content document), a category or keyword corresponding to the content or the content request, (e.g., arts, business, computers, arts-movies, arts-music, etc.), part or all of the content request, content age, content type, (e.g., text, graphics, video, audio, mixed media, etc.), geo-location or geo-tagging information, demographic information related to the content, keyword, web property, etc., and the like.

In some implementations, the content server, (or a browser rendering content provided by the content server) can combine the requested content with one or more of the advertising search EMFID tag communications for location-based promotions, location-based offers, location-based information, social media content, promotions or offers in connection with an online EMFID tag or mobile EMFID tag or advertisements, or company/brand/social/global EMFID tag interactions promotional data set provided by the system 108. The combination can happen prior to delivery of the content to the user or contemporaneously where the advertising server can serve the ads or company/brand/social/global EMFID tag interactions promotional data set directly to an end user. The combined content and location-based promotions or offers promotions or offers or advertisements or company/brand/social/global EMFID tag interactions promotional data set can be delivered to the user 102 that requested the content for presentation in a viewer, (e.g., a browser or other content display system). The content server can transmit information about the location-based promotions, location-based offers, location-based information, social media content, promotions or offers in connection with an online EMFID tag or mobile EMFID tag or advertisements, or company/brand/social/global EMFID tag interactions promotional data set back to the ad server, including information describing how, when, and/or where the location-based promotions, location-based offers, location-based information, social media content, promotions or offers in connection with an online EMFID tag or mobile EMFID tag or advertisements or company/brand/social/global EMFID tag interactions promotional data set are to be rendered, (e.g., in HTML or JavaScript™) The content page 120 can be rendered in the user's viewer with one or more ads 122. When the user 102 ad click EMFID tag communications on a displayed ad 122 of an advertiser, the user 102 can be redirected to a landing page 118 of the advertiser's web site.

Figure 20:
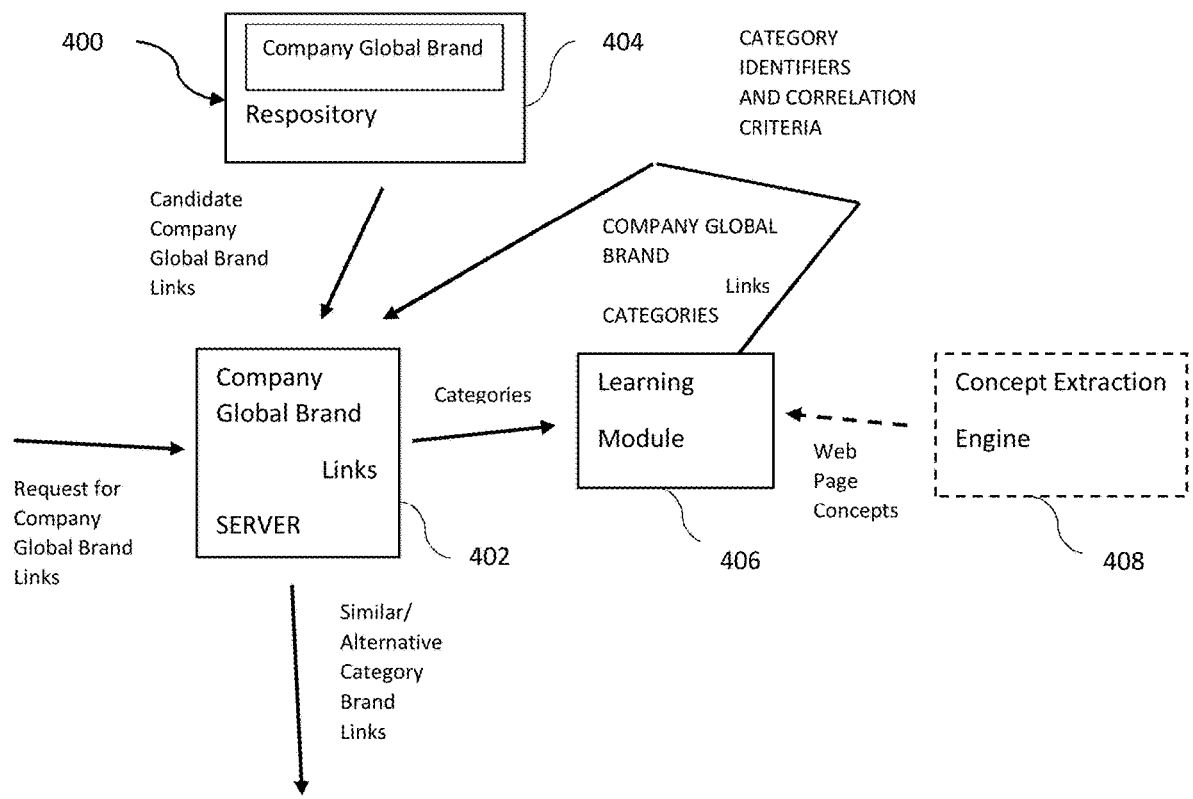
FIG. 20 is a block diagram of an example implementation of an advertising management system hereof that provides related company/brand/social/global EMFID tag interactions promotional data set with correlated broad and alternative categories.

FIG. 20 is a block diagram of an example implementation 400 of an advertising management system 108 of FIG. 20 that provides related company/brand/social/global EMFID tag interactions promotional data set with correlated broad and alternative categories. The advertising management system 108 includes a company/brand/social/global EMFID tag interactions server 402, a company/brand/social/global EMFID tag interactions repository 404, and a learning module 406. In some implementations, the system 108 also includes a concept extraction engine 408. In some implementations, the ad server in system 108 also serves related company/brand/social/global EMFID tag interactions.

The company/brand/social/global EMFID tag interactions server 402 receives requests for related company/brand/social/global EMFID tag interactions promotional data set. In some implementations, the company/brand/social/global EMFID tag interactions server 402 receives related company/brand/social/global EMFID tag interactions promotional data set requests from one or more content marketing EMFID tag communications servers. A company/brand/social/global EMFID tag interactions promotional data set request can accompany an ad request, where both the location-based advertisements and location-based services, position-based services, ad links, location-based promotions, location-based offers, location-based information, social media content, promotions or offers in connection with an online EMFID tag or mobile EMFID tag, discount ad EMFID tag communications, merchant ad EMFID tag communications, email coupon EMFID tag communications, online coupons, position-based services, ad links, location-based promotions, location-based offers, location-based information, social media content, promotions or offers in connection with an online EMFID tag or mobile EMFID tag, discount ad EMFID tag communications, merchant ad EMFID tag communications, email coupon EMFID tag communications, location-based advertising, mobile location-based advertising and promotions or offers and marketing EMFID tag communications, in real time, geo-targeted or geo-tagged advertisements and/or location-based promotions, location-based offers, location-based information, social media content, promotions or offers in connection with an online EMFID tag or mobile EMFID tag and capturing, processing, analyzing and filtering EMFID tag communications based upon people, places and things, content, audience, geographical area, delivery modes, data sets and ad markers and distribution of mobile or Wi-Fi networks) or computer, online coupons, position-based services, ad links, location-based promotions, location-based offers, location-based information, social media content, promotions or offers in connection with an online EMFID tag or mobile EMFID tag, discount ad EMFID tag communications, merchant ad EMFID tag communications, email coupon EMFID tag communications, location-based advertising, mobile location-based advertising and promotions or offers and marketing EMFID tag communications, in real-time and company/brand/social/global EMFID tag interactions promotional data set are to be displayed with the same content marketing EMFID tag communications. In some implementations, a content marketing EMFID tag communications server sends a combined request for both ads and company/brand/social/global EMFID tag interactions promotional data set. The related company/brand/social/global EMFID tag interactions promotional data set request may include a number, (e.g., one, two, or three) of related company/brand/social/global EMFID tag interactions promotional data set desired and the number, (e.g., four or five) of related company/brand/social/global EMFID tag interactions promotional data set categories for each related company/brand/social/global EMFID tag interactions promotional data set. The related company/brand/social/global EMFID tag interactions promotional data set request may also include content marketing EMFID tag communications request information. For example, the information can include the content marketing EMFID tag communications itself or one or more categories or keyword corresponding to the content marketing EMFID tag communications or the content marketing EMFID tag communications request.

The company/brand/social/global EMFID tag interactions server 402 receives candidate related company/brand/social/global EMFID tag interactions from a company/brand/social/global EMFID tag interactions repository 404. In some implementations, the candidate related company/brand/social/global EMFID tag interactions are determined based on keyword corresponding to the requested content marketing EMFID tag communications with which the related company/brand/social/global EMFID tag interactions promotional data set is to be displayed. Other matching techniques can be used.

The company/brand/social/global EMFID tag interactions server 402 identifies categories for the candidate related company/brand/social/global EMFID tag interactions and forwards the categories to a learning module 406. In some implementations, the categories are the same as the candidate related company/brand/social/global EMFID tag interactions. In some implementations, the candidate related company/brand/social/global EMFID tag interactions are a subset of the categories that can be selected for company/brand/social/global EMFID tag interactions promotional data set displayed with requested content marketing EMFID tag communications.

In some implementations, the related company/brand/social/global EMFID tag interactions promotional data set request can include an identifier, (e.g., the Uniform Resource Locator, (URL) of the webpage with the requested content marketing EMFID tag communications with which the related company/brand/social/global EMFID tag interactions promotional data set is to be displayed. Using the identifier, the web page can be crawled to determine one or more concepts evoked by the content marketing EMFID tag communications of the web page. An optional concept extraction engine 408 can extract concepts from the web page content marketing EMFID tag communications. The web page concepts can be forwarded to the learning module 406. Some examples of concept extraction engines are described in U.S. Pat. No. 7,231,393 and U.S. 2004/0068697, each of which, is incorporated by reference herein in its entirety.

The learning module 406 receives related company/brand/social/global EMFID tag interactions categories from the company/brand/social/global EMFID tag interactions server 402. The learning module 406 generates or retrieves one or more category identifiers associated with each related company/brand/social/global EMFID tag interactions category. As described above, each related company/brand/social/global EMFID tag interactions category can be classified under one or more categories. In some implementations, the category identifiers are predetermined. For example, the category identifiers for the related company/brand/social/global EMFID tag interactions categories can be determined before a related company/brand/social/global EMFID tag interactions promotional data set request is served. In some implementations, the category identifiers are pre-computed for the keyword for ads in the company/brand/social/global EMFID tag interactions repository 404.

In some implementations, the learning module 406 also receives web page concepts from the concept extraction engine 408. Web page concepts can also be classified under one or more categories. Category identifiers for the web page concepts can be determined when a related company/brand/social/global EMFID tag interactions promotional data set request is received.

The learning module 406 computes one or more correlation criteria for each related company/brand/social/global EMFID tag interactions category. A correlation measure provides a measure of how "close" or "distant" in correlation two category identifiers are, where the pair of category identifiers corresponds to two related company/brand/social/global EMFID tag interactions categories. If category identifiers are determined for the web page concepts, correlation criteria can also be computed between a category identifier associated with a related company/brand/social/global EMFID tag interactions category and a category identifier associated with one of the web page concepts.

In some implementations, the correlation measure can be computed using statistics accumulated over a large set of documents, (e.g., web pages). For example, the number of instances of a document evoking two category concepts can be determined. The number of instances can be used as a heuristic to measure the correlation between the two categories. That is, the larger the number of instances, the more likely the two categories are similar. Techniques for associating documents and co-occurring category concepts are described in U.S. Patent Publication No. 2006/0242013 A1, filed Oct. 26, 2006, for "Suggesting Targeting Information for Ads, Such as Websites and/or Categories of Websites for Example". The correlation measure is further discussed below.

The company/brand/social/global EMFID tag interactions server 402 receives from the learning module 406 one or more correlation criteria for each related company/brand/social/global EMFID tag interactions category. In some implementations, the company/brand/social/global EMFID tag interactions server 402 also receives the category identifiers from the learning module 406. The company/brand/social/global EMFID tag interactions server 402 generates the same, similar, broad or alternative, company/brand/social/global EMFID tag interactions categories based on the correlation criteria of the candidate company/brand/social/global EMFID tag interactions categories. The same, similar, broad or alternative, company/brand/social/global EMFID tag interactions categories are organized into one or more related company/brand/social/global EMFID tag interactions promotional data set which can be provided by the system 108 to the content marketing EMFID tag communications server to be combined with the requested content marketing EMFID tag communications.

In some implementations, the company/brand/social/global EMFID tag interactions server 402 provides the functionality of the learning module 406, including generation or retrieval from the category identifiers and the correlation criteria. In these implementations, the learning module 406 is not part of system 108.

Figure 3:
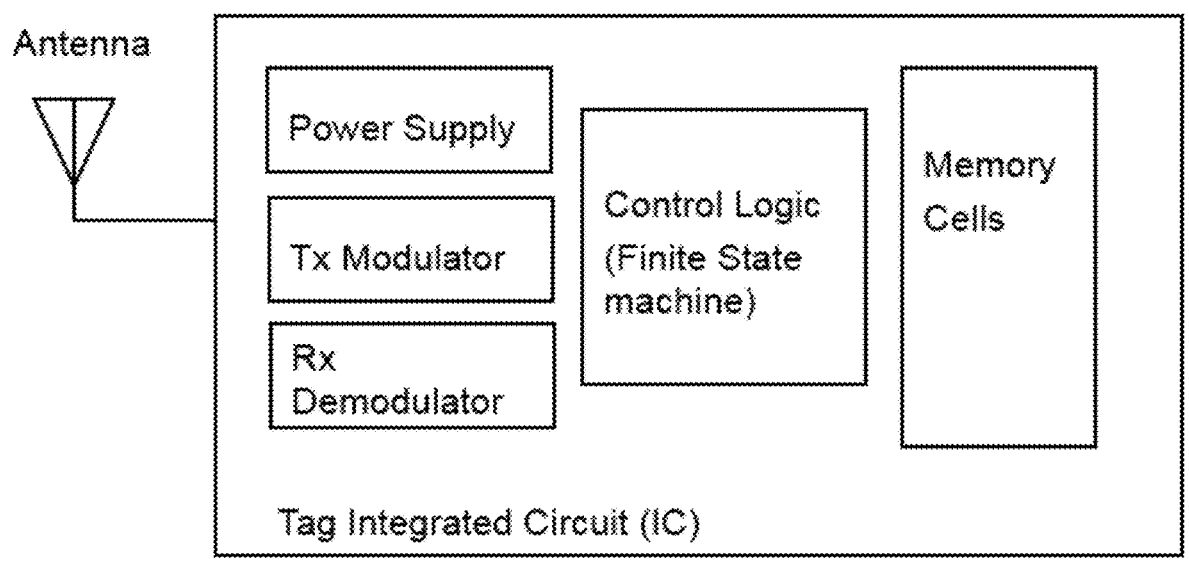
FIG. 3 is an RFID tag block diagram showing the components of an RFID antenna and tag integrated circuit (IC) including power supply, Tx modulator, Rx modulator, control logic, and memory cells.
Figure 4:
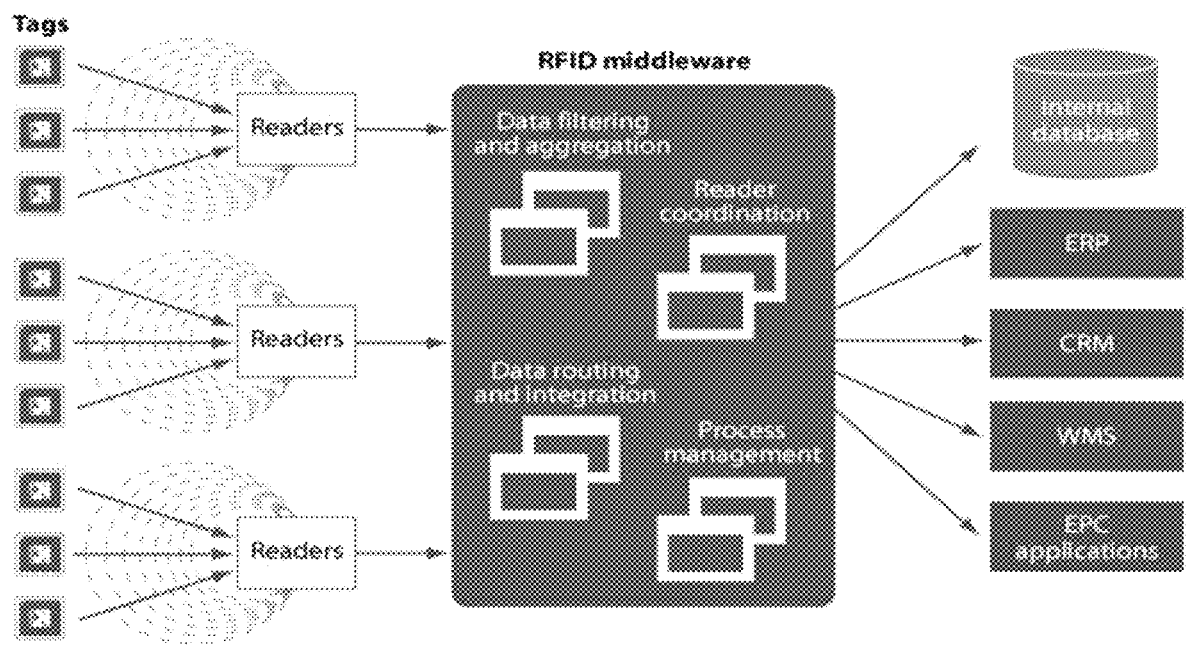
FIG. 4 is schematic of non-limiting examples of RFID middleware comprising RFID tags, RFID readers, and RFID middleware comprising the functions of Data filtering and aggregation; reader coordination, data routing and integration, and process management; the middleware connected to one or more of an internal database, ERP, CRM, WMS, and EPC applications.
Figure 21:
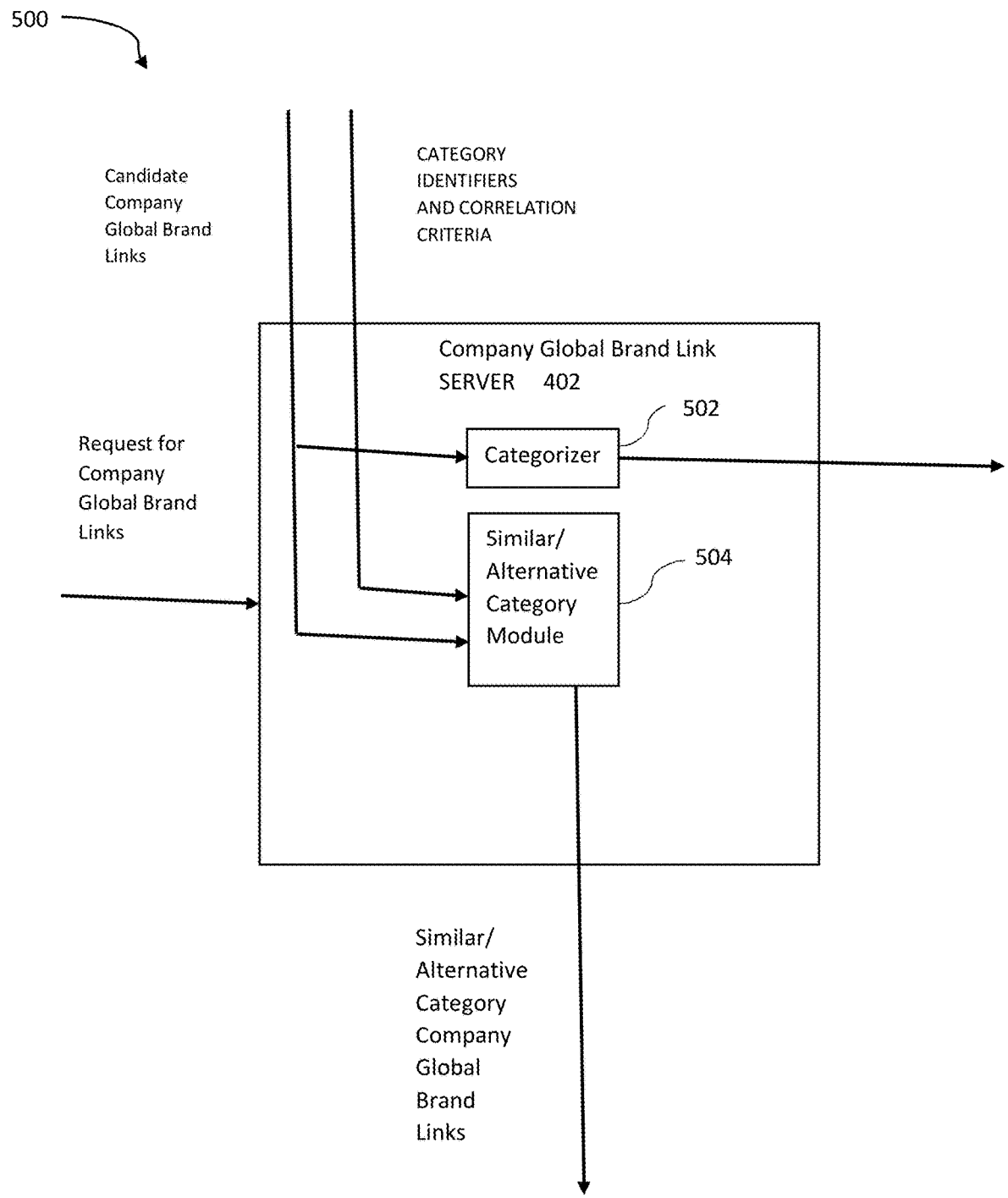
FIG. 21 is a block diagram of an example implementation of the company/brand/social/global EMFID tag interactions server hereof.
Figure 22:
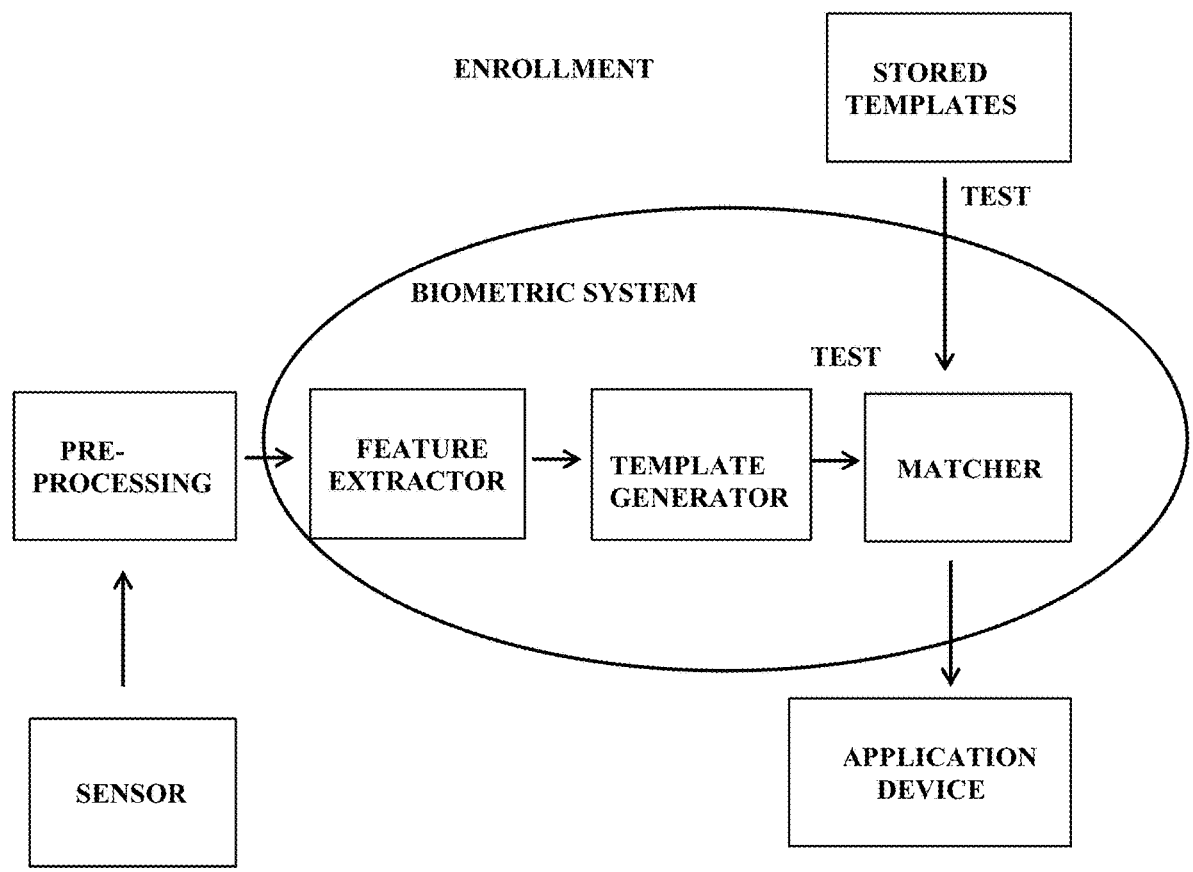
FIG. 22 is a block diagram wherein said EMFID tag communications data is monitored, collected, and/or analyzed by one or more unmanned surveillance vehicles, satellites or hand-held devices.

FIG. 21 is a block diagram of an example implementation 500 of the company/brand/social/global EMFID tag interactions server 402 of FIG. 3. The company/brand/social/global EMFID tag interactions server 402 includes a categorizer 502 and a cluster/anti-cluster module 504.

The company/brand/social/global EMFID tag interactions server 402 receives requests for related company/brand/social/global EMFID tag interactions promotional data set. The related company/brand/social/global EMFID tag interactions promotional data set request may include a number of related company/brand/social/global EMFID tag interactions promotional data set desired and the number of related company/brand/social/global EMFID tag interactions categories per related company/brand/social/global EMFID tag interactions promotional data set. The number of related company/brand/social/global EMFID tag interactions promotional data set desired can be used to determine whether related company/brand/social/global EMFID tag interactions categories should be same, similar, broad or alternative, clusters or groupings.

The company/brand/social/global EMFID tag interactions server 402 receives candidate related company/brand/social/global EMFID tag interactions. In some implementations, the candidate related company/brand/social/global EMFID tag interactions are ordered by relevance to the requested content marketing EMFID tag communications. The company/brand/social/global EMFID tag interactions server 402 can receive the ordered list of candidate company/brand/social/global EMFID tag interactions. Alternatively, the company/brand/social/global EMFID tag interactions server 402 can receive an unordered list, and the company/brand/social/global EMFID tag interactions server 402 can order the candidate company/brand/social/global EMFID tag interactions by relevance to the requested content marketing EMFID tag communications using a relevance measure.

The categorizer 502 of the company/brand/social/global EMFID tag interactions server 402 identifies categories for the candidate related company/brand/social/global EMFID tag interactions. In some implementations, the categories are the same as the related company/brand/social/global EMFID tag interactions, and the categorizer 502 is not included in the company/brand/social/global EMFID tag interactions server 402.

The company/brand/social/global EMFID tag interactions server 402 receives one or more correlation criteria for each category. In some implementations, the company/brand/social/global EMFID tag interactions server 402 also receives the one or more category identifiers associated with each category. In some implementations, category identifiers are also received for the web page concepts and are used to cluster or anti-cluster company/brand/social/global EMFID tag interactions categories.

The candidate company/brand/social/global EMFID tag interactions and the correlation criteria are provided as inputs to the cluster/anti-cluster module 504. If the request is for a single related company/brand/social/global EMFID tag interactions promotional data set, the classification of the categories by characteristics, (also called categories) is used to improve the diversity of categories coverage, (alternative category clustering) of the related company/brand/social/global EMFID tag interactions categories displayed in the single related company/brand/social/global EMFID tag interactions promotional data set. If the request is for multiple related company/brand/social/global EMFID tag interactions promotional data set, the classification of the related company/brand/social/global EMFID tag interactions categories by categories is used to cluster related company/brand/social/global EMFID tag interactions categories in one related company/brand/social/global EMFID tag interactions promotional data set in the same category or similar categories while those in other related company/brand/social/global EMFID tag interactions promotional data set are from varying categories.

The features described can be implemented in digital electronic circuitry, or in computer hardware, firmware, software, or in combinations of them. The features can be implemented in a computer program product tangibly embodied in an information carrier, e.g., in a machine-readable storage device or in a propagated signal, for execution by a programmable processor; and method steps can be performed by a programmable processor executing a program of instructions to perform functions of the described implementations by operating on input data and generating output.

The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, (e.g., Objective-C, Java), including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor one of multiple processors or cores, of any kind of computer. Generally, a processor can receive instructions and other data to develop a profile for one or more end user, pet, livestock, dairy cows, cattle or other animals, including tracking movement, logistics data, and/or location data using radio and other frequency tags and relaying data from EMFID tag interactions to a database that can be accessed by members of a network from a read-only memory or a random access memory or both. The essential elements of a computer are a processor for executing instructions and one or more memories for storing instructions and data. Generally, a computer can also include, or be operatively coupled to communicate with one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs, (application-specific integrated circuits).

To provide for interaction with a user, the features can be implemented on a computer having a display device such as a CRT, (cathode ray tube) or LCD, (liquid crystal display) monitor for displaying information to the user, pet, livestock, dairy cows, cattle or other animal and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The computer system can include clients and servers. A client and server are generally remote from each other and typically interact through a network. The relationship of client and server arises by virtue of computer programs running on the respective computers and having a client-server relationship to each other.

Potential Aspects or Elements of the Claimed Invention that can be Optionally Excluded or Negatively Claimed The present claimed subject matter can also in particular claimed embodiments exclude or negatively claim one or more aspects, e.g., to more particularly recite or exclude embodiments or elements that might occur in cited or other published art, as presented herein. Accordingly, the present invention can optionally exclude, not include, or not provide, one of more, or any combination of any element, feature, component or step disclosed herein.

A number of implementations have been described. Nevertheless, it can be understood that various modifications may be made. For example, elements of one or more implementations may be combined, deleted, modified, or supplemented to form further implementations. As yet another example, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other implementations are within the scope of the following claims.

What is claimed is:

1. An electromagnetic frequency (EMF) identification (EMFID) method to provide promotions of interest to present and potential customers using an EMFID tag device that provides automatic data collection, transfer to, and storage on, non-transitory computer readable storage media of customer end user data of said present and potential customers, using a wireless device using said customer end user data to generate and store profiles for each of said customer end users as said present and potential customers, said profiles stored on a computer database that can be accessed by members of a computer network, wherein predictive analytics are used with said customer end user data to generate said promotions of interest in said database for access by said members, for said members to provide said promotions of interest to said present and potential customers;

the method comprising:
(a) electronically assigning to the customer end user, on an electronic network computing system via a processor, a unique identifier for said EMFID tag device of the customer end user of a mobile or stationary computing device that transmits said customer end user data via said EMFID tag device or via said computing device; wherein the EMFID tag device comprises an EMFID microchip combined with an antenna, wherein the EMFID tag device is configured to: (i) pick up signals from an EMFID reader or scanner and then return the signals with the additional data of the customer end user; and (ii) allow the EMFID tag device to be tracked along with associated object as the customer end user assigned to the EMFID tag device;

wherein the customer end user data comprising:
(i) customer end user product and service information data accessed by, or assigned to, the customer end user;

(ii) customer end user biometric, healthcare, health, and medical condition, pharmaceutical prescription, and electronic medical record (EMR) data;

(iii) customer end user personal and profile information data; and (iv) customer end user sales, browsing, tracking, and personal identification information data comprising (A) service provider and sales information data, (B) product provider and sales information data, (C) web browsing and tracking information data, (D) user GPS, travel, currency, monitoring, and personal identification information data; and (v) EMFID tag communications data comprising at least all of: (A) the customer end user data; (B) communications data between two or more commercial parties including the use of: (1) the EMFID tag device, (2) the customer end user data, and (3) communications data comprising data of customers, companies, patients, retailers, global brands, milk or farm production, related to the commercial parties' products or services; and (D) customer end user data relating to said promotions of interest for products or services via the Internet, wireless communications, and social media; the assigning including the unique identifier assigned to the customer end user;

(b) electronically and automatically collecting, on computer readable media, the customer end user data from the customer end user of said present and potential customers, on computer readable media, an electronic network computing system via a processor, communicated from the EMFID tag device of the customer end user by a mobile or stationary computing device that transmits said customer end user data; and (c) using said customer end user data to generate and store said profiles for each of said customer end users as said present and potential customers, said profiles stored on said computer database that can be accessed by said members of said computer network, using said predictive analytics with said customer end user data to generate said promotions of interest in said database for access by said members;

(d) electronically providing on a computer system, network or system, consumer or brand sentiment rating processing of said customer end user data using structured analytical measurements customer end user communications and social media content that refers to member related consumer products and services to electronically determine using, a computer system, network or system processor, at least one consumer or brand sentiment rating data set for the online activity, communications, and social media content of said customer end users; and electronically assigning on a computer system consumer or brand sentiment rating data sets for one or more of the online activity, communications, and social media content data sets of said customer end users relating to said member related products or services;

wherein said electronically determining the consumer or brand sentiment rating data sets includes using said customer end user data for all of:

(i) electronically identifying, using a computer system processor, data sets comprising positive terms or phrases associated with consumer products or services of said members or related products or services and with said customer end user data, relating to said promotions, of interest in one or more of the online activity, communications, and social media content data sets;

(ii) electronically searching on a computer system processor in a set of closest N words from the terms or phrases of interest for keywords expressing said consumer or brand sentiment about the terms or phrases of interest;

(iii) electronically assigning using a computer system processor, a probability value data set for one or more of the keywords, the probability value indicating the probability that the positive keywords about the terms or phrases of interest;

(iv) electronically assigning using a computer system processor one or more occurrences of the terms or phrases of interest with a consumer or brand sentiment score data value based on the keywords in the set of closest N words from the terms or phrases of interest; and (v) electronically summing using a computer system processor one or more consumer or brand sentiment score assigned to each of the terms or phrases of interest in each social media conversation to electronically obtain, using computer system processor, as a consumer brand or sentiment score based on the consumer or brand sentiment rating data sets concerning products or services or activities and remotely storing, monitoring and retrieving data, wherein predictive analytics are used for customer end user analysis of said customer end user data, marketing data, and data relating to promotions of interest of said members or related products or services and target markets to provide said promotions of interest for said customer end users;

(e) calculating correlation values between said consumer or brand sentiment scores for said member related products or services of the customer end users and said promotions, of interest varies by online source or group of sources; and calculating how the consumer or brand sentiment score trends over time and varies by online source or group of sources to provide additional promotions of interest relating to said members products or services based on said customer or brand sentiment score; and (f) calculating how the consumer or brand sentiment scores for said member related products or services of the customer end users relates to said promotions, of interest varies by online source or group of sources; and calculating how the consumer or brand sentiment score trends over time and varies by online source or group of sources to provide additional promotions of interest relating to said members products or services based on said customer or brand sentiment score.

2. A method according to claim 1, further comprising displaying the actionable wireless use of EMF transmissions relating to said data to provide data transfer for real-time tracking of EMFID communications of said end user data.

3. A method according to claim 1, wherein the consumer or brand sentiment score is based on one or more of: how many times each occurrence of the terms or phrases of interest appears in the social media conversation; number of keywords expressing consumer or brand sentiment about the terms or phrases of interest in the set of closest words; whether each keyword reflects a positive, negative or neutral consumer or brand sentiment scores about consumer goods or services related to goods or services of said members and said consumer end users EPC tag device communications, said promotions of interest; and relevance of the keywords expressing consumer or brand sentiment scores about the terms or phrases of interest.

4. A method according to claim 3, wherein the relevance of the keywords is electronically determined by using a computer system electronically analyzing one or more of: linguistic modifiers of the keywords expressing consumer or brand sentiment about the terms or phrases of interest including one or more of negations, comparatives, and enumerations; and proximity of the keywords to the terms or phrases of interest of the consumer end user data in the online social media conversation.

5. A method according to claim 1, further comprising electronically analyzing and using online social media author and website influence parameter data on a computer system in classifying the consumer or brand sentiment data of consumer online activity, behavior, or social media conversations or content data of the consumer end user.

6. A method according to claim 1, further comprising determining an overall volume of the radio frequency location and identification data transfer to a database that can be accessed by members of a network for products or services or promotions of interest via the Internet, communications, and social media content referring to consumer products or services and data of the radio frequency location and identification data of the customer end users and transfer to a database that can be accessed by said members of said network for products or services for said promotions of interest via the Internet, communications, and social media content per unit of time.

\* \* \* \* \*